US006969513B2

(12) United States Patent  
Galen

(10) Patent No.: US 6,969,513 B2
(45) Date of Patent: Nov. 29, 2005

(54) PLASMID MAINTENANCE SYSTEM FOR ANTIGEN DELIVERY

(75) Inventor: James E. Galen, Owings Mills, MD (US)

(73) Assignee: University of Maryland, Baltimore, Baltimore, MD (US)

(*) Notice: Subject to any disclaimer, the term of this patent is extended or adjusted under 35 U.S.C. 154(b) by 79 days.

(21) Appl. No.: 10/750,965

(22) Filed: Jan. 5, 2004

(65) Prior Publication Data

US 2004/0161420 A1 Aug. 19, 2004

Related U.S. Application Data

(60) Division of application No. 09/453,313, filed on Dec. 2, 1999, now Pat. No. 6,703,233, which is a continuation-in-part of application No. 09/204,117, filed on Dec. 2, 1998, now Pat. No. 6,413,768.
(60) Provisional application No. 60/158,738, filed on Oct. 12, 1999.

(51) Int. Cl.$^7$ .................. A61K 48/00; A61K 39/112; C12N 15/63
(52) U.S. Cl. ............... 424/93.2; 424/93.1; 424/93.4; 424/93.6; 424/234.1; 424/236.1; 424/258.1; 435/320.1; 536/23.1; 536/23.7; 536/24.1
(58) Field of Search .................. 424/93.1, 93.2, 424/93.6, 234.1, 236.1, 258.1; 435/320.1; 536/23.1, 23.7, 24.1

(56) References Cited

U.S. PATENT DOCUMENTS

| 4,735,801 | A | 4/1988 | Stocker |
| 4,760,022 | A | 7/1988 | Molin et al. |
| 4,764,370 | A | 8/1988 | Fields et al. |
| 5,459,072 | A | 10/1995 | McKay et al. |
| 5,527,529 | A | 6/1996 | Dougan et al. |
| 5,545,541 | A | 8/1996 | Molin et al. |
| 5,643,771 | A | 7/1997 | Stocker |
| 5,672,345 | A | 9/1997 | Curtiss, III |
| 5,674,703 | A | 10/1997 | Woo et al. |
| 5,695,983 | A | 12/1997 | Miller et al. |
| 5,763,270 | A | 6/1998 | Eastman et al. |
| 5,770,214 | A | 6/1998 | Dougan et al. |
| 5,804,194 | A | 9/1998 | Dougan et al. |
| 5,824,538 | A | 10/1998 | Branstrom et al. |
| 5,851,519 | A | 12/1998 | Dougan et al. |
| 5,853,718 | A | 12/1998 | Molin et al. |
| 5,922,583 | A | 7/1999 | Morsey |

OTHER PUBLICATIONS

Schodel et al., Infect. Immun., 1994, vol. 62, No. 5, pp. 1669–1676.*
Summers, *The Biology of Plasmids*, pp. 65–91 (1996).
Jensen et al, *Molecular Microbiology*, 17(2):205–210 (1995).
Pecota et al, *Applied and Environmental Microbiology*, 63(5):1917–1924 (1997).
Boe et al, *Journal of Bacteriology*, 169(10):4646–4650 (1987).
Gerdes et al, *Annu. Rev. Genet.*, 31:1–31 (1997).
Gultyaev et al, *J. Mol. Biol.*, 273:26–37 (1997).
Franch et al, *J. Mol. Biol.*, 273:38–51 (197).
Mikkelsen et al, *Molecular Microbiology*, 26(2):311–320 (1997).
Franch et al, *Mol. Microbiol.*, 21(5):1049–1060 (1996).
Gerdes et al, *J. Mol. Biol.*, 190:269–279 (1986).
Gerdes et al, *Genetic Eng.*, 19:49–61 (1997).
Gerdes et al, *J. of Bacteriology*, 161(1):292–298 (1985).
Wu et al, *Biotechnology and Bioeng.*, 44:912–921 (1994).
Wood et al, *Biotechnology and Bioeng.*, 38:397–412 (1991).
Gerdes, *Biotechnology*, 6:1402–1405 (1998).
Bravo et al, *Mol. Gen. Genet.*, 210:101–110 (1987).
Ruiz–Echevarria et al, *Mol. Microbiol.*, 5(11):2685–2693 (1997).
Ruiz–Echevarria et al, *Gen Genet.*, 248:599–609 (1995).
Ruiz–Echevarria et al, *J. Mol. Biol.*, 247:568–571 (1995).
Bravo et al, *Mol. Gen. Genet.*, 215:146–151 (1988).
Nordstrom et al, "Control of Replication of Bacterial Plasmids: Molecular Biology, and Physiology of the Plasmid R1 System", Academic Press Inc., pp. 71–91 (1984).
Gerdes et al, "Antisense RNA–Regulated Programmed Cell Death", Annual Rev. Inc, pp. 1–31 (1997).
Nordstrom et al, BIOSCI, pp. 294–300 (1994).
Pedersen et al, *Mol. Microbiol.*, 32(50):1090–1102 (1999).
Melton–Celsa et al, "The Structure, Biology, and Relative Toxicity for Cellsa dna Animals of Shiga Toxin Family Members", Uniformed Services University of the Health Sciences, pp. 1–23.
Dolfing et al, *ASM News*, 62(3):117–119, (1996).
Keeler et al, *Handbook of Natural Toxins*, 8:313–327.
Konowalchuck et al, *The Lancet*, 351:1003 (1998).
Endo et al, *Eur. J. Biochem.*, 171:45–50 (1988).
Gerdes et al, *Proc. Natl. Acad. Sci,*, USA, 83:3116–3120 (1986).
Gyles, *Can. J. Microbiol.*, 38:732–746 (1992).
Jackson et al, *Federation of European Microbiological Societies*, 44:109–114 (1987).
Tesh et al, *Inf. and Immun.*, 61(8):3392–3402 (1993).
Lindgren et al, *Inf. and Immun.*, 62(2):623–631 (1994).

(Continued)

*Primary Examiner*—David Guzo
(74) *Attorney, Agent, or Firm*—Sughrue Mion, PLLC

(57) ABSTRACT

The present invention relates generally to a Plasmid Maintenance System for the stabilization of expression plasmids encoding foreign antigens, and methods for making and using the Plasmid Maintenance System. The invention optimizes the maintenance of expression plasmids at two dependent levels by: (1) removing sole dependence on balanced lethal maintenance functions; and (2) incorporating at least one plasmid partition function to present random segregation of expression plasmids, thereby enhancing their inheritance and stability. The Plasmid Maintenance System may be employed within a plasmid which has been recombinantly engineered to express a variety of expression products.

35 Claims, 28 Drawing Sheets

OTHER PUBLICATIONS

Figure 1A:
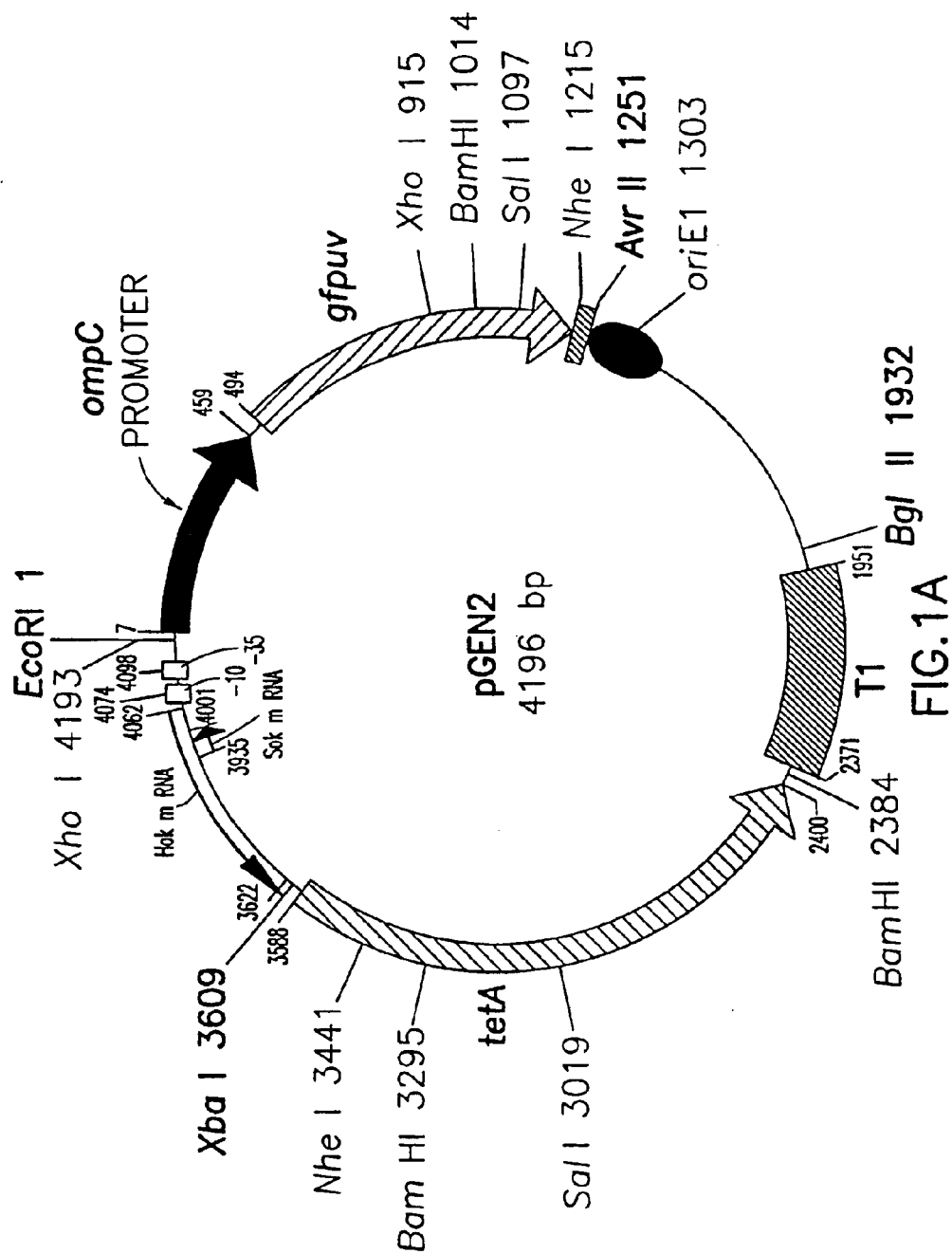

Sung et al, *J. of Bacteriol.*, 172(11):6386–6395 (1990).
Muhldorfer et al, *Inf. and Immunol.*, 64(2):495–502 (1996).
Schmitt et al, *Inf. and Immunol.*, 59(3):1065–1073 (1991).
Weinstein et al, *J. of Bacteriol.*, 170(9):4223–4230 (1988).
Gyles et al, *Microbial Pathogenesis*, 5:419–426 (1988).
Paton et al, *Infect. and Immunity*, 63(7):2450–2458 (1995).
Paton et al, *Microbial Pathogenesis*, 15:77–82 (1993).
Stein et al, *Nature*, 355:748–750 (1992).
Per–Georg et al, *Int. J. Biol. Macromol.*, 17(3–4):199–204 (1995).
Per–Georg et al, *Chemistry & Biology.*, 3(4):263–275 (1996).
Ling et al, *Biochemistry*, 37:1777–1788 (1998).
Hovde et al, *Proc. Natl. Acad. Sci., USA*, 85:2568–2572 (1988).
Yamasaki et al, *Microbial Pathogenesis*, 11:1–9 (1991).
Jackson et al, *J. of Bacteriology*, 172(6):3346–3350 (1990).
Gordon et al, *Inf. and Immun.*, 60(2):485–490 (1992).
Bosworth et al, *Inf. and Immun.*, 64(1):55–60 (1996).
Jackson, *J. of Bacteriology*, 172(2):653–658 (1990).
Clark, *Mol. Microbiology*, 19(4):891–899 (1996).
Bast, *Inf. and Immun.*, 65(6):2019–2028 (1997).
Perera et al, *J. of Bacteriology*, 173(3):1151–1160 (1991).
Perera et al, *Inf. and Immun.*, 59(3):829–835 (1991).
Downes et al, *Inf. and Immun.*, 56(8):1926–1933 (1988).
Su et al, *Inf. and Immun.*, 60(8):3345–3359 (1992).
Su et al, *Microbial Pathogenesis*, 13:465–476 (1992).
Richardson et al, *Inf. and Imm.*, 60(10):4154–4167 (1992).
Nelson et al, "Biological Activity of Verocytotoxin (VT)2c and VT1/VT2c chimeras in the rabbit model", Elsevier Science, pp. 245–249 (1994).
Bielaszewska et al, *Inf. and Immun.*, 65(7):2509–2516 (1997).
Streatfield et al. *Proc. Natl. Acad. Sci., USA*, 89:12140–12144 (1992).
Acheson et al, *Inf. and Immun.*, 64(1):355–357 (1996).
Wadolkowski et al, *Inf. and Immun.*, 58(12):3959–3965 (1990).
Karpman et al, *J. of Infect. Dis.*, 175:611–620 (1997).
Louise et al, *J. of Infect. Dis.*, 172:1397–1401 (1995).
Boyd et al, *Nephron*, 51:207–210 (1989).
Zoja et al, *J. Lab. Clin. Med.*, 120(2):229–238 (1992).
McDaniel et al, *Proc. Natl. Acad. Sci., USA*, 932:1664–1668 (1995).
Jarvis et al, *Proc. Natl. Acad. Sci., USA*, 927996–8000 (1995).
Jarvis et al, *Inf. and Immun.*, 64(11):4826–4829 (1996).
Sixma et al, *Biochemistry*, 32:191–198 (1993).
Mangeney et al, *Cancer Res.*, 53:5314–5319 (1993).
Franke et al, *J. of Clin. Microbiology*, 33(12):3174–3178 (1995).
Kim et al, *Micro. Immunol.*, 41(10):805–808 (1997).
Butterton et al, *Infect. and Immunity*, 65(6):2127–2135 (1997).
Nataro et al, *Amer. Soc. for Microbiology*, 11:164–178 (1998).
Taga et al, *Blood*, 90(7):2757–2767 (1997).
Haddad et al, *J. of Bacteriology*, 175(16):4970–4978 (1993).
Gannon et al, *J. of General Microbiology*, 136:1125–1135 (1990).
O'Brien et al, *Micro. and Immunol.*, 180:66–93 (1992).
Montfort et al, *J. of Biological Chem.*, 262(11):5398–5403 (1987).
Lindgren et al, *Inf. and Immun.*, 61(9):3832–3842 (1993).
Rasmussen et al, *Mol. Gen. Genet.*, 209(1):122–128 (1987).
Gerdes et al, *Mol. Microbiol.*, 4(11):1807–1818 (1990).
Ito et al, *Microbial Pathogenesis*, 8:47–60 (1990).
Fraser et al, *Structural Biology*, 1(1):59–64 (1994).
Yu et al, *Mol. Microbiol.*, 6(3):411–417 (1992).
Thisted et al, *J. Mol. Biol.*, 247:859–873 (1995).
Thisted et al, *The EMBO Journal*, 13(8):1950–1959 (1994).
Kim et al, *J. of Fermentation and BioEng.*, 82(5):495–497 (1996).
Su et al. *Inf. and Immun.*, 60(8):3345–3359 (1992).
Gordon et al, *Infect. and Immun.*, 60(2):485–490 (1992).
Galen et al, *Infect. and Immun.*, 67(12):6424–6433 (1999).

* cited by examiner

Figure 3D:
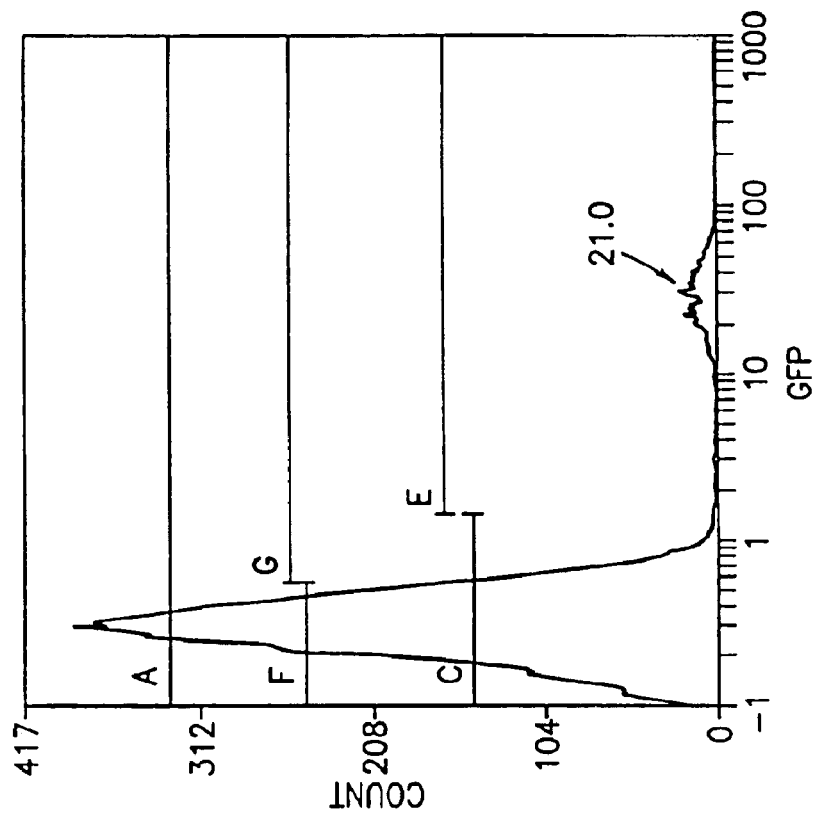
Figure 3C:
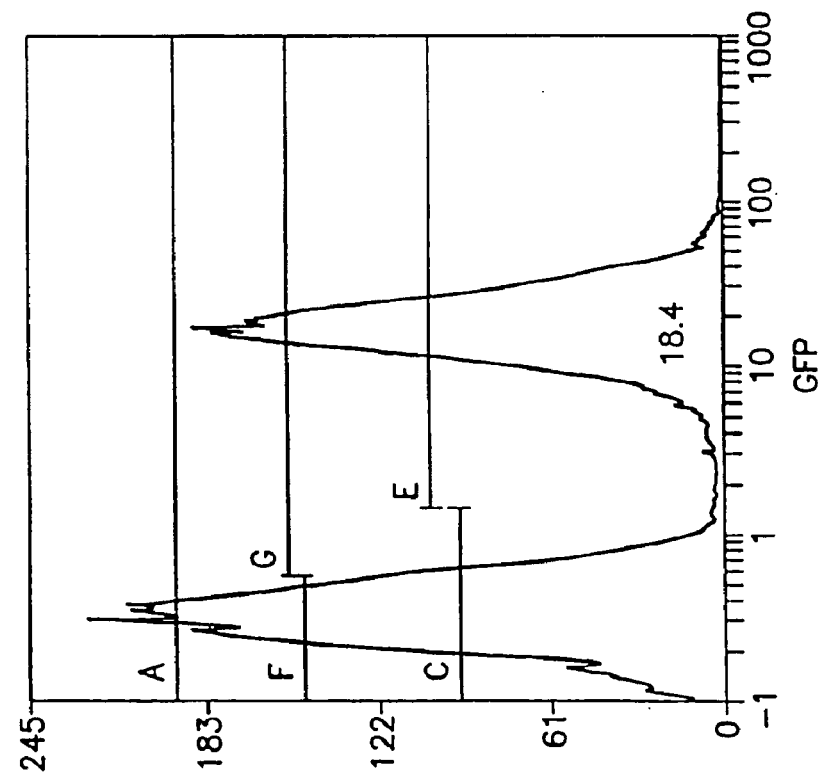
Figure 3F:
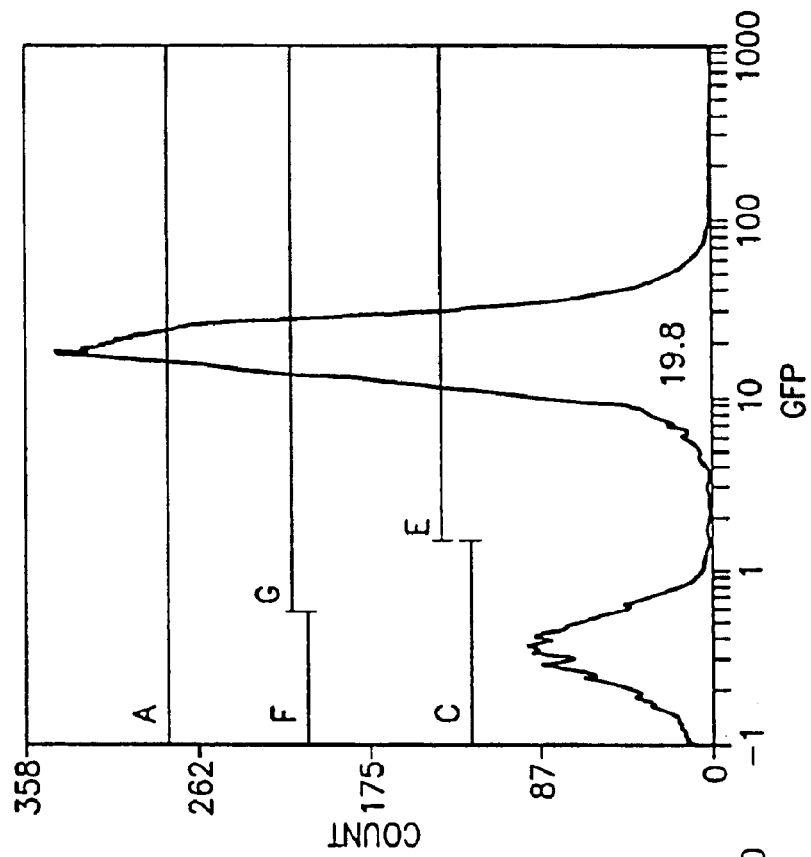
Figure 3E:
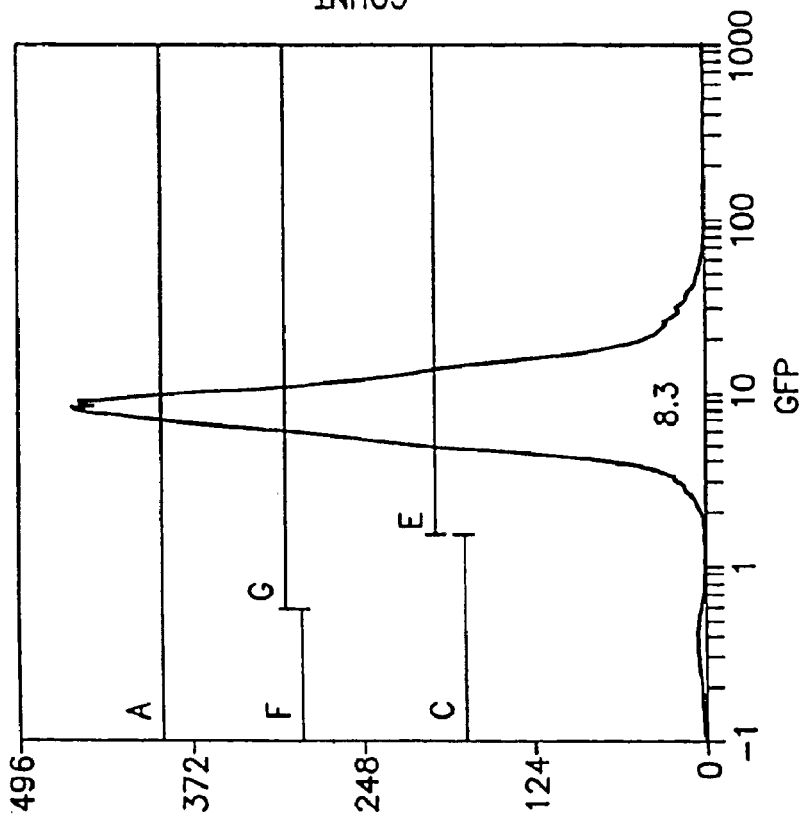
Figure 3H:
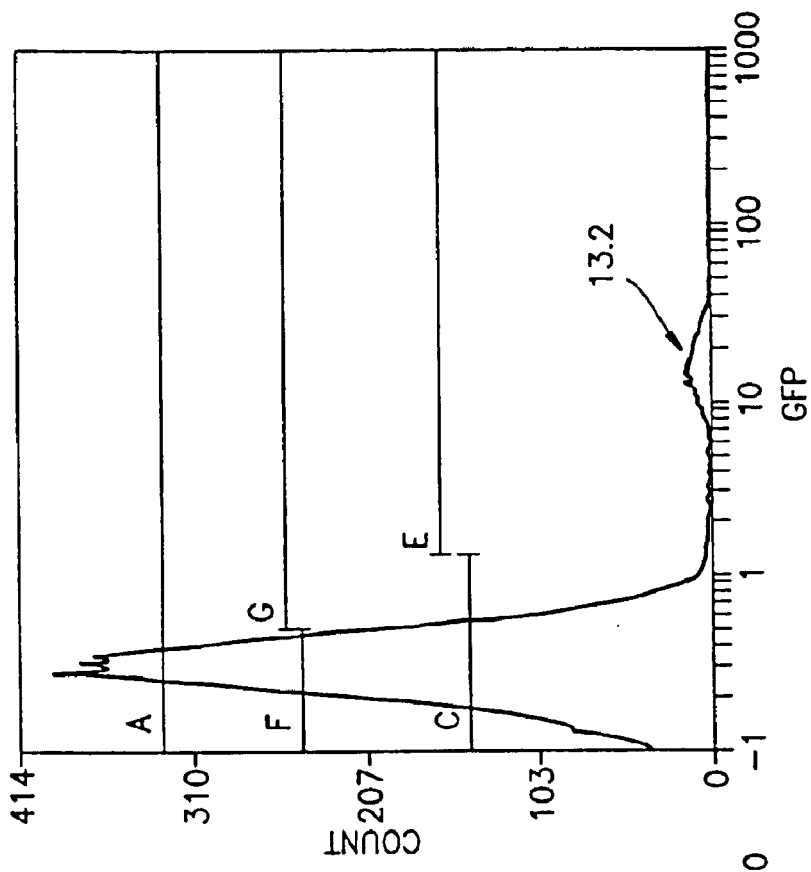
Figure 3G:
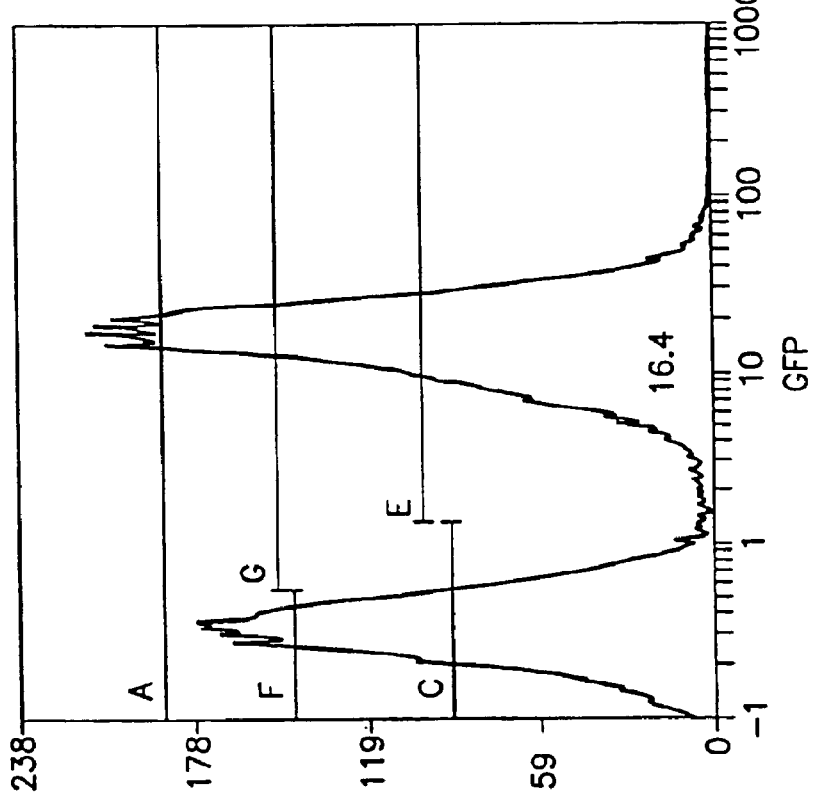

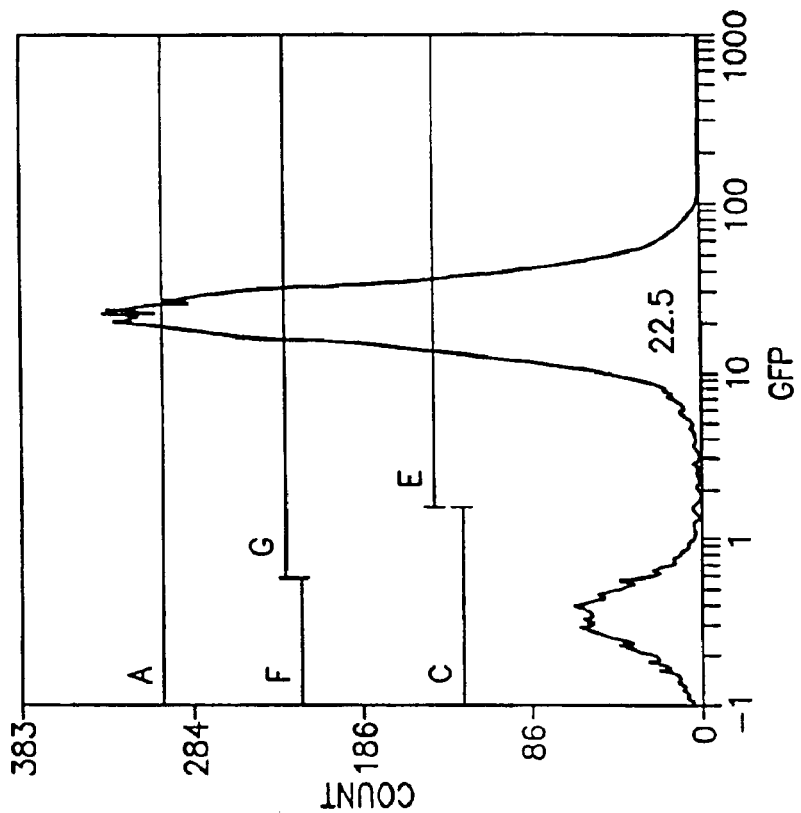
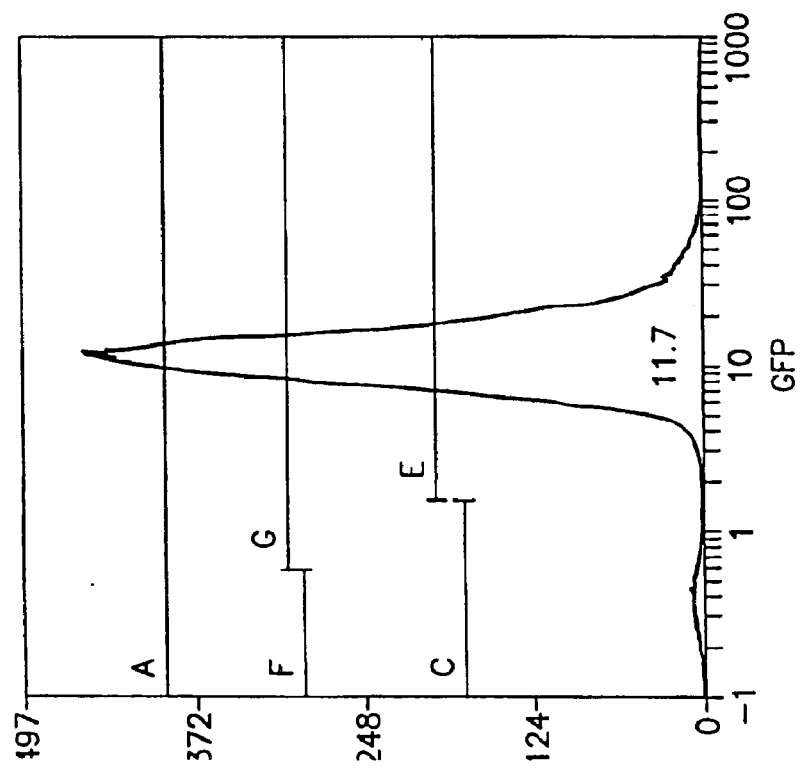
FIG.3B
FIG.3A

FIG. 4A

```
gaattctgtg gtagcacaga ataatgaaaa gtgtgtaaag aaggtaaaa aaaacgaat    60
gcgaggcatc cggttgaaat agggtaaac agacattcag aaatgaatga cggtaataaa   120
taagttaat gatgatagcg ggagttattc tagttgcgag tgaagtttt gttttgacat   180
tcagtgctgt caaatactta agataagtt attgatttta accttgaatt attattgctt   240
gatgttaggt gcttatttcg ccattccgca ataatcttaa aaagttccct tgcatttaca   300
ttttgaaaca tctatagcga atcttaaaag ttttagtatc atattggtgt   360
tgattattc tgcattttg gggagaatgg acttgccgac tgattaatga gggttaatca   420
gtatgcagtg gcataaaaa gcaaataaag gcatataaca gatcgatctt aacatccac   480
aggagata ctgatgagta aagagagaga actttcact ggagttgtcc caattccttgt   540
tgaattagat ggtgatgtta atggcacaa atttcgtgtc agtggagagg gtgaagtga   600
tgcaacatac ggaaaactta ccttaaatt tatttgcact actgaaaac tacctgttcc   660
atggccaaca cttgtcacta cttctcta tggtgttcaa tgcttttcc gttatccga   720
tcatatgaaa cggcatgact ttttcaagag tgccatgccc gaaggttatg tacaggaacg   780
cactatatct ttcaaagatg acggaactta caagacggt gctgaagtca agtttgaagg   840
tgataccctt gttaatcgta tcgagttgaa agtattgat tttaaagaag atggaaacat   900
tctggacac aaactcgagt gtcacacaat ctcacacaa gtatacatca cggcagacaa   960
acaaagaat ggaatcaaag ctaactcaa aattcgcac aacattgaag atggatcgt   1020
tcaactagca gaccattatc aacaaatac tccaattggc gatggccctg tcttttacc   1080
```

```
acaaccat taotgtgoa cacaatctgc ctttogaaa gatoccaaog aaaagogtga 1140
cacatggtc cttcttgagt ttgtaactgc tgctgggatt acacatggca tggatgagct 1200
acaaataa tgagctagcc cgctaatga ggggcttttt ttttctcggc ctagggccag 1260
aaaggcca ggaacgtaa aaagccggg ttgctgggt ttttccatag gctcogccc 1320
tgacgagc atcacaaaaa tgagctca agtcagaggt ggcgaaaccc gacaggacta 1380
aagatacc aggggtttcc cctggaagc gtctcctgt tcgcccctg 1440
gcttaacg gataoctgtc cgctttctc ccttggggaa ggtgggct ttctcatagc 1500
caagctgta ggtatctcag ttgggtgtag gtogttgct ccaagctggg ctgtgtgcac 1560
aacccccg ttcagcccga ccgctgagc ttatccggta actatcgtct tgagtccaac 1620
ccgtaagac acgacttatc gccactggca gcagccactg gtaacagat tagcagagcg 1680
ggtatgtag gcggtgctac agagttcttg aagtggtggc ctaactacgg ctacactaga 1740
ggacagtat ttggtatctg cctgcctgctg aagccagtta ccttcggaaa aagagttggt 1800
gctcttgat ccggcaaaca aaccaaccgct ggtagcggtg gtttttttgt ttgcaagcag 1860
agattaogc gcagaaaaaa agatctcaa gaagatcctt tgatcttttc tacgggtct 1920
agctcagt agatctaaaa cactagcc aagagtttgt agaaaccgcaa aaagccatc 1980
gtcagatg gcctttctgct taatttgatg ctggcagtt tatgggggc gtcctgccg 2040
cacoctcg ggccgttgct tgcaagtt caaatccgct ccggcggat ttgtctact 2100
aggagagcg ttcacoaca acaacagat aaaagaaaag gccagtctt tgactgagc 2160
```

FIG.4B

FIG.4C

| | | | | | |
|---|---|---|---|---|---|
| ctttcgtttt | atttgatgcc | tgcagttcc | ctactctcgc | atggggagac | cccacactac | 2220 |
| atcgggct | acgggtttc | acttctgagt | tggcatggg | gtcagtggg | accacgcgc | 2280 |
| tactgcgcc | agcaaattc | tgttttatca | gaccgcttct | ggttctgat | ttaatctgta | 2340 |
| tcaggctgaa | aatctttctct | catcgccaa | aacagcaag | ctggatcccc | gatcttatca | 2400 |
| ggtcgaggtg | gcccgctcc | atgcacgcg | agcaacgcg | gggagcaga | caagtatag | 2460 |
| ggcggcct | acaatccatg | ccaaccgtt | ccatgtgctc | gccgaggcg | cataaatcgc | 2520 |
| cgtgacgatc | agggtccag | tgatcgaagt | taggctgta | agagccgcga | gcgatccttg | 2580 |
| aagctgtcc | tgatggtcgt | catctacctg | cctgacacgc | atggcctgca | acgggggat | 2640 |
| cccgatgcga | ccgaagcga | gaagaatcat | gccatccagc | ctcgcgtcgc | ctcgcgtcgc | 2700 |
| gaaccgcagc | aagagtagc | ccagcggtc | ggccgcatg | ccggcgataa | tggctgctt | 2760 |
| ctcgccgaaa | cgtttggtgg | cggacagt | gagcaaggct | tgagcgaggg | cgtgcaagat | 2820 |
| tccgaataac | gcaaggaca | ggcgatcat | cgtccgcctc | caggcaaagc | ggtcctcgcc | 2880 |
| gaaaatgacc | cagagcgctg | ccgcaactg | tcctacgagt | tgcatgataa | agaagacagt | 2940 |
| cataagtcgg | gcgcaaatag | tcatgccgg | cgccacgcg | aaggagctga | ctgggtttgaa | 3000 |
| ggctctcaag | ggcatccgtc | gagctctcc | cttatgcgac | tcctgcatta | ggaagcagcc | 3060 |
| cagtagtagg | ttgaggccgt | tgagcaccgc | ccgcgcaagg | aatggtgcat | gcaaggagat | 3120 |
| gggccaac | agtcccccgg | ccacgggggc | ccaccata | tgcaccgga | aacaaggct | 3180 |
| catgagccg | aagtggccga | ccgatcttc | ccatcggttg | atgtcggcga | tatagccgc | 3240 |

```
gcaacgca  ctgtgtggc  cgtgatgcc  ggcaagatg  cgtccggcgt  agaggatca  3300
aggacgggt  gtgtcgcca  tgatccgta  gtcgatagtg  gctccaagta  gggaagcgag  3360
aggactggg  ccggccaa   agggtcga   cagtgctccg  agaacgggtg  cgcatagaaa  3420
cgcatcaac  gcatatagcg  ctagcagcac  gcatagtga   ctggcgatgc  tgtcggaatg  3480
acgatatcc  cgcaagaggc  cggcagtgc  cggcataacc  aagctatgc   ctacagcatc  3540
agggtgacg  gtgccgagga  tgacgatgag  cgcattgtta  gatttcattt  tttttttctc  3600
ctattttct  agacaacatc  agcaaggaga  aagggctac  cgggaacca   gcagccctt   3660
ataaaggcg  cttcagtagt  cagaccagca  tcagtcctga  aaaggcggc   ctggcggcgc  3720
ccagggttg  ctacttaccg  gattcgtaag  ccatgaaagc  cgcactcc    ctgtgtcgt   3780
cctgtaaag  aatctcgcac  agcgattttc  gtgtcagata  agtgaatatc  aacagtgtga  3840
acacacgat  caacacacac  cagacaaggg  aacttcgtgg  tagtttcatg  gccttcttct  3900
cttggcaa   agcgggtaa   gaggctatcc  tgatgtggac  tagacatagg  gatgcctgt   3960
gtgttaat   gaaattaac   ttactaccgg  gctatctttct  ttctgccaca  caacacggca  4020
caaccacc   ttcagtcat   gaggcagaaa  gctccaagcg  cgggcacat   catagccat   4080
taactgcac  gctgaccaca  ctcactttcc  ctgaaaataa  tccgctcatt  cagaccgttc  4140
cggggaaatc  cgtgtgattg  ttgccgcatc  accgtgcctc  cggagtttg  tctcga      4196
```

FIG.4D

```
ctacaaataa tgagctagcc cgctaatga gcggcttttt ttttctcggc ctagagata   60
cttaacaggg aagtgagagg gcgcggcaa agccgtttt ccatagctc cgccccctg  120
acaagcatca cgaaatctga cgctcaaatc agtggtggcg aaacccgaca ggactataaa  180
gataccaggc gtttccccct ggggctccc tctgtttcct gcctttcgt gcttttcggt  240
ttaccggtgt cattccgctg tttgccgc gtttgtctca ttccagcct gacactcagt  300
tcgggtagg cagttcgctc caagctggac tgtatgcaag aaccccgt tcagtcgac  360
cgctgcgcct tatccgtaa ctatcgtctt gagtccgaacc cggaaagaca tgcaaaagca  420
ccactggcag cagccactgg taattgattt agaggagtta gtcttgaagt catggcgcgg  480
ttaagctaa actgaagga caagtttttg tgactggct cctcaagcc agtaacctcg  540
gttcaagag ttggtagctc agagaaactt cgaaaaacg ccctgcaagg cggttttttc  600
```

FIG.5A

```
tttcagag caagagatta cggcagacc aaaacgatct caagaagatc atcttattaa  660
agataaaa tatttctagg atctaaaaca ctaggccaa  gagtttgtag aaagcaaaa   720
ggcatccg tcaggatggc cttctgctta atttgatgcc tggcagttta tggcggggt   780
tgcccgcc acctcaggg  ccgttgcttc gcaacgttca aatcgctcc  cgggagattt   840
cctactca ggagagcgtt cacgacaaa  caacagataa aacgaaaggc ccagtctttc   900
actgagcct ttgtttttat ttgatgctg  gcagttcct  actctcgcat ggggagaccc   960
acactacca cggctctac  ggcgtttcac ttctgagttc ggcatgggt  cagtgggac  1020
acgggcta ctgccgccag gcaaattctg ttttatcaga ccgcttctgc gttctgattt 1080
atctgtatc aggctgaaaa tctttctcta tcgccaaaa  cagccaagct ggatcccga  1140
cttatcagg tcaggtggc  ccggctccat gcaccgggac gcaacgggg  gaggcag    1197
```

FIG. 5B

| | | | | |
|---|---|---|---|---|
| ctacaaataa | tgagctagcc | cgcctaatga | gggcttt | ttttctcgc | ctagtttca | 60 |
| cctgtctcat | taggtgttac | atgctgttca | tctgttacat | tgtgatctg | ttcatggtga | 120 |
| acagtttaa | atgcaccaaa | aactcgtaaa | agctctgatg | tatctatctt | ttttacacg | 180 |
| ttttcatctg | tgcatatgga | cagtttcc | tttgatatct | aacgtgaac | agttgttcta | 240 |
| cttttgtttg | ttagtcttga | tgcttcactg | atagatacaa | gagcataag | aacctcagat | 300 |
| ccttcgtat | ttagccagta | tgttcctag | tgtggttgt | tgttttgcg | tgagccatga | 360 |
| gaacgaacca | ttgagatcat | gcttacttg | catgtcactc | aaaaatttg | cctcaaaact | 420 |
| ggtgagctga | atttttgcag | ttaaagcatc | gtgtagtgt | tttcttagtc | cgttagtag | 480 |
| gtaggaatct | gatgtaatgg | ttgttgtat | tttgtcacca | ttcattttta | tctgttgtt | 540 |
| ctcaagttcg | gttacgagat | cctcgtct | atctagttca | actggaaaa | tcaacgtatc | 600 |
| agtcgggcgg | cctcgcttat | caaccaccaa | tttcatattg | ctgtaagtgt | ttaaatcttt | 660 |
| acttattggt | ttcaaaaccc | attggttaag | ccttttaaac | tcatggtagt | tattttcaag | 720 |
| cattaacatg | aacttaaatt | catcaaggct | aatctctata | tttgccttgt | gagtttctt | 780 |
| ttgtgttagt | tcttttaata | acactcata | aatcctcata | gagtatttgt | tttcaaaaga | 840 |
| cttaacatgt | tccagattat | atttttatgaa | ttttttaac | tggaaagat | aagcaatat | 900 |
| ctcttcacta | aaaactaatt | ctaattttc | gcttgagaac | ttgcatagt | ttgtccactg | 960 |
| gaaatctca | aagcttaa | ccaaggatt | cctgatttcc | acagttctcg | tcatcagctc | 1020 |
| tctggttgct | ttagctaata | caccataagc | atttccta | ctgatgttca | tcatctgagc | 1080 |

FIG.6A

```
attggtta taagtgaacg atacogtocg ttctttcctt gtaggtttt caatcgtggg   1140
ctgagtagt gccacacagc ataaaattag cttggtttca tgctccgtta agtcatagog  1200
ctaatcgct agttcatttg ctttgaaaac gacatacatc aactaattca tcaattggtc  1260
agtgatttt taatcactat accaattgag atggctagt tactagtcct              1320
ctocttttga gttgtgggta tctgtaaatt ctgctagacc tttgctgaa aacttgtaaa  1380
cctgctaga ccctctgtaa attccgctag accttttgtgt gttttttg tttatattca  1440
gtggttata atttatagaa taaagaaga ataaaaagaa tagatccag               1500
cctgtgtat aactcactac tttagtcagt tccgcagtat tacaaaagga tgtgcaaac   1560
ctgtttgct cctctacaaa acagacctta aaacctaa ggcttaagta gcaocctogc    1620
agctogggc aaatcgctga atattcctt tgtcctcgac catcaggcac ctgagtcgct   1680
tctttttcg tgacattcag ttgctcggc tcaggctct caaggaaact ggggtaaat     1740
gcactacag gcgctttta tggattcatg caaggaaact accatata caagaaagc      1800
cgtcacggg cttctcaggg cgttttatgg cgtctgct atgtgtgct atctgactt      1860
bgctgttca gcagttcctg ccctctgatt ttccagtctg accacttgg attatccgt    1920
```

FIG.6B

```
gacaggtcat tcagactggc taatgcaccc agtaaggcag cggtatcatc aacaggctta 1980
ccgtcttac tgtcaaccgg atctaaaaca ctaggcccaa gagtttgtag aaacgcaaaa 2040
aggcatccg tcaggatggc cttctgctta atttgatgcc tggcagttta tgcggggggt 2100
cctgcccgc aacctccggg ccgttgcttc gcaaacgttca aatccgctcc cggcgattt 2160
gtcctactca ggagagcgtt cacgacaaa caacagataa aacgaaaggc ccagtctttc 2220
gactgagct ttcgtttat ttgatgctg gcagtccct actctcgcat gggagaccc 2280
cacactacca tcggcgctac ggcgttac ttctgagttc gcatgggt cagtggac 2340
caccgcgcta ctgccgcag gcaaattctg ttttatcaga ccgcttctgc gttctgattt 2400
aatctgtatc aggctgaaaa tcttctctca tccgcaaaa cagcaagct gatcccga 2460
tcttatcagg tcaggtggc ccgctccat gcaacgcgac gcaacgcggg gaggcagaca 2520
agtataggg ccgcgctac aatccatgcc aaccgttcc atgtgctgc cgaggcggca 2580
taaatccgcg tgacgatcag cggtccagtg atcgaagtta ggctggtaag agccgcgagc 2640
gatcctt                                                        2647
```

FIG.6C

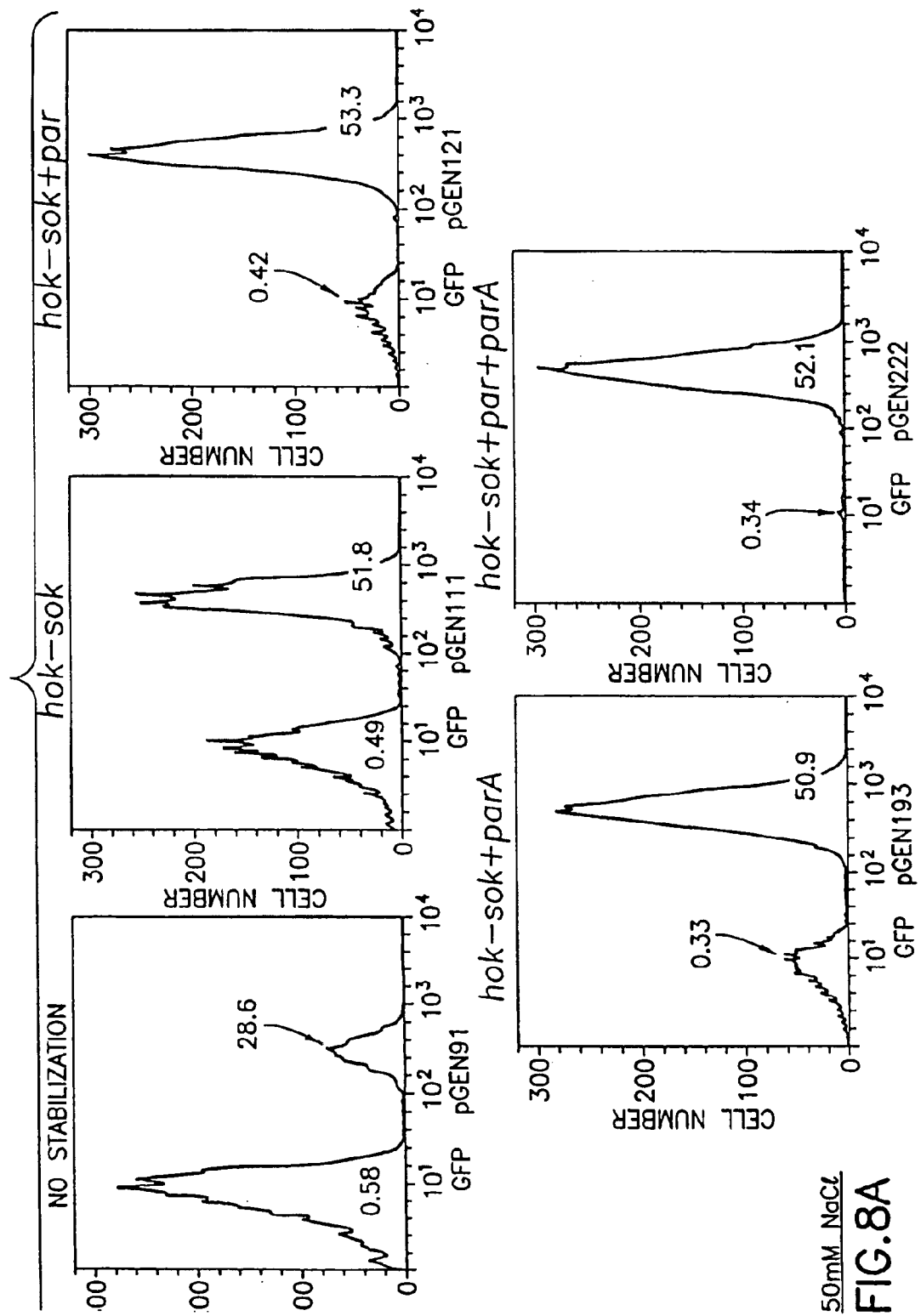
FIG. 8A 50mM NaCl

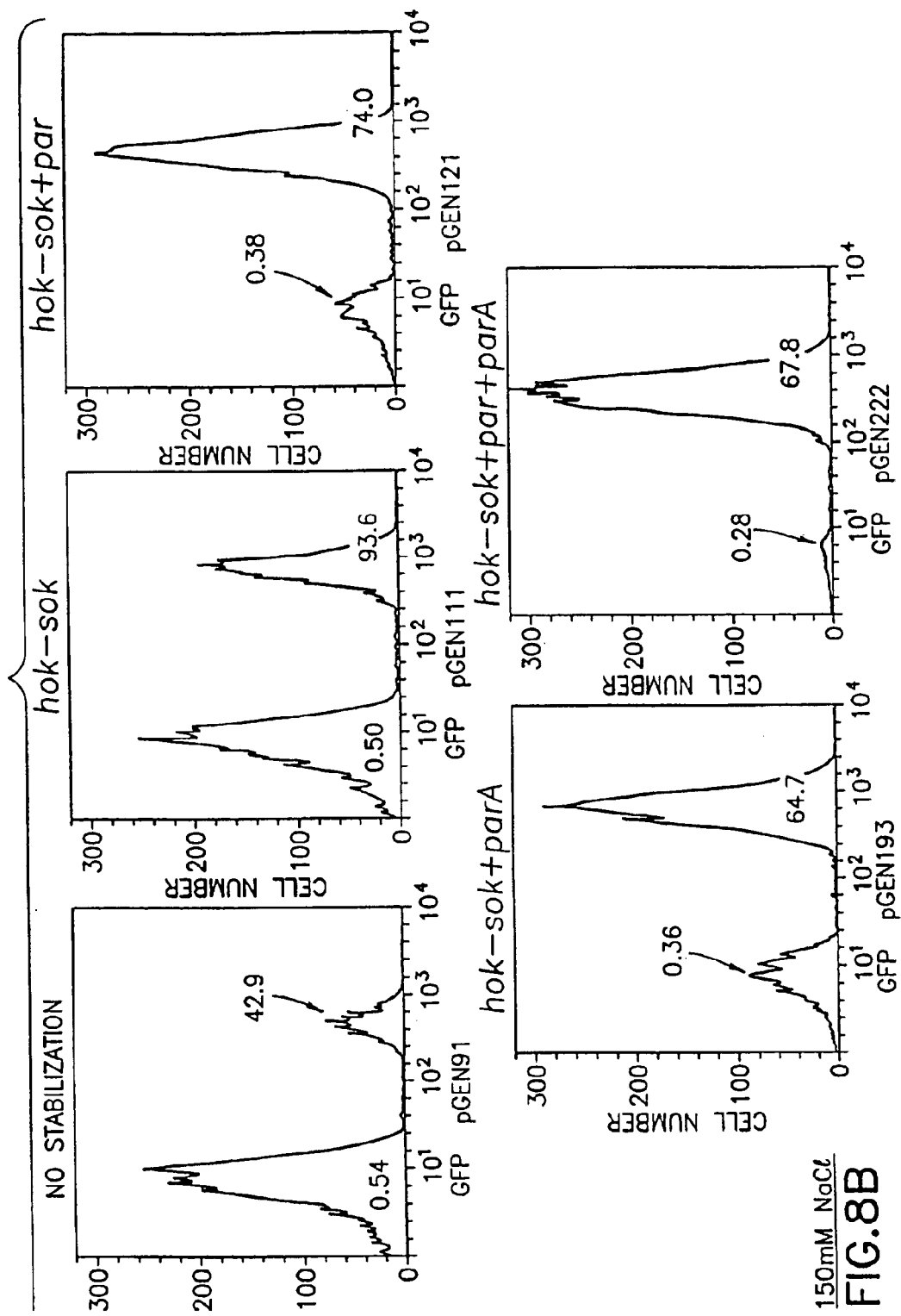
FIG. 8B 150mM NaCl

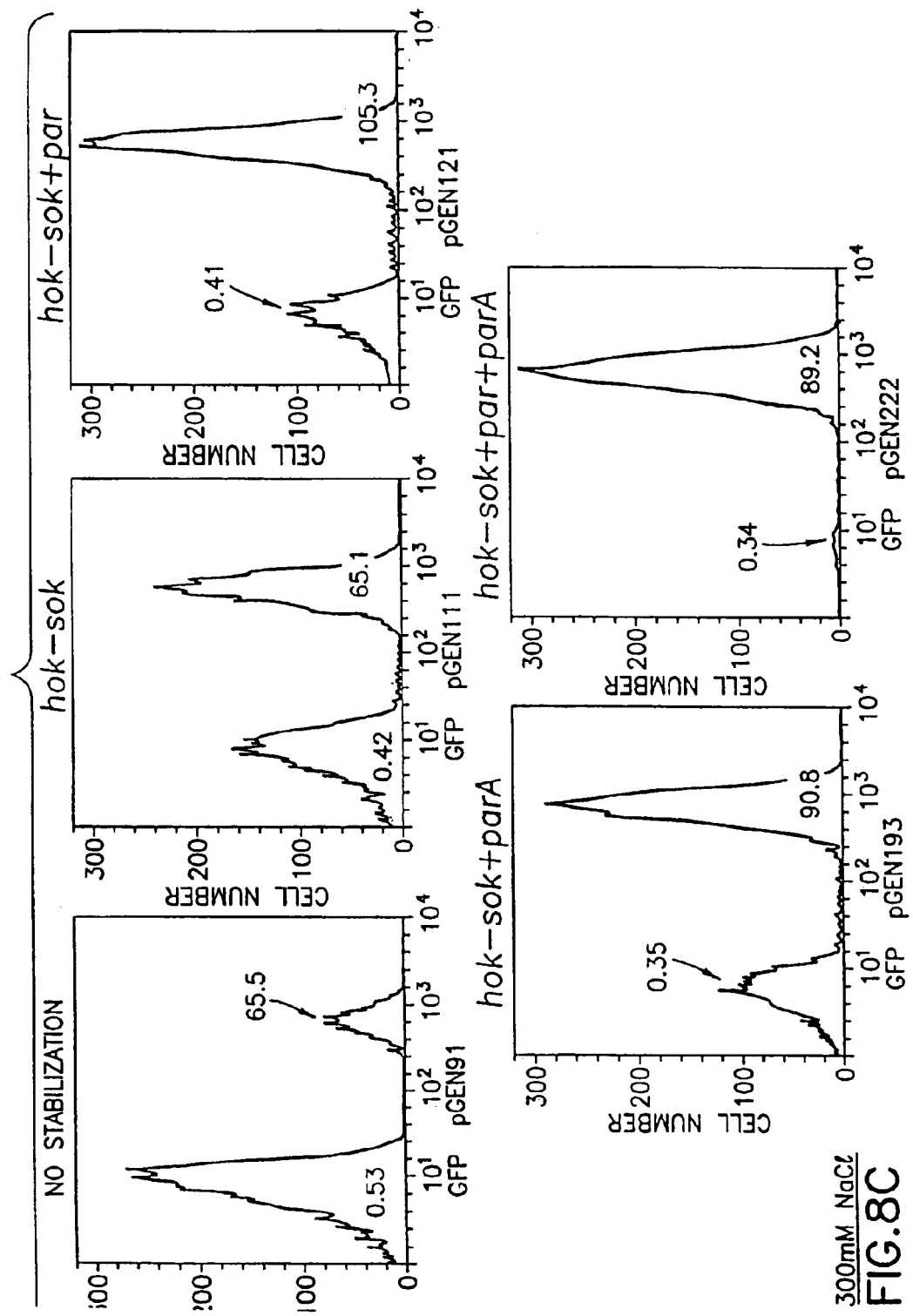
FIG. 8C 300mM NaCl

SEQUENCE LISTING

```
<160> NUMBER OF SEQ ID NOS: 40

<210> SEQ ID NO 1
<211> LENGTH: 4196
<212> TYPE: DNA
<213> ORGANISM: Artificial Sequence
<220> FEATURE:
<223> OTHER INFORMATION: Complete nucleotide sequence of pGEN2

<400> SEQUENCE: 1
gaattctgtg gtagcacaga ataatgaaaa gtgtgtaaag aagggtaaaa aaaaccgaat      60
gcgaggcatc cggttgaaat aggggtaaac agacattcag aaatgaatga cggtaataaa     120
taaagttaat gatgatagcg ggagttattc tagttgcgag tgaaggtttt gttttgacat     180
tcagtgctgt caaatactta agaataagtt attgatttta accttgaatt attattgctt     240
gatgttaggt gcttatttcg ccattccgca ataatcttaa aaagttccct tgcatttaca     300
ttttgaaaca tctatagcga taaatgaaac atcttaaaag ttttagtatc atattcgtgt     360
tggattattc tgcattttg gggagaatgg acttgccgac tgattaatga gggttaatca     420
gtatgcagtg gcataaaaaa gcaaataaag gcatataaca gatcgatctt aaacatccac     480
aggaggatat ctgatgagta aaggagaaga acttttcact ggagttgtcc caattcttgt     540
tgaattagat ggtgatgtta atgggcacaa attttctgtc agtggagagg gtgaaggtga     600
tgcaacatac ggaaaactta cccttaaatt tatttgcact actggaaaac tacctgttcc     660
atggccaaca cttgtcacta ctttctctta tggtgttcaa tgcttttccc gttatccgga     720
tcatatgaaa cggcatgact ttttcaagag tgccatgccc gaaggttatg tacaggaacg     780
cactatatct ttcaaagatg acgggaacta caagacgcgt gctgaagtca agtttgaagg     840 tgatacccctt gttaatcgta tcgagttaaa aggtattgat tttaaagaag atggaaacat     900
tctcggacac aaactcgagt acaactataa ctcacacaat gtatacatca cggcagacaa     960
acaaaagaat ggaatcaaag ctaacttcaa aattcgccac aacattgaag atggatccgt    1020
tcaactagca gaccattatc aacaaaatac tccaattggc gatggccctg tcctttacc    1080 agacaaccat tacctgtcga cacaatctgc cctttcgaaa gatcccaacg aaaagcgtga    1140
ccacatggtc cttcttgagt ttgtaactgc tgctgggatt acacatggca tggatgagct    1200
ctacaaataa tgagctagcc cgcctaatga gcgggctttt ttttctcggc ctagggccag    1260
caaaaggcca ggaaccgtaa aaaggccgcg ttgctggcgt ttttccatag gctccgcccc    1320
```

```
cctgacgagc atcacaaaaa tcgacgctca agtcagaggt ggcgaaaccc gacaggacta   1380
taaagatacc aggcgtttcc ccctggaagc tccctcgtgc gctctcctgt tccgaccctg   1440
ccgcttaccg gatacctgtc cgcctttctc ccttcgggaa gcgtggcgct ttctcatagc   1500
tcacgctgta ggtatctcag ttcggtgtag gtcgttcgct ccaagctggg ctgtgtgcac   1560
gaaccccccg ttcagcccga ccgctgcgcc ttatccggta actatcgtct tgagtccaac   1620
ccggtaagac acgacttatc gccactggca gcagccactg gtaacaggat tagcagagcg   1680
aggtatgtag gcggtgctac agagttcttg aagtggtggc ctaactacgg ctacactaga   1740
aggacagtat ttggtatctg cgctctgctg aagccagtta ccttcggaaa aagagttggt   1800
agctcttgat ccggcaaaca aaccaccgct ggtagcggtg gtttttttgt ttgcaagcag   1860
cagattacgc gcagaaaaaa aggatctcaa gaagatcctt tgatcttttc tacgggtct   1920 gacgctcagt agatctaaaa cactaggccc aagagtttgt agaaacgcaa aaaggccatc   1980
cgtcaggatg gccttctgct taatttgatg cctggcagtt tatggcgggc gtcctgcccg   2040
ccaccctccg ggccgttgct tcgcaacgtt caaatccgct cccggcggat ttgtcctact   2100
caggagagcg ttcaccgaca acaacagat aaaacgaaag gcccagtctt tcgactgagc   2160 cttttcgtttt atttgatgcc tggcagttcc ctactctcgc atggggagac cccacactac   2220
catcggcgct acgcgtttc acttctgagt tcggcatggg gtcaggtggg accaccgcgc   2280
tactgccgcc aggcaaattc tgttttatca gaccgcttct gcgttctgat ttaatctgta   2340
tcaggctgaa aatcttctct catccgccaa acagccaag ctggatcccc gatcttatca    2400
ggtcgaggtg gcccggctcc atgcaccgcg acgcaacgcg gggaggcaga caagtatag    2460 ggcggcgcct acaatccatg ccaacccgtt ccatgtgctc gccgaggcgg cataaatcgc    2520
cgtgacgatc agcggtccag tgatcgaagt taggctggta agagccgcga gcgatccttg    2580
aagctgtccc tgatggtcgt catctacctg cctggacagc atggcctgca acgcgggcat    2640
cccgatgccg ccggaagcga aagaatcat aatggggaag gccatccagc ctcgcgtcgc    2700
gaacgccagc aagacgtagc ccagcgcgtc ggccgccatg ccggcgataa tggcctgctt    2760
ctcgccgaaa cgtttggtgg cgggaccagt gacgaaggct tgagcgaggg cgtgcaagat    2820
tccgaatacc gcaagcgaca ggccgatcat cgtcgcgctc cagcgaaagc ggtcctcgcc    2880
gaaaatgacc cagagcgctg ccggcacctg tcctacgagt tgcatgataa agaagacagt    2940
cataagtgcg gcgacgatag tcatgccccg cgcccaccgg aaggagctga ctgggttgaa    3000
ggctctcaag ggcatcggtc gacgctctcc cttatgcgac tcctgcatta ggaagcagcc    3060
cagtagtagg ttgaggccgt tgagcaccgc cgccgcaagg aatggtgcat gcaaggagat    3120
ggcgcccaac agtcccccgg ccacggggcc tgccaccata cccacgccga aacaagcgct    3180
catgagcccg aagtggcgag cccgatcttc cccatcggtg atgtcggcga tataggcgcc    3240
agcaaccgca cctgtggcgc cggtgatgcc ggccacgatg cgtccggcgt agaggatcca    3300
caggacgggt gtggtcgcca tgatcgcgta gtcgatagtg gctccaagta gcgaagcgag    3360
caggactggg cggcggccaa agcggtcgga cagtgctccg agaacgggtg cgcatagaaa    3420
ttgcatcaac gcatatagcg ctagcagcac gccatagtga ctggcgatgc tgtcggaatg    3480
gacgatatcc cgcaagaggc ccggcagtac cggcataacc aagcctatgc ctacagcatc    3540
cagggtgacg gtgccgagga tgacgatgag cgcattgtta gatttcattt ttttttcctc    3600
cttattttct agcaacatc agcaaggaga aaggggctac cggcgaacca gcagcccctt    3660
tataaaggcg cttcagtagt cagaccagca tcagtcctga aaaggcgggc ctgcgcccgc    3720
```

-continued

```
ctccaggttg ctacttaccg gattcgtaag ccatgaaagc cgccacctcc ctgtgtccgt   3780
ctctgtaacg aatctcgcac agcgattttc gtgtcagata agtgaatatc aacagtgtga   3840
gacacacgat caacacacac cagacaaggg aacttcgtgg tagtttcatg gccttcttct   3900
ccttgcgcaa agcgcggtaa gaggctatcc tgatgtggac tagacatagg gatgcctcgt   3960
ggtggttaat gaaaattaac ttactacggg gctatcttct ttctgccaca caacacggca   4020
acaaaccacc ttcacgtcat gaggcagaaa gcctcaagcg ccgggcacat catagcccat   4080
atacctgcac gctgaccaca ctcactttcc ctgaaaataa tccgctcatt cagaccgttc   4140
acgggaaatc cgtgtgattg ttgccgcatc acgctgcctc ccggagtttg tctcga       4196
```

<210> SEQ ID NO 2
<211> LENGTH: 1197
<212> TYPE: DNA
<213> ORGANISM: Artificial Sequence
<220> FEATURE:
<223> OTHER INFORMATION: Partial nucleotide sequence of pGEN3:
      nucleotides 1201-2397 encoding ori15A

<400> SEQUENCE: 2

```
ctacaaataa tgagctagcc cgcctaatga gcgggctttt ttttctcggc ctaggagata     60
cttaacaggg aagtgagagg gccgcggcaa agccgttttt ccataggctc cgccccctg    120 acaagcatca cgaaatctga cgctcaaatc agtggtggcg aaacccgaca ggactataaa   180
gataccaggc gtttccccct ggcggctccc tcgtgcgctc tcctgttcct gcctttcggt   240
ttaccggtgt cattccgctg ttatggccgc gtttgtctca ttccacgcct gacactcagt   300
tccgggtagg cagttcgctc caagctggac tgtatgcacg aaccccccgt tcagtccgac   360
cgctgcgcct tatccggtaa ctatcgtctt gagtccaacc cggaaagaca tgcaaaagca   420
ccactggcag cagccactgg taattgattt agaggagtta gtcttgaagt catgcgccgg   480
ttaaggctaa actgaaagga caagttttgg tgactgcgct cctccaagcc agttacctcg   540
gttcaaagag ttggtagctc agagaacctt cgaaaaaccg ccctgcaagg cggttttttc   600
gttttcagag caagagatta cgcgcagacc aaaacgatct caagaagatc atcttattaa   660
tcagataaaa tatttctagg atctaaaaca ctaggcccaa gagtttgtag aaacgcaaaa   720
aggccatccg tcaggatggc cttctgctta atttgatgcc tggcagttta tggcgggcgt   780
cctgcccgcc accctccggg ccgttgcttc gcaacgttca aatccgctcc cggcggattt   840
gtcctactca ggagagcgtt caccgacaaa caacagataa acgaaaggc ccagtctttc    900 gactgagcct tcgtttttat ttgatgcctg gcagttccct actctcgcat ggggagaccc   960
cacactacca tcggcgctac ggcgtttcac ttctgagttc ggcatggggt caggtgggac  1020
caccgcgcta ctgccgccag gcaaattctg ttttatcaga ccgcttctgc gttctgattt  1080
aatctgtatc aggctgaaaa tcttctctca tccgccaaaa cagccaagct ggatcccga   1140 tcttatcagg tcgaggtggc ccggctccat gcaccgcgac gcaacgcggg gaggcag     1197
```

<210> SEQ ID NO 3
<211> LENGTH: 2647
<212> TYPE: DNA
<213> ORGANISM: Artificial Sequence
<220> FEATURE:
<223> OTHER INFORMATION: Partial nucleotide sequence of pGEN4:
      nucleotides 1201-3848 encoding ori101

<400> SEQUENCE: 3

-continued

| | |
|---|---|
| ctacaaataa tgagctagcc cgcctaatga gcgggctttt ttttctcggc ctaggtttca | 60 |
| cctgttctat taggtgttac atgctgttca tctgttacat tgtcgatctg ttcatggtga | 120 |
| acagctttaa atgcaccaaa aactcgtaaa agctctgatg tatctatctt ttttacaccg | 180 |
| ttttcatctg tgcatatgga cagttttccc tttgatatct aacggtgaac agttgttcta | 240 |
| cttttgtttg ttagtcttga tgcttcactg atagatacaa gagccataag aacctcagat | 300 |
| ccttccgtat ttagccagta tgttctctag tgtggttcgt tgttttttgcg tgagccatga | 360 |
| gaacgaacca ttgagatcat gcttactttg catgtcactc aaaaattttg cctcaaaact | 420 |
| ggtgagctga attttttgcag ttaaagcatc gtgtagtgtt tttcttagtc cgttacgtag | 480 |
| gtaggaatct gatgtaatgg ttgttggtat tttgtcacca ttcattttta tctggttgtt | 540 |
| ctcaagttcg gttacgagat ccatttgtct atctagttca acttggaaaa tcaacgtatc | 600 |
| agtcgggcgg cctcgcttat caaccaccaa tttcatattg ctgtaagtgt ttaaatcttt | 660 |
| acttattggt ttcaaaaccc attggttaag ccttttaaac tcatggtagt tattttcaag | 720 |
| cattaacatg aacttaaatt catcaaggct aatctctata tttgccttgt gagttttctt | 780 |
| ttgtgttagt tcttttaata accactcata aatcctcata gagtatttgt tttcaaaaga | 840 |
| cttaacatgt tccagattat attttatgaa ttttttttaac tggaaaagat aaggcaatat | 900 |
| ctcttcacta aaactaatt ctaatttttc gcttgagaac ttggcatagt ttgtccactg | 960 |
| gaaaatctca aagcctttaa ccaaaggatt cctgatttcc acagttctcg tcatcagctc | 1020 |
| tctggttgct ttagctaata caccataagc attttcccta ctgatgttca tcatctgagc | 1080 |
| gtattggtta taagtgaacg ataccgtccg ttctttcctt gtagggtttt caatcgtggg | 1140 |
| gttgagtagt gccacacagc ataaaattag cttggtttca tgctccgtta agtcatagcg | 1200 |
| actaatcgct agttcatttg ctttgaaaac aactaattca gacatacatc tcaattggtc | 1260 |
| taggtgattt taatcactat accaattgag atgggctagt caatgataat tactagtcct | 1320 |
| tttcctttga gttgtgggta tctgtaaatt ctgctagacc tttgctggaa aacttgtaaa | 1380 |
| ttctgctaga ccctctgtaa attccgctag acctttgtgt gttttttttg tttatattca | 1440 |
| agtggttata atttatagaa taaagaaaga ataaaaaaag ataaaaagaa tagatcccag | 1500 |
| ccctgtgtat aactcactac tttagtcagt tccgcagtat tacaaaagga tgtcgcaaac | 1560 |
| gctgtttgct cctctacaaa acagaccttaa aaccctaaa ggcttaagta gcaccctcgc | 1620 |
| aagctcgggc aaatcgctga atattccttt tgtctccgac catcaggcac ctgagtcgct | 1680 |
| gtcttttcg tgacattcag ttcgctgcgc tcacggctct ggcagtgaat gggggtaaat | 1740 |
| ggcactacag gcgccttttta tggattcatg caaggaaact acccataata caagaaaagc | 1800 |
| ccgtcacggg cttctcaggg cgttttatgg cgggtctgct atgtggtgct atctgacttt | 1860 |
| ttgctgttca gcagttcctg ccctctgatt ttccagtctg accacttcgg attatcccgt | 1920 |
| gacaggtcat tcagactggc taatgcaccc agtaaggcag cggtatcatc aacaggctta | 1980 |
| cccgtcttac tgtcaaccgg atctaaaaca ctaggcccaa gagtttgtag aaacgcaaaa | 2040 |
| aggccatccg tcaggatggc cttctgctta atttgatgcc tggcagttta tggcgggcgt | 2100 |
| cctgcccgcc accctccggg ccgttgcttc gcaacgttca aatccgctcc cggcggattt | 2160 |
| gtcctactca ggagagcgtt caccgacaaa caacagataa acgaaaggc ccagtctttc | 2220 |
| gactgagcct ttcgttttat ttgatgcctg gcagttccct actctcgcat ggggagaccc | 2280 |
| cacactacca tcggcgctac ggcgtttcac ttctgagttc ggcatggggt caggtgggac | 2340 |
| caccgcgcta ctgccgccag gcaaattctg ttttatcaga ccgcttctgc gttctgattt | 2400 |

```
aatctgtatc aggctgaaaa tcttctctca tccgccaaaa cagccaagct ggatccccga      2460
tcttatcagg tcgaggtggc ccggctccat gcaccgcgac gcaacgcggg gaggcagaca      2520
aggtataggg cggcgcctac aatccatgcc aacccgttcc atgtgctcgc cgaggcggca      2580
taaatcgccg tgacgatcag cggtccagtg atcgaagtta ggctggtaag agccgcgagc      2640
gatcctt                                                                2647

<210> SEQ ID NO 4
<211> LENGTH: 41
<212> TYPE: DNA
<213> ORGANISM: Artificial Sequence
<220> FEATURE:
<223> OTHER INFORMATION: Portion of promoter sequence

<400> SEQUENCE: 4
catataacag atcttaatca tccacaggag gatatctgat g                          41

<210> SEQ ID NO 5
<211> LENGTH: 45
<212> TYPE: DNA
<213> ORGANISM: Artificial Sequence
<220> FEATURE:
<223> OTHER INFORMATION: Portion of promoter sequence

<400> SEQUENCE: 5
catataacag atcgatctta aacatccaca ggaggatatc tgatg                      45

<210> SEQ ID NO 6
<211> LENGTH: 66
<212> TYPE: DNA
<213> ORGANISM: Artificial Sequence
<220> FEATURE:
<223> OTHER INFORMATION: Primer

<400> SEQUENCE: 6
gaattcgcgc gcttcgcgat tcagtcgcgt tccttcacag ctggcgcagg ggcgattact      60
gatgaa                                                                 66

<210> SEQ ID NO 7
<211> LENGTH: 66
<212> TYPE: DNA
<213> ORGANISM: Artificial Sequence
<220> FEATURE:
<223> OTHER INFORMATION: Primer

<400> SEQUENCE: 7
cccgggagtc tcctgaatac gtttcataaa tagtgtaaac gcgtgagtgt accatttcca      60
cgtagc                                                                 66

<210> SEQ ID NO 8
<211> LENGTH: 69
<212> TYPE: DNA
<213> ORGANISM: Artificial Sequence
<220> FEATURE:
<223> OTHER INFORMATION: Primer

<400> SEQUENCE: 8
cccgggtaaa aaactcaaag cgttatttgc attttcgcta tagttctcgt ctgctgaaat      60
gcctggtgt                                                              69

<210> SEQ ID NO 9
```

```
<211> LENGTH: 77
<212> TYPE: DNA
<213> ORGANISM: Artificial Sequence
<220> FEATURE:
<223> OTHER INFORMATION: Primer

<400> SEQUENCE: 9
gaattccatt tctatcaata aattactatt agttttgtct tctaaccaag cctctatttt      60
atgagtatcc tcttcag                                                    77

<210> SEQ ID NO 10
<211> LENGTH: 72
<212> TYPE: DNA
<213> ORGANISM: Artificial Sequence
<220> FEATURE:
<223> OTHER INFORMATION: Primer

<400> SEQUENCE: 10
gctagcatgg ccagcagagg cgtaaacaag gtgattctcg ttggtaatct gggccaggac      60
ccggaagtac gc                                                         72

<210> SEQ ID NO 11
<211> LENGTH: 64
<212> TYPE: DNA
<213> ORGANISM: Artificial Sequence
<220> FEATURE:
<223> OTHER INFORMATION: Primer

<400> SEQUENCE: 11
gctagctcag aacggaatgt cgtcgtcaaa atccattggc ggttcgttag acggcgctgg      60
cgcg                                                                  64

<210> SEQ ID NO 12
<211> LENGTH: 45
<212> TYPE: DNA
<213> ORGANISM: Artificial Sequence
<220> FEATURE:
<223> OTHER INFORMATION: Primer

<400> SEQUENCE: 12
gcaggaaaga acatgtgagc ctagggccag caaaaggcca ggaac                     45

<210> SEQ ID NO 13
<211> LENGTH: 53
<212> TYPE: DNA
<213> ORGANISM: Artificial Sequence
<220> FEATURE:
<223> OTHER INFORMATION: Primer

<400> SEQUENCE: 13
catgaccaaa atcccttaac tagtgtttta gatctactga gcgtcagacc ccg            53

<210> SEQ ID NO 14
<211> LENGTH: 53
<212> TYPE: DNA
<213> ORGANISM: Artificial Sequence
<220> FEATURE:
<223> OTHER INFORMATION: Primer

<400> SEQUENCE: 14
cggggtctga cgctcagtag atctaaaaca ctagttaagg gattttggtc atg            53

<210> SEQ ID NO 15
<211> LENGTH: 49
```

```
<212> TYPE: DNA
<213> ORGANISM: Artificial Sequence
<220> FEATURE:
<223> OTHER INFORMATION: Primer

<400> SEQUENCE: 15
gctgtcaaac atgagaattc tagaagacga aagggcctcg tgatacgcc            49

<210> SEQ ID NO 16
<211> LENGTH: 64
<212> TYPE: DNA
<213> ORGANISM: Artificial Sequence
<220> FEATURE:
<223> OTHER INFORMATION: Primer

<400> SEQUENCE: 16
acagcctgca gacagatctt gacagctgga tcgcactctg gtataattgg gaagccctgc    60
aaag                                                             64

<210> SEQ ID NO 17
<211> LENGTH: 59
<212> TYPE: DNA
<213> ORGANISM: Artificial Sequence
<220> FEATURE:
<223> OTHER INFORMATION: Primer

<400> SEQUENCE: 17
cgaagcccaa cctttcatag aagctagcgg tggatccgaa atctcgtgat ggcaggttg     59

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
aacaagcgtt ataggaattc tgtggtagca                                 30

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
actttcatgt tattaaagat ctgttatatg                                 30

<210> SEQ ID NO 20
<211> LENGTH: 59
<212> TYPE: DNA
<213> ORGANISM: Artificial Sequence
<220> FEATURE:
<223> OTHER INFORMATION: Primer

<400> SEQUENCE: 20
agatcttaat catccacagg aggctttctg atgagtaaag gagaagaact tttcactgg     59

<210> SEQ ID NO 21
<211> LENGTH: 32
<212> TYPE: DNA
<213> ORGANISM: Artificial Sequence
<220> FEATURE:
<223> OTHER INFORMATION: Primer
```

```
<400> SEQUENCE: 21
gctagctcat tatttgtaga gctcatccat gc                                32

<210> SEQ ID NO 22
<211> LENGTH: 54
<212> TYPE: DNA
<213> ORGANISM: Artificial Sequence
<220> FEATURE:
<223> OTHER INFORMATION: Primer

<400> SEQUENCE: 22
agatctgaat tctagatcat gtttgacagc ttatcatcga taagctttaa tgcg        54

<210> SEQ ID NO 23
<211> LENGTH: 51
<212> TYPE: DNA
<213> ORGANISM: Artificial Sequence
<220> FEATURE:
<223> OTHER INFORMATION: Primer

<400> SEQUENCE: 23
agatcttatc aggtcgaggt ggcccggctc catgcaccgc gacgcaacgc g            51

<210> SEQ ID NO 24
<211> LENGTH: 61
<212> TYPE: DNA
<213> ORGANISM: Artificial Sequence
<220> FEATURE:
<223> OTHER INFORMATION: Primer

<400> SEQUENCE: 24
cgcgaattct cgagacaaac tccgggaggc agcgtgatgc ggcaacaatc acacggattt  60
c                                                                  61

<210> SEQ ID NO 25
<211> LENGTH: 69
<212> TYPE: DNA
<213> ORGANISM: Artificial Sequence
<220> FEATURE:
<223> OTHER INFORMATION: Primer

<400> SEQUENCE: 25
atgagcgcat tgttagattt catttttttt tcctccttat tttctagaca acatcagcaa  60
ggagaaagg                                                          69

<210> SEQ ID NO 26
<211> LENGTH: 69
<212> TYPE: DNA
<213> ORGANISM: Artificial Sequence
<220> FEATURE:
<223> OTHER INFORMATION: Primer

<400> SEQUENCE: 26
cctttctcct tgctgatgtt gtctagaaaa taaggaggaa aaaaaatga atctaacaa    60 tgcgctcat                                                          69

<210> SEQ ID NO 27
<211> LENGTH: 65
<212> TYPE: DNA
<213> ORGANISM: Artificial Sequence
<220> FEATURE:
<223> OTHER INFORMATION: Primer

<400> SEQUENCE: 27
```

```
gctacatttg aagagataaa ttgcactgga tcctagaaat attttatctg attaataaga      60
tgatc                                                                 65

<210> SEQ ID NO 28
<211> LENGTH: 50
<212> TYPE: DNA
<213> ORGANISM: Artificial Sequence
<220> FEATURE:
<223> OTHER INFORMATION: Primer

<400> SEQUENCE: 28
cggagatttc ctggaagatg cctaggagat acttaacagg gaagtgagag              50

<210> SEQ ID NO 29
<211> LENGTH: 61
<212> TYPE: DNA
<213> ORGANISM: Artificial Sequence
<220> FEATURE:
<223> OTHER INFORMATION: Primer

<400> SEQUENCE: 29
gtctgccgga ttgcttatcc tggcggatcc ggttgacagt aagacgggta agcctgttga      60
t                                                                     61

<210> SEQ ID NO 30
<211> LENGTH: 61
<212> TYPE: DNA
<213> ORGANISM: Artificial Sequence
<220> FEATURE:
<223> OTHER INFORMATION: Primer

<400> SEQUENCE: 30
cctaggtttc acctgttcta ttaggtgtta catgctgttc atctgttaca ttgtcgatct      60
g                                                                     61

<210> SEQ ID NO 31
<211> LENGTH: 61
<212> TYPE: DNA
<213> ORGANISM: Artificial Sequence
<220> FEATURE:
<223> OTHER INFORMATION: Primer

<400> SEQUENCE: 31
aggcttaagt agcaccctcg caagatctgg caaatcgctg aatattcctt ttgtctccga      60
c                                                                     61

<210> SEQ ID NO 32
<211> LENGTH: 70
<212> TYPE: DNA
<213> ORGANISM: Artificial Sequence
<220> FEATURE:
<223> OTHER INFORMATION: Primer

<400> SEQUENCE: 32
gagggcgccc cagctggcaa ttctagactc gagcactttt gttacccgcc aaacaaaacc      60
caaaacaac                                                             70

<210> SEQ ID NO 33
<211> LENGTH: 61
<212> TYPE: DNA
<213> ORGANISM: Artificial Sequence
<220> FEATURE:
```

<223> OTHER INFORMATION: Primer

<400> SEQUENCE: 33
agaagaaaaa tcgaattcca gcatgaagag tttcagaaaa tgacagagcg tgagcaagtg    60
c                                                                   61

<210> SEQ ID NO 34
<211> LENGTH: 59
<212> TYPE: DNA
<213> ORGANISM: Artificial Sequence
<220> FEATURE:
<223> OTHER INFORMATION: Primer

<400> SEQUENCE: 34
cgaagcccaa cctttcatag aaactagtgg tggaatcgaa atctcgtgat ggcaggttg    59

<210> SEQ ID NO 35
<211> LENGTH: 70
<212> TYPE: DNA
<213> ORGANISM: Artificial Sequence
<220> FEATURE:
<223> OTHER INFORMATION: Primer

<400> SEQUENCE: 35 gttgttttg ggttttgttt ggcgggtaac aaaagtgctc gagtctagaa ttgccagctg     60
gggcgccctc                                                           70

<210> SEQ ID NO 36
<211> LENGTH: 34
<212> TYPE: DNA
<213> ORGANISM: Artificial Sequence
<220> FEATURE:
<223> OTHER INFORMATION: Modified Promoter Sequence
<220> FEATURE:
<221> NAME/KEY: misc_feature
<222> LOCATION: (6)..(6)
<223> OTHER INFORMATION: "n" may be G, C or A
<220> FEATURE:
<221> NAME/KEY: misc_feature
<222> LOCATION: (7)..(7)
<223> OTHER INFORMATION: "n" is an insert of 1 to 5 nucleotides selected
      from A, C, G and T
<220> FEATURE:
<221> NAME/KEY: misc_feature
<222> LOCATION: (11)..(11)
<223> OTHER INFORMATION: "n" is A, C, G or T

<400> SEQUENCE: 36
agatcnntaa ncatccacag gaggatatct gatg                               34

<210> SEQ ID NO 37
<211> LENGTH: 15
<212> TYPE: DNA
<213> ORGANISM: Artificial Sequence
<220> FEATURE:
<223> OTHER INFORMATION: Modified Shiga toxin sequence

<400> SEQUENCE: 37
acagcagacg cgtta                                                    15

<210> SEQ ID NO 38
<211> LENGTH: 15
<212> TYPE: DNA
<213> ORGANISM: Artificial Sequence
<220> FEATURE:
<223> OTHER INFORMATION: Modified Shiga toxin sequence

```
<400> SEQUENCE: 38
ctgaacctag ggcga                                                         15

<210> SEQ ID NO 39
<211> LENGTH: 15
<212> TYPE: DNA
<213> ORGANISM: Artificial Sequence
<220> FEATURE:
<223> OTHER INFORMATION: Modified Shiga toxin sequence

<400> SEQUENCE: 39
gaattcgcga ccagt                                                         15

<210> SEQ ID NO 40
<211> LENGTH: 15
<212> TYPE: DNA
<213> ORGANISM: Artificial Sequence
<220> FEATURE:
<223> OTHER INFORMATION: Modified Shiga toxin sequence

<400> SEQUENCE: 40
gaatcagatt ctgga                                                         15
```

PLASMID MAINTENANCE SYSTEM FOR ANTIGEN DELIVERY

CROSS-REFERENCE TO RELATED APPLICATIONS

This Application is a Divisional of application Ser. No. 09/453,313, filed Dec. 2, 1999, now U.S. Pat. No. 6,703,233, which is a Continuation-in-Part Apllication of U.S. application Ser. No. 09/204,117, filed Dec. 2, 1998 (now U.S. Pat. No. 6,413,768), and also claims priority to U.S. Provisional Application No. 60/158,738, filed Oct. 12, 1999; the above noted prior applications are all hereby incorporated by reference.

STATEMENT OF GOVERNMENT INTEREST

This invention was made with support pursuant to National Institutes of Health Grant No. RO1 A129471. The government may have certain rights in this invention.

1. BACKGROUND OF THE INVENTION

1.1 Field of the Invention

The present invention relates generally to expression plasmids stabilized by a Plasmid Maintenance System (as defined herein) capable of expressing a protein or peptide, such as an antigen for use in a live vector vaccine, and methods for making and using the stabilized plasmids. The invention optimizes the maintenance of expression plasmids at two independent levels by: (1) removing sole dependence on catalytic balanced lethal maintenance systems; and (2) incorporating a plasmid partition system to prevent random segregation of expression plasmids, thereby enhancing inheritance and stability.

1.2 Description of Related Art

Set forth below is a discussion of art relevant to the present invention.

1.2.1 Bacterial Live Vector Vaccines

Bacterial live vector vaccines deliver antigens to a host immune system by expressing the antigens from genetic material contained within a bacterial live vector. The genetic material is typically a replicon, such as a plasmid. The antigens may include a wide variety of proteins and/or peptides of bacterial, viral, parasitic or other origin.

Among the bacterial live vectors currently under investigation are attenuated enteric pathogens (e.g., *Salmonella typhi, Shigella, Vibrio cholerae*), commensals (e.g., *Lactobacillus, Streptococcus gordonii*) and licensed vaccine strains (e.g., BCG). *S. typhi* is a particularly attractive strain for human vaccination.

1.2.2 Attenuated *Salmonella typhi* as a Live Vector Strain

*S. typhi* is a well-tolerated live vector that can deliver multiple unrelated immunogenic antigens to the human immune system. *S. typhi* live vectors have been shown to elicit antibodies and a cellular immune response to an expressed antigen. Examples of antigens successfully delivered by *S. typhi* include the non-toxigenic yet highly immunogenic fragment C of tetanus toxin and the malaria circumsporozoite protein from *Plasmodium falciparum*.

*S. typhi* is characterized by enteric routes of infection, a quality which permits oral vaccine delivery. *S. typhi* also infects monocytes and macrophages and can therefore target antigens to professional APCs.

Expression of an antigen by *S. typhi* generally requires incorporation of a recombinant plasmid encoding the antigen. Consequently, plasmid stability is a key factor in the development of high quality attenuated *S. typhi* vaccines with the ability to consistently express foreign antigens.

Attenuated *S. typhi* vaccine candidates for use in humans should possess at least two well separated and well defined mutations that independently cause attenuation, since the chance of in vivo reversion of such double mutants would be negligible. The attenuated vaccine candidate *S. typhi* CVD908 possesses such properties. CVD908 contains two non-reverting deletion mutations within the aroC and aroD genes. These two genes encode enzymes critical in the biosynthetic pathway leading to synthesis of chorismate, the key precursor required for synthesis of the aromatic amino acids phenylalanine, tyrosine, and tryptophan. Chorismate is also required for the synthesis of p-aminobenzoic acid; after its conversion to tetrahydrofolate, p-aminobenzoic acid is converted to the purine nucleotides ATP and GTP.

1.2.3 Plasmid Instability

Plasmidless bacterial cells tend to accumulate more rapidly than plasmid-bearing cells. One reason for this increased rate of accumulation is that the transcription and translation of plasmid genes imposes a metabolic burden which slows cell growth and gives plasmidless cells a competitive advantage. Furthermore, foreign plasmid gene products are sometimes toxic to the host cell.

Stable inheritance of plasmids is desirable in the field of attenuated bacterial live vector vaccines to ensure successful continued antigen production, as well as in commercial bioreactor operations in order to prevent bioreactor takeover by plasmidless cells.

Stable inheritance of a plasmid generally requires that: (1) the plasmid must replicate once each generation, (2) copy number deviations must be rapidly corrected before cell division, and (3) upon cell division, the products of plasmid replication must be distributed to both daughter cells.

Although chromosomal integration of foreign genes increases the stability of such sequences, the genetic manipulations involved can be difficult, and the drop in copy number of the heterologous gene often results in production of insufficient levels of heterologous antigen to ensure an optimal immune response. Introduction of heterologous genes onto multicopy plasmids maintained within a live vector strain is a natural solution to the copy number problem; genetic manipulation of such plasmids for controlled expression of such heterologous genes is straightforward. However, resulting plasmids can become unstable in vivo, resulting in loss of these foreign genes.

1.2.4 Plasmid Stabilization Systems

In nature bacterial plasmids are often stably maintained, even though usually present at very low copy numbers. Stable inheritance of naturally occurring lower copy number plasmids can depend on the presence of certain genetic systems which actively prevent the appearance of plasmid-free progeny. A recent review of plasmid maintenance systems can be found in Jensen et al. *Molecular Microbiol.* 17:205–210, 1995 (incorporated herein by reference).

1.2.5 Antibiotic Resistance

One means for maintaining plasmids is to provide an antibiotic resistance gene on the plasmid and to grow the cells in antibioticenriched media. However, this method is subject to a number of difficulties. The antibiotic resistance approach is expensive, requiring the use of costly antibiotics and, perhaps more importantly, the use of antibiotics in conjunction with in vivo administration of vaccine vectors is currently discouraged by the U.S. Food and Drug Administration.

In large-scale production applications, the use of antibiotics may impose other limitations. With respect to commercial bioreactors, antibiotic resistance mechanisms can degrade the antibiotic and permit a substantial population of plasmidless cells to persist in the culture. Such plasmidless cells are unproductive and decrease the output of the bioreactor.

There is therefore a need in the art for a plasmid maintenance system specifically designed for use in bacterial live vector vaccines which does not rely on antibiotic resistance, and preferably which is also useful in commercial bioreactor applications.

1.2.6 Segregational Plasmid Maintenance Functions

Stable lower copy number plasmids typically employ a partitioning function that actively distributes plasmid copies between daughter cells. Exemplary partitioning functions include, without limitation, systems of pSC101, the F factor, the P1 prophage, and incFII drug resistance plasmids. Such functions are referred to herein as "SEG" functions.

1.2.7 Post-Segregational Killing (PSK) Functions

Naturally occurring PSK plasmid maintenance functions typically employ a two component toxin-antitoxin system and generally operate as follows: The plasmid encodes both a toxin and an antitoxin. The antitoxins are less stable than the toxins, which tend to be quite stable. In a plasmidless daughter cell, the toxins and anti-toxins are no longer being produced; however, the less stable antitoxins quickly degrade, thereby freeing the toxin to kill the cell.

The toxins are generally small proteins and the antitoxins are either small proteins (proteic systems such as phd-doc) or antisense RNAs which bind to the toxin-encoding mRNAs preventing their synthesis (antisense systems such as hok-sok).

Balanced lethal systems discussed below in Section 1.2.7.3 are an example of an artificial PSK function.

1.2.7.1 Proteic Maintenance System: The phd-doc System

In proteic PSK functions, both the toxin and antitoxin are synthesized from operons in which the gene encoding the antitoxin is upstream of the gene encoding the toxin. These operons autoregulate transcription levels, and synthesis of the encoded proteins is translationally coupled. The antitoxin is generally synthesized in excess to ensure that toxin action is blocked. The unstable antitoxins are constantly degraded by host-encoded proteases, requiring constant synthesis of antitoxin to protect the cell. Upon loss of the plasmid, antitoxins are no longer produced, and the existing antitoxins rapidly degrade, permitting the toxin to kill the host cell.

The phd-doc system is an example of a proteic PSK function. The phd-doc system occurs naturally within the temperate bacteriophage P1, which lysogenizes *Escherichia coli*, as an ~100 kb plasmid. This maintenance locus encodes two small proteins: the toxic 126 amino acid Doc protein causes death on curing of the plasmid by an unknown mechanism, and the 73 amino acid Phd antitoxin prevents host death, presumably by binding to and blocking the action of Doc.

Phd and Doc are encoded by a single transcript in which the ATG start codon of the downstream doc gene overlaps by one base the TGA stop codon of the upstream phd gene. Expression of these two proteins is therefore translationally coupled, with Phd synthesis exceeding synthesis of the toxic Doc protein.

In addition, transcription of this operon is autoregulated at the level of transcription through the binding of a Phd-Doc protein complex to a site which blocks access of RNA polymerase to the promoter of the operon as concentrations of both proteins reach a critical level. Although Doc appears to be relatively resistant to proteolytic attack, Phd is highly susceptible to cleavage. The PSK mechanism of a plasmid-encoded phd-doc locus is therefore activated when bacteria spontaneously lose this resident plasmid, leading to degradation of the Phd antitoxin and subsequent activation of the Doc toxin which causes cell death, 1.2.7.2 Antisense Maintenance System: The hok-sok System In antisense maintenance systems, the antitoxins are antisense RNAs that inhibit translation of toxin-encoding mRNAs. Like the antitoxin peptides, the antisense RNAs are less stable than the toxin-encoding mRNA. Loss of the plasmid permits existing antitoxins to degrade, thereby permitting synthesis of the toxin which kills the host cell.

An example of an antisense maintenance system is the hok-sok system, encoded by the parB locus of plasmid R1. The system is comprised of three genes: hok, sok and mok.

Hok is a membrane-associated protein which irreversibly damages the cell membrane, killing host cells. Expression of Hok from hok mRNA leads to a loss of cell membrane potential, arrest of respiration, changes in cell morphology, and cell death.

The sok gene encodes a trans-acting RNA which blocks translation of hok mRNA, thereby preventing Hok killing of host cells. The sok RNA is less stable than hok mRNA and is expressed from a relatively weak promoter. (Gerdes et al. *Annu. Rev. Genet.*, 31:1–31, 1997) incorporated herein. The mechanism by which sok RNA blocks translation of Hok in plasmid-containing cells became apparent only after the identification of mok (modulation of killing), a third gene in the parB locus. The mok open reading frame overlaps with hok, and is necessary for expression and regulation of hok translation.

The sok antisense RNA forms a duplex with the 5' end of the mok-hok message rendering the mok ribosome binding site inaccessible to ribosomes and promoting RNase III cleavage and degradation of the mRNA. In the absence of mok translation, hok is not expressed from intact message, even though its own ribosome binding site is not directly obscured by sok RNA.

When a plasmid-free cell is formed, the unstable sok RNA decays much more rapidly than the stable mok-hok message. When the protection afforded by sok is lost, Mok and Hok are translated and the cell dies.

A limitation of the hok-sok system is that a significant number of plasmidless cells can arise when the hok-sok system is inactivated by mutations within the Hok open reading frame.

1.2.7.3 Balanced Lethal Systems

In a balanced-lethal system (a PSK function), a chromosomal gene encoding an essential structural protein or enzyme is deleted from the bacterial chromosome or is mutated such that the gene can no longer operate. The removed or damaged gene is then replaced by a plasmid comprising a fully operating gene. Loss of the plasmid results in an insufficiency of the essential protein and the death of the plasmidless cell.

A balanced-lethal system has been successfully employed in *S. typhimuriun* based on expression of the asd gene encoding aspartate β-semialdehyde dehydrogenase (Asd). Asd is a critical enzyme involved in the synthesis of L-aspartic-β-semialdehyde, which is a precursor essential for the synthesis of the amino acids L-threonine (and L-isoleucine), L-methionine, and L-lysine, as well as diaminopimelic acid, a key structural component essential to the formation of the cell wall in Gram-negative bacteria. Loss of plasmids encoding Asd would be lethal for any bacterium incapable of synthesizing Asd from the chromosome, and would result in lysis of the bacterium due to an inability to correctly assemble the peptidoglycan layer of its cell wall.

The asd system (a PSK function) has been successfully employed in attenuated *S. typhimnunum*-based live vector strains for immunization of mice with a variety of procaryotic and eucaryotic antigens, including such diverse antigens as detoxified tetanus toxin fragment C and the LT enterotoxin, synthetic hepatitis B viral peptides, and gamete-specific antigens such as the human sperm antigen SP10.

Murine mucosal immunization with these live vector strains has elicited significant immune responses involving serum IgG and secretory IgA responses at mucosal surfaces.

The asd system has recently been introduced into attenuated *Salmonella typhi* vaccine strains in an attempt to increase the stability of plasmids expressing synthetic hepatitis B viral peptides.

However, when volunteers were immunized with these live vector strains, no immune response to the foreign antigen was detected.

In fact, to date, very few reports have documented an immune response to plasmid-based expression of a foreign antigen from stabilized plasmids after human vaccination with an attenuated *S. typhi* live vector. In one report, the vaccine strain Ty21a was made auxotrophic for thymine by selecting in the presence of trimethoprim for an undefined mutation in the thyA. gene, encoding thymidylate synthetase.

Although in some cases failure of live vector strains may have resulted from over-attenuation of the strain itself, it appears probable that current killing systems for plasmids suffer from additional limitations. In those situations where the chromosomal copy of the gene has been inactivated, rather than removed, may allow for restoration of the chromosomal copy via homologous recombination with the plasmid-borne gene copy if the bacterial strain utilized is recombination-proficient.

Balanced-lethal systems based on catalytic enzyme production are subject to a number of important deficiencies. In particular, since complementation of the chromosomal gene deletion requires only a single gene copy, it is inherently difficult to maintain more than a few copies of an expression plasmid. The plasmidless host strain must be grown on special media to chemically complement the existing metabolic deficiency.

Moreover, plasmidless cells may also benefit from "cross-feeding" effects when a diffusible growth factor is growth limiting.

There is therefore a need in the art for a Plasmid Maintenance System which is not solely reliant on a balanced lethal system, particularly for use in bacterial live vector vaccines.

2. SUMMARY OF THE INVENTION

The present invention relates generally to a stabilized expression plasmid comprising a Plasmid Maintenance System and a nucleotide sequence encoding a protein or peptide, such as a foreign antigen, and methods for making and using such stabilized expression plasmids. The Plasmid Maintenance System of the present optimizes viability by using stabilized lower copy number expression plasmids capable of expressing high levels of heterologous antigen in response to an environmental signal likely to be encountered in vivo after the vaccine organisms have reached an appropriate ecological niche.

In a particular aspect, the stabilized expression plasmid is employed in a *Salmonella typhi* live vector vaccine, such as the strain CVD908-htrA.

The invention optimizes the maintenance of expression plasmids at two independent levels by: (1) removing sole dependence on balanced lethal maintenance systems; and (2) incorporating a plasmid partition system to prevent random segregation of expression plasmids, thereby enhancing their inheritance and stability. In one aspect of the invention, the stabilized expression plasmid is recombinantly engineered to express one or more antigens, preferably one or more Shiga toxin 2 (Stx2) antigens or substantial homologues thereof, such as Shiga toxin subunit pentamers or a genetically detoxified Stx 2.

The stabilized expression plasmid preferably comprises one or more noncatalytic plasmid maintenance functions.

In another aspect, the expression plasmid comprises a Plasmid Maintenance System which comprises at least one PSK function and at least one SEG function. For example, the Plasmid Maintenance System may comprise a two-component Plasmid Maintenance System comprising one PSK function and one SEG function. Alternatively, the Plasmid Maintenance System may comprise a three-component Plasmid Maintenance System comprising a PSK function, a SEG function and another PSK. In a preferred alternative, the Plasmid Maintenance System comprises hok-sok+par+parA+phd-doc; wherein any of the stated functions may be replaced by a substantial homologue thereof.

The Plasmid Maintenance Systems can be incorporated into multicopy expression plasmids encoding one or more proteins or peptides of interest. Such multicopy expression plasmids produce a gene dosage effect which enhances the level of expression of the protein or peptide of interest. Where the Plasmid Maintenance System is to be employed in a bacterial live vector vaccine, the protein or peptide of interest is one or more foreign antigens.

In one aspect, the expression plasmid is a vaccine expression plasmid comprising a Plasmid Maintenance System and at least one antigen, for example, at least one Shiga toxin 2 (Stx2) antigen and/or substantial homologue thereof. Where the antigen is a Shiga toxin 2 antigen, the Shiga toxin 2 antigen can, for example, be either a B subunit pentamer or a genetically detoxified Stx 2.

In another aspect the expression plasmid comprises a Plasmid Maintenance System which incorporates the ssb balanced lethal system and the ssb locus of the bacterial live vector has been inactivated using a suicide vector comprising a temperature sensitive origin of replication. In one aspect, the bacterial live vector is *S. typhi* and the suicide vector is used to inactivate the ssb locus of *S. typhi*. In one aspect, the suicide vector is a derivative of pSC101 which carries sacB, described herein.

In another aspect, the present invention provides a Plasmid Maintenance System incorporating a PSK function involving a silent plasmid addiction system based on anti-sense RNA control mechanisms that only synthesize lethal proteins after plasmid loss has occurred.

In one aspect the expression plasmid comprises a series of expression plasmids, each comprising self-contained genetic cassettes encoding regulated expression of a heterologous antigen, an origin of replication, and a selectable marker for recovering the plasmid.

In one aspect the expression plasmid comprises a Plasmid Maintenance System which incorporates a PSK function based on the ssb gene. In a related aspect, mutated alleles such as ssb-1, described herein, are incorporated into the expression plasmids to enhance higher copy number plasmids by over-expression of SSB1-like proteins to form the required biologically active tetramers of SSB.

In another aspect, the expression plasmid comprises a promoter. The promoter is preferably an inducible promoter, such as the ompC promoter. In one aspect, the inducible promoter is the mutated $P_{ompC1}$, or the $P_{ompC3}$ promoter described herein.

In one aspect, the expression plasmid of the present invention comprises a plasmid inheritance (or partition) locus; an origin of replication selected to provide copy number which effectively stabilizes a given antigen; a PSK function; and a nucleotide sequence encoding an antigen and a promoter which ultimately controls translation of the antigen and has a strength which is selected to improve antigen production without killing the cell.

The present invention also provides a method of using the expression plasmid comprising transforming a bacterial cell using said expression plasmid, and culturing the bacterial cell to produce the protein or peptide (e.g., the antigen), and/or administering said transformed cell or cell culture to a subject. Where the transformed bacterial cells are administered to a subject, they are administered in an amount necessary to elicit an immune response which confers immunity to the subject for the protein or peptide. The subject is preferably a human, but may also be another animal, such as a dog, horse, or chicken.

In one aspect, an expression plasmid is provided which comprises at least 3 independently functioning expression cassettes wherein one cassette encodes a protein or peptide of interest and the remaining cassettes each encode a different Plasmid Maintenance Function.

In one aspect, an expression plasmid is provided which encodes (1) a test antigen operably linked to a promoter and (2) a Plasmid Maintenance System.

In another aspect, a regulated test antigen expression cassette is provided which operates such that as induction of antigen expression is increased, a metabolic burden is placed on the bacterium which leads phenotypically to plasmid instability, i.e. a selective advantage is created for all bacteria which can spontaneously lose the offending plasmid. The test antigen can be the green fluorescent protein (GFPuv). The expression cassette encoding the test antigen can also comprise an inducible promoter, such as the ompC promoter, positioned such that the inducible promoter ultimately drives the translation of the test antigen.

In one aspect, a method of making an expression plasmid is provided which comprises synthesizing an expression plasmid comprising at least 3 independently functioning expression cassettes wherein one cassette encodes a protein or peptide of interest and the remaining cassettes each encode a different Plasmid Maintenance Function.

In one aspect, a method of screening Plasmid Maintenance Systems is provided comprising: providing one expression cassette which encodes a protein or peptide of interest, and at least two other expression cassettes, each encoding and capable of expressing in the host bacterial live vector a different Plasmid Maintenance Function; inserting the three expression cassettes into a single expression plasmid; transforming a bacterial live vector with the single expression plasmid; culturing the transformed bacterial live vector, and determining the rate of introduction of plasmidless cells into the culture.

In one aspect, the present invention comprises an attenuated bacterial live vector vaccine comprising an attenuated bacterial live vector which has been transformed with a stabilized expression plasmid comprising a Plasmid Maintenance System, preferably a non-catalytic plasmid maintenance system.

In one aspect, the present invention comprises an attenuated bacterial live vector vaccine comprising an attenuated bacterial live vector which has been transformed with an expression plasmid comprising a Plasmid Maintenance System which incorporates at least one PSK system and at least one SEG system. The attenuated bacterial live vector can, for example, be *S. typhi* CVD908-htrA.

The present invention also provides a method for vaccinating a subject comprising administering to the subject an amount of a bacterial live vector vaccine sufficient to elicit an enhanced immune response. The present invention also provides a method for preventing a disease by vaccinating a subject using an amount of such bacterial live vector sufficient to elicit a protective immune response to one or more pathogens of such disease. The subject is preferably a human but may also be another animal, such as a horse, cow or pig. For example, the present invention provides a method for preventing hemolytic uremic syndrome (HUS) caused by Shiga, toxin 2-producing enterohemorrhagic *Escherichia coli* by administering to a subject an amount of a bacterial live vector transformed with a stabilized plasmid encoding at least one Shiga toxin 2 antigen.

In another aspect, the present invention provides a method for screening Plasmid Maintenance Systems for efficacy, the method comprising: providing expression plasmids comprising the Plasmid Maintenance Systems described herein and encoding for a protein or peptide of interest, said expression plasmids having copy numbers which vary from low copy number (e.g. ~5copies per cell) to medium copy number (e.g. ~15 copies per cell) to high copy number (e.g. ~60 copies per cell); transforming bacterial live vectors with such expression plasmids; and testing for rate of introduction of plasmidless cells and/or rate of growth of plasmid-containing cells. The modified origins of replication may be origins of replication from the plasmids pSC101 (low copy number), pACYC184 (medium copy number), and pAT153 (high copy number). Independently functioning plasmid replication cassettes can be utilized which permit testing of the efficiency of one or more plasmid stabilization systems as copy number is increased.

In another aspect, the present invention provides stabilized expression plasmids for use in attenuated *S. typhi* live vectors which contain a selectable marker which can readily be replaced by a non-drug resistant locus or by a gene encoding an acceptable drug resistance marker such as aph encoding resistance to the aminoglycosides kanamycin and neomycin.

The Plasmid Maintenance Systems of the present invention provide improved stability of recombinant plasmids, overcoming prior art problems of plasmid instability, for example, in bioreactor and live vector vaccination uses. The plasmids of the present invention are specifically tailored for vaccine applications though such plasmids are also useful in large scale protein production.

The plasmids of the present invention are a major improvement over the prior art in that they overcome the problems associated with plasmidless takeover and plasmid instability and have wide ranging utility in fields such as commercial protein production and attenuated bacterial live vector vaccine production.

There has long been a need for a solution to the problems of plasmidless takeover and plasmid stability associated with the field of vaccine delivery and protein production. The present invention solves this long felt need.

3. DEFINITIONS

The term "Plasmid Maintenance System" ("PMS") as used herein refers to a nucleotide sequence comprising at least one post-segregational killing function ("PSK") and at least one partitioning or segregating system ("SEG"), and optionally including any other Plasmid Maintenance Function.

The term "Plasmid Maintenance Function" is used herein to refer to any plasmid-stability enhancing function associated with a PMS. The term includes both naturally-occuring nucleotide sequences encoding plasmid maintenance functions, as well as nucleotide sequences which are substantially homologous to such naturally-occurring plasmid maintenance functions and which retain the function exhibited by the corresponding naturally-occurring plasmid maintenance function.

The term "Post-Segregational Killing System" (PSK) is used herein to refer to any function which results in the death of any newly divided bacterial cell which does not inherit the plasmid of interest, and specifically includes balanced-lethal systems such as asd or ssb, proteic systems such as phd-doc, and antisense systems such as hok-sok. The term includes both naturally-occuring nucleotide sequences encoding such PSKs, as well as nucleotide sequences which are substantially homologous to such naturally-occurring nucleotide sequences and which retain the function exhibited by the corresponding naturally-occurring nucleotide sequences.

The term "substantially homologous" or "substantial homologue," in reference to a nucleotide sequence or amino acid sequence, indicates that the nucleic acid sequence has sufficient homology as compared to a reference sequence (e.g., a native sequence) to permit the sequence to perform the same basic function as the corresponding reference sequence; a substantially homologous sequence is typically at least about 70 percent sequentially identical as compared to the reference sequence, typically at least about 85 percent sequentially identical, preferably at least about 95 percent sequentially identical, and most preferably about 96, 97, 98 or 99 percent sequentially identical, as compared to the reference sequence. It will be appreciated that throughout the specification, where reference is made to specific nucleotide sequences and/or amino acid sequences, that such nucleotide sequences and/or amino acid sequences may be replaced by substantially homologous sequences.

The terms "Segregating System"and/or "Partitioning System" (both referred to herein as "SEG") are used interchangeably herein to refer to any plasmid stability-enhancing function that operates to increase the frequency of successful delivery of a plasmid to each newly divided bacterial cell, as compared to the frequency of delivery of a corresponding plasmid without such a SEG system. SEG systems include, for example, equipartitioning systems, pair-site partitioning systems, and the par locus of pSC101. The term includes both naturally-occuring nucleotide sequences encoding such SEG systems, as well as nucleotide sequences which are substantially homologous to such naturally-occurring nucleotide sequences and which retain the function exhibited by the corresponding naturally-occurring nucleotide sequences.

The term"detoxified" is used herein to describe a toxin having one or more point mutations which significantly reduce the toxicity of the toxin as compared to a corresponding toxin without such point mutations.

The term"immunizingly effective" is used herein to refer to an immune response which confers immunological cellular memory upon the subject, with the effect that a secondary response (to the same or a similar toxin) is characterized by one or more of the following characteristics: shorter lag phase in comparison to the lag phase resulting from a corresponding exposure in the absence of immunization; production of antibody which continues for a longer period than production of antibody for a corresponding exposure in the absence of such immunization; a change in the type and quality of antibody produced in comparison to the type and quality of antibody produced from such an exposure in the absence of immunization; a shift in class response, with IgG antibodies appearing in higher concentrations and with greater persistence than IgM; an increased average affinity (binding constant) of the antibodies for the antigen in comparison with the average affinity of antibodies for the antigen from such an exposure in the absence of immunization; and/or other characteristics known in the art to characterize a secondary immune response.

4. BRIEF DESCRIPTION OF THE DRAWINGS

Figure 1B:
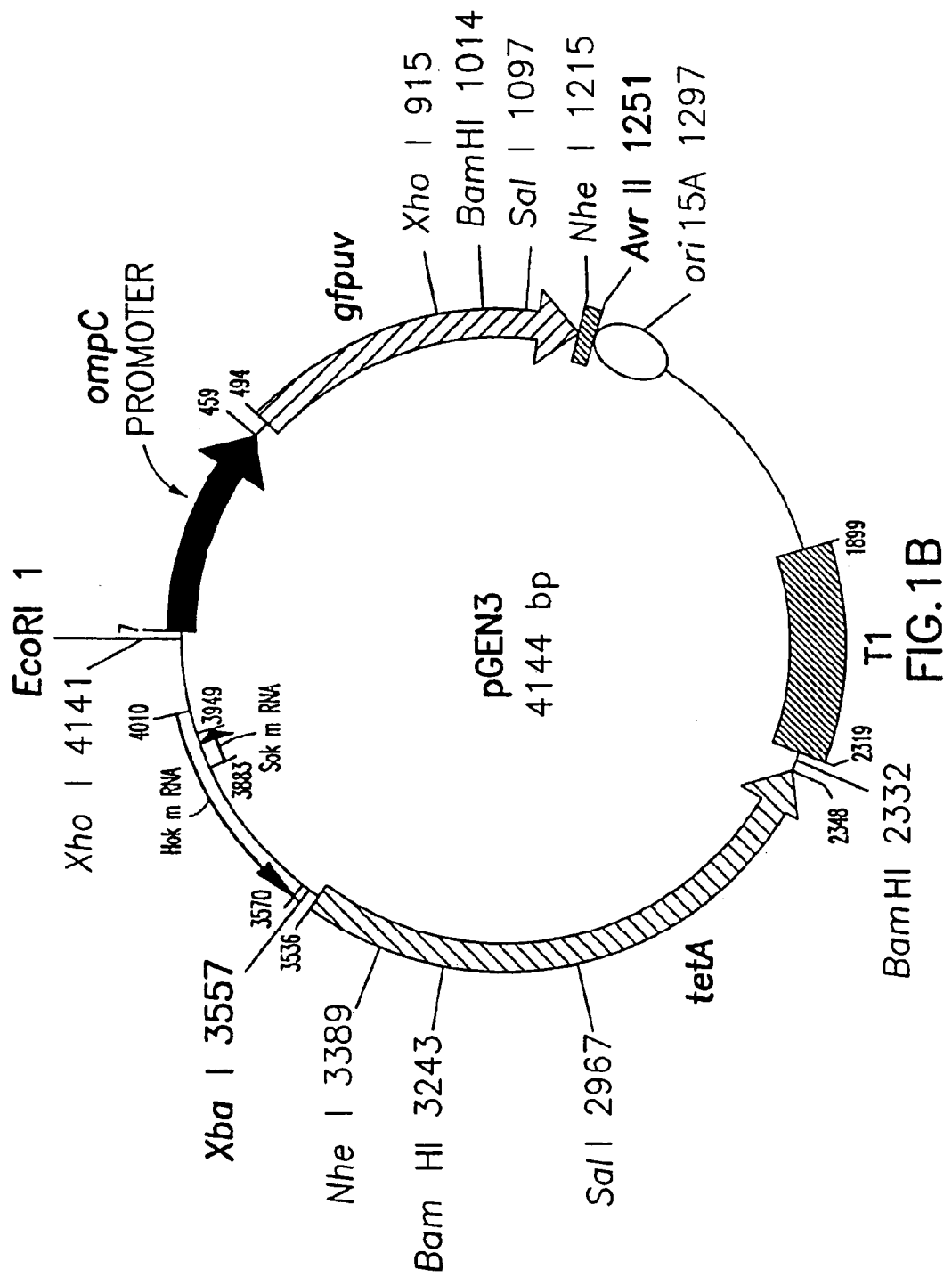
Figure 1C:
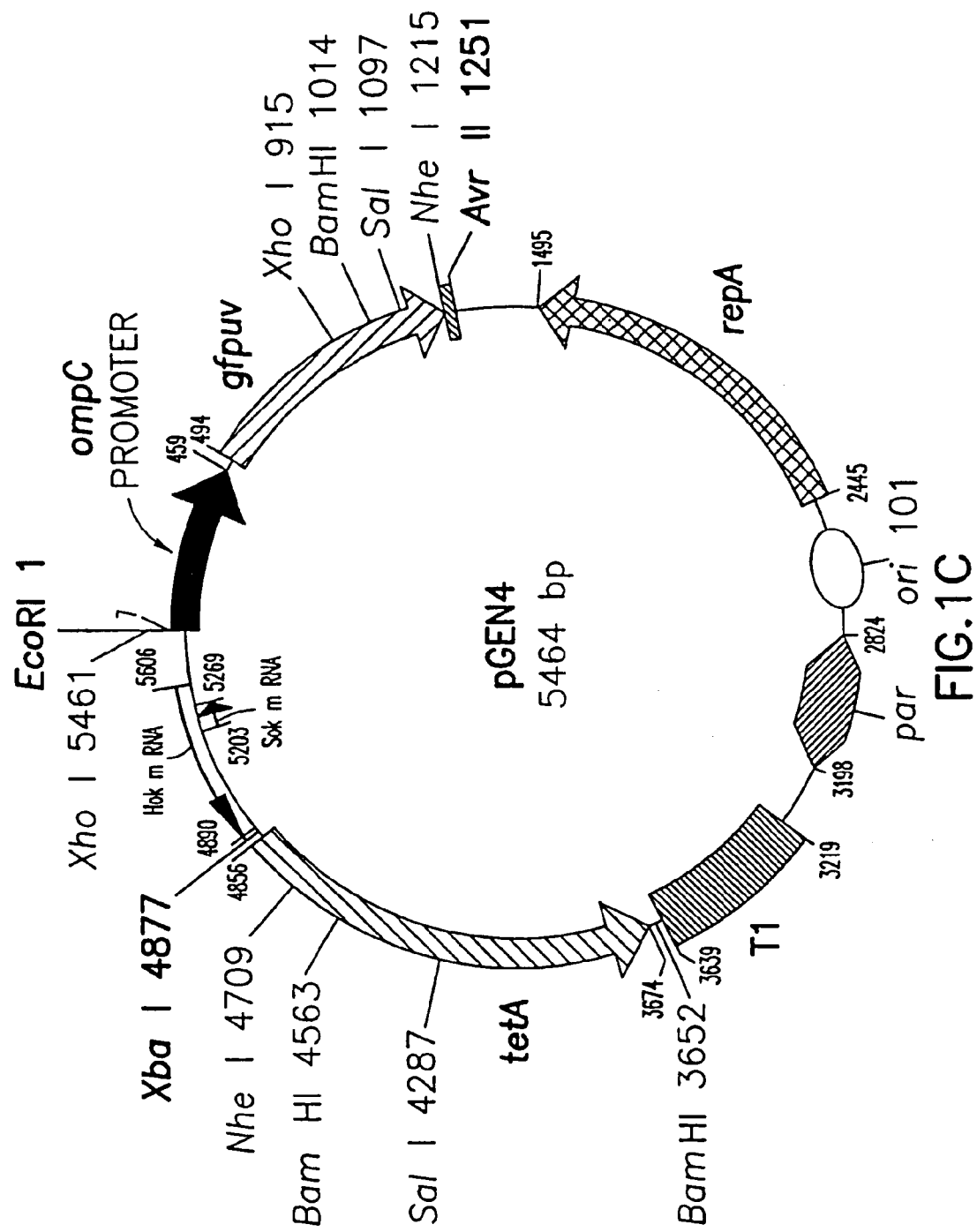

FIGS. 1A–1C: Genetic maps of exemplary pGEN expression plasmids (pGEN2, pGEN3, and pGEN4) of the present invention.

FIGS. 2A–2D: Genetic maps of exemplary oriE1-based expression plasmids (pJN72, pJN51, pJN10, and pJN12) of the present invention.

FIG. 3A–H: Flow cytometry histograms of GFP fluorescence for CVD 908-htrA carrying expression vectors with the hok-sok post-Segregational killing system.

FIGS. 4A–D Complete pGEN2 nucleotide sequence (SEQ ID NO: 1), comprising nucleotides 1–419.

FIG. 5A–B: Partial pGEN3 nucleotide sequence (SEQ ID NO: 2), comprising, nucleotides 1201–2397 and showing the sequence of ori15A.

FIG. 6A–C Partial pGEN4 nucleotide sequence (SEQ ID NO: 3), comprising nucleotides 1201–3848 and showing the sequence of ori101.

FIGS. 7A–7E: Genetic maps of exemplary ori15A-based pGEN expression plasmids (pGEN91, pGEN111, pGEN121, pGEN193, and pGEN222) of the present invention.

FIG. 8A–C: Flow cytometry histograms of GFP fluorescence for expression plasmids pGEN91, pGEN111, pGEN121, pGEN193, and pGEN222.

5. DETAILED DESCRIPTION OF THE INVENTION

Bacterial live vector vaccines employ a bacterial live vector to express genes encoding protective antigens of bacterial, viral or parasitic pathogens. The bacterial protective antigens are preferably non-native to the bacterial live vector, i.e. heterologous. The bacterial live vector vaccine is administered to a host, thereby exposing the expressed antigens to the host's immune system, eliciting an immune response of appropriate character to confer immunity to the host.

In order to achieve enhanced immunogenicity, the plasmids expressing such protective antigens must be stabilized. To the inventor's knowledge, no currently available *S. typhi*-based Plasmid Maintenance System takes advantage of naturally occurring partition mechanisms known to improve the stability of multicopy plasmids in other strains.

The present invention provides a non-catalytic Plasmid Maintenance System for the stabilization of expression plasmids encoding foreign antigens in a *S. typhi* live vector vaccine strain. In one aspect the *S. typhi* strain is CVD 908-htrA. In another aspect, the present invention improves and/or optimizes maintenance of expression plasmids by providing Plasmid Maintenance Systems which operate at two independent levels: (1) removing sole dependence on catalytic balanced lethal maintenance systems; and (2) incorporating a plasmid partition system which will prevent random segregation of the expression plasmids, thereby enhancing their inheritance and stability. A critical reason for pursuing this particular approach is that this method of improving plasmid maintenance involves no additional manipulations of the live vector strain, and therefore can improve the immunogenicity of heterologous antigens expressed within any live vector strain.

The non-catalytic Plasmid Maintenance System of the present invention improves the stability of multicopy expression plasmids within a bacterial live vector vaccine, such as CVD908htrA.

In one aspect, the present invention incorporates the naturally occurring PSK function hok-sok from the antibiotic-resistance factor pR1, or a substantial homologue thereof, within multicopy expression plasmids. The hok-sok system is a silent plasmid addiction system based on antisense RNA control mechanisms that only results in synthesis of lethal proteins after plasmid loss has occurred.

The present invention also provides a plasmid maintenance system comprising a complementation-based PSK function in which the chromosomal gene ssb, encoding the essential non-catalytic single-stranded binding protein (SSB) required for DNA replication, is specifically deleted and inserted within a multicopy expression plasmid.

The present invention also provides an improved Plasmid Maintenance System comprising an expression plasmid encoding at least one SEG locus and at least one PSK function.

5.1 Suicide Vectors

Heterologous antigens can be expressed within live vector strains, such as CVD908-htrA, from genes residing either on plasmids or integrated within the chromosome. One technique for integrating these genes into the host chromosome involves the use of temperature sensitive "suicide vectors" such as pIB307 which contains a temperature-sensitive origin of replication from pSC101 (ori100$^{ts}$). The present invention provides an improved suicide vector for use in CVD908 and CVD908-htrA, derived from pIB307 which allows for easier construction of mutagenesis cassettes to alter the live vector chromosome.

Integration of these suicide vectors into the chromosome by homologous recombination results from temperature inactivation of the plasmid replication protein, RepA, a protein essential to the function of ori101. Spontaneous resolution of the resulting unstable merodiploid intermediates is detected by counter-selection for loss of the sacB gene contained on the resolving suicide vector. The sacB gene contained on all excised plasmids encodes the levansucrase enzyme, which is lethal when expressed within the cytoplasm of enteric bacteria, including *S. typhi*, growing in the presence of sucrose. Since resolving merodiploids are selected by incubating in the presence of 10% sucrose, excised plasmids will kill host bacteria unless they cure spontaneously.

This system was successfully used to integrate a kanamycin-resistance cassette into the ΔaroC1019 locus of CVD908. However, these experiments were successful because the gene being mobilized into the chromosome of *S. typhi* encoded a selectable drug-resistance marker. Using these early vectors, replacing the kanamycin-resistance cassette with a non-selectable marker was not successful because, although the incoming marker could be integrated into the chromosome as a merodiploid, resolution of the merodiploid to replace the drug resistance gene was never detected.

The present invention also provides a method for using such suicide vectors to inactivate the ssb locus of attenuated *Salmonella typhi* strains such as CVD908-htrA.

The present invention allows such suicide vectors to permit efficient mobilization of genes expressing proteins or peptides of interest, such as heterologous antigens, into the chromosome of *S. typhi* CVD908-htrA in two stages. For example, the present inventor introduced a sacB-aph cassette into the ΔaroC1019 locus, which was then selected using kanamycin. Generation of this *S. typhi* CVD908-htrΔaroC1019::sacB-aph strain produced a valuable intermediate strain into which, in theory, any structural gene can be efficiently inserted into the aroC locus by marker-exchange. The sacB gene is used as a counter-selectable marker by passing merodiploids in the presence of 10% sucrose to select for replacement of the sacB-aph cassette with the incoming antigen cassette, since resolution of merodiploids in the presence of sucrose will result in loss of the sacB gene, in order to produce viable progeny. This intermediate strain was employed to efficiently integrate the non-toxigenic mutant LT-K63 of the *E. coli* heat-labile enterotoxin, creating CVD908ΔaroC1019::LT-K63.

5.2 Plasmid-Based Expression of Heterologous Antigens

Although chromosomal integration of foreign genes confers stability to such sequences, the genetic manipulations involved can be difficult, and the drop in copy number of the heterologous gene often results in production of insufficient levels of heterologous antigen to ensure an optimal immune response.

In contrast, plasmid stability is a complex phenomenon which depends on multiple factors including (1) copy number of the plasmid; (2) appropriately regulated expression of genes contained within the plasmid; and (3) selective pressure for ensuring the proper segregation and inheritance of the plasmid.

To ensure stability, plasmids must be replicated in a regulated manner to prevent their copy number from rising to lethal levels.

In addition, plasmids must segregate during the division of a growing bacterium to ensure that each daughter cell receives at least one copy of the plasmid. Segregation can be a passive, random event or an active process involving synthesis of novel proteins which aid in plasmid segregation and inheritance. Successful inheritance of randomly segregating plasmids relies on a high enough copy number of randomly distributed plasmids within a dividing bacterium to virtually guarantee inheritance of at least one plasmid by each daughter cell.

The commonly used plasmid cloning vectors, including medium copy number pBR322 derivatives and high copy number pUC plasmids, are inherited by random segregation.

Active segregation involves the synthesis of proteins which are proposed to bind to such plasmids and further coordinate with the membranes of dividing bacteria to ensure that each daughter receives at least one plasmid copy. Plasmids employing such active partitioning systems are typically very low copy number plasmids such as the F sex factor of *E. coli* or antibiotic resistance R-factors such as pR1 and pRK2.

The present invention exploits naturally occurring SEG functions to enhance inheritance of multicopy expression plasmids, which would otherwise be inherited by random segregation, to increase the stability of these plasmids.

The present invention also takes advantage of other naturally occurring genetic systems in which daughter cells which do not successfully inherit an expression plasmid will be killed and removed from the growing population, i.e., PSK functions. The incorporation of more than one category of plasmid stabilization function is referred to herein as a Plasmid Maintenance System. For example, the incorporation of both a SEG function such as a partition locus and a PSK function into a single expression plasmid yields a Plasmid Maintenance System.

It should be noted that a gene conferring resistance to a bactericidal antibiotic, such as the aph gene encoding resistance to kanamycin and neomycin, is also considered a PSK function, as is the asd-based balanced-lethal system.

5.3 Balanced Lethal Systems

One method of ensuring the inheritance of expression plasmids involves the construction of a PSK system or a substantial homologue thereof, referred to as a balanced lethal system, for plasmids expressing heterologous antigens. In a plasmid-based balanced lethal system, plasmids replicating in the cytoplasm of the bacterium express a critical protein required by the bacterium to grow and replicate. Loss of such plasmids removes the ability of the bacterium to express the critical protein and results in cell death.

The asd system has recently been introduced into attenuated *S. typhi* vaccine strains in an attempt to increase the stability of plasmids expressing synthetic hepatitis B viral peptides.

However, when volunteers were immunized with these live vector strains, no immune response to the foreign antigen was detected. See Tacket et al., *Infection and Immunity*, 65:3381, 1997 (incorporated herein by reference). In fact, to date, few reports have documented an immune response to plasmid-based expression of a foreign antigen from plasmids (stabilized or otherwise) after vaccination of humans with an attenuated *S. typhi* live vector.

Although in some cases failure of live vector strains may have resulted from over-attenuation of the strain itself, the inventor's conclusion is that currently used PSK functions for plasmids suffer from additional limitations, in particular, from segregation limitations and catalytic activity limitations. The present invention provides improved expression plasmids comprising enhanced segregation capabilities by incorporating at least one partitioning system along with at least one PSK system.

5.4 Segregation Limitations

One limitation of plasmid maintenance functions such as the asd function (as well as the thyA function) is that they do not enhance the inheritance of resident plasmids, which continue to segregate randomly with or without the presence of the asd function. Therefore, if resident expression plasmids carrying asd genes are inherently unstable, they will be lost, regardless of the requirement of the bacterium for Asd.

The inherent stability of an asd expression plasmid can be defined by growing plasmid-bearing strains in the presence of DAP, which removes the selective pressure that ensures that all viable bacteria contain the expression plasmid. If a given plasmid is inherently unstable, it will be lost from bacteria at a high rate and such plasmidless bacteria will lyse in the absence of growth supplements; the overall result of this effect will be a population of bacteria that grows much slower than wildtype unaltered strains.

The present invention improves plasmid stability by incorporating a SEG function, such as a partition locus, or a substantial homologue of a SEG function, onto the expression plasmid to enhance the inheritance of such plasmids by actively dividing bacteria. Partition loci are naturally present on the virulence plasmids of *S. typhimurium*. Tinge and Curtiss, *Journal of Bacteriology*, 172:5266, 1990 (incorporated herein by reference) reported that such partition loci were well conserved among *S. typhimurium* virulence plasmids, and that when a 3.9 kb restriction fragment encoding this locus was introduced onto the lower copy number plasmid pACYC184 (~15 copies per cell), the observed plasmid stability increased from 34% plasmid-containing cells to 99% plasmid-bearing cells after 50 generations. The nucleotide sequence of this locus was later determined by Cerin and Hackett, *Plasmid*, 30:30, 1993 (incorporated herein by reference), (GenBank Accession Number M97752).

5.5 Catalytic Activity Limitations

Another potential limitation of a plasmid maintenance function such as the asd function (as well as the thyA system) is its reliance on an enzyme with catalytic activity. Given that complementation with only a single copy of the asd gene is sufficient to remove auxotrophy, it is not clear why all copies of a multicopy plasmid should remain stable, especially if they encode an especially problematic heterologous antigen which inhibits growth of the bacterium.

Further, although higher copy number expression plasmids may express appreciable levels of a given heterologous antigen in vitro, such plasmids may not be maintained at the expected copy numbers in vivo due to toxicity and may in fact be present at much lower copy numbers, which would be expected to reduce any observed immune response specific for the heterologous antigen. Accordingly, the present invention thus provides stably maintained low and medium copy number plasmids for expressing heterologous antigens.

5.6 The Non-Catalytic ssb PSK Function

The potential limitation of catalytic activity associated with balanced lethal systems is addressed here through the use of plasmids expressing the single-stranded binding protein (SSB) from *S. typhi* to trans-complement an otherwise lethal mutation introduced into the chromosomal ssb gene. The biochemistry and metabolic roles of the *E. coli* SSB protein have been extensively reviewed in Lohman et al., *Annual Reviews in Biochemistry* 63:527, 1994 and Chase et al., *Annual Reviews in Biochemistry* 55:103, 1986 (the disclosures of which are incorporated herein by reference).

SSB is a non-catalytic 177 amino acid protein, with a relative molecular weight of 19 kDa, that binds with high affinity to single-stranded DNA (ssDNA), and plays an essential role as an accessory protein in DNA replication, recombination, and repair. The biologically relevant form of SSB involved in binding to ssDNA is a tetramer, which binds in two modes to ssDNA, intimately associating with an average of either 35 ($SSB_{35}$-binding mode) or 65 bases ($SSB_{65}$-binding mode). The specific conditions controlling the preferred mode of binding are complex and depend on the surrounding concentration of monovalent and divalent salts, pH, and temperature, as well as the amount of SSB protein present. Under given conditions, high concentrations of SSB favor the $SSB_{35}$-binding mode, with lower SSB concentrations favoring the $SSB_{65}$-mode. However, it must be emphasized that in both binding modes, the required conformation of SSB is a tetramer.

Spontaneously occurring temperature-sensitive point mutations within the ssb gene have now been characterized at the biochemical, physiological, and nucleotide level; one such mutant, ssb-1, contains the point mutation His 55 to Tyr, and has been found to be unable to assemble correctly into tetramers at non-permissive temperatures and natural expression levels. These mutant strains exhibit temperature-sensitive lethal defects in DNA replication and recombination.

The segregation frequencies of plasmids carrying ssb which complement chromosomal ssb mutations in *E. coli* bacteria were examined by Porter et al. Bio/Technology 8:47, 1990 (incorporated herein by reference). They observed that in experiments involving bioreactors, the segregation frequency in plasmid-bearing strains growing in continuous culture under non-selective conditions for 150 hours was less than $1 \times 10^{-7}$; this segregation frequency was independent of copy number, as both lower copy number pACYC184 plasmids and very high copy number pUC19 plasmids were maintained at the same frequency. However, it must be noted that the plasmids involved expressed only a drug-resistance marker in addition to the SSB protein.

The present invention provides an improved plasmid maintenance system which incorporates a partition locus such as that present on pSC101, or a substantial homologue of such partition locus, and may also incorporate an active partitioning system, or a substantial homologue thereof, such as that described above for the virulence plasmid of *S. typhimurium*.

The present invention removes dependence on catalytic enzymes to confer plasmid stability. In one aspect, mutated alleles similar to ssb-1 are introduced into the expression plasmids to enhance higher copy number plasmids by overexpression of SSB1-like proteins to form the required biologically active tetramers of SSB. In another aspect the present invention provides a PSK function involving a silent plasmid addiction system based on antisense RNA control mechanisms that only synthesize lethal proteins after plasmid loss has occurred.

5.7 Expression Plasmids and Self-contained Genetic Cassettes

The present invention also comprises a series of expression plasmids which are referred to herein as pGEN plasmids. pGEN plasmids comprise self-contained genetic cassettes encoding regulated expression of a heterologous antigen, an origin of replication, and a selectable marker for recovering the plasmid. This vector series has been specifically designed to test whether any Plasmid Maintenance System can increase the stability of plasmids, for example within an attenuated *S. typhi* vaccine background.

The basic structure of these vectors is represented in FIG. 1, and the composite gene sequence for the vector pGEN2 (SEQ ID NO: 1) is represented in FIG. 4; FIGS. 5 & 6 show specific composite sequences for the origins of replication in pGEN3 and pGEN4 respectively.

It is critical to note that the pGEN plasmids are designed to comprise 3 independently functioning genetic cassettes. These cassettes have been constructed such that individual components can be optimized by replacement as necessary. Accordingly, in addition to the various Plasmid Maintenance Systems described herein, the cassettes can test other promising systems now in existence or which may become available in the future. Further, the optimized plasmid(s) can be adapted to express relevant protective heterologous antigens within attenuated vaccine strains for immunization of humans.

The pGEN plasmids provide a regulated test antigen expression cassette which operates such that as induction of antigen expression is increased, a metabolic burden is placed on the bacterium which leads phenotypically to plasmid instability, i.e. a selective advantage is created for all bacteria which can spontaneously lose the offending plasmid.

Thus one aspect of the present invention provides a conditionally unstable plasmid which can be examined for stability as plasmid maintenance systems are incorporated.

In a preferred mode, the regulated test antigen expression cassette contained within the pGEN plasmids comprises the inducible ompC promoter, or a substantial homologue thereof, driving expression of a detectable protein, such as the codon-optimized green fluorescent protein (GFPuv, available from Clontech), overexpression of which is toxic to *E. coli* and *S. typhi*.

The present invention also comprises a series of plasmid replicons having copy numbers which vary from low copy number (i.e., ~1 to ~10, preferably ~5 copies per cell) to medium copy number (i.e., ~11 to ~25, preferably ~15 copies per cell) to high copy number (i.e., ~26 to ~100, preferably ~60 copies per cell). To accomplish this, origins of replication from the well-characterized plasmids pSC101, pACYC184, and pAT153 have been modified using polymerase chain reaction (PCR) techniques to create independently functioning plasmid replication cassettes. These replication cassettes permit testing of the efficiency of a plasmid maintenance system as copy number is increased.

The present invention also comprises selectable expression plasmids for use in attenuated *S. typhi* live vectors. These expression plasmids contain a selectable marker which can ultimately be replaced either by a non-drug resistant locus, such as ssb, or by a gene encoding an acceptable drug resistance marker such as aph encoding resistance to the aminoglycosides kanamycin and neomycin.

To accomplish this, resistance cassettes encoding resistance to carbenicillin and tetracycline have been constructed, with transcription being efficiently terminated by an rrnB T1T2 terminator. A detailed description of the individual components comprising the expression and replication cassettes follows.

Figure 7A:
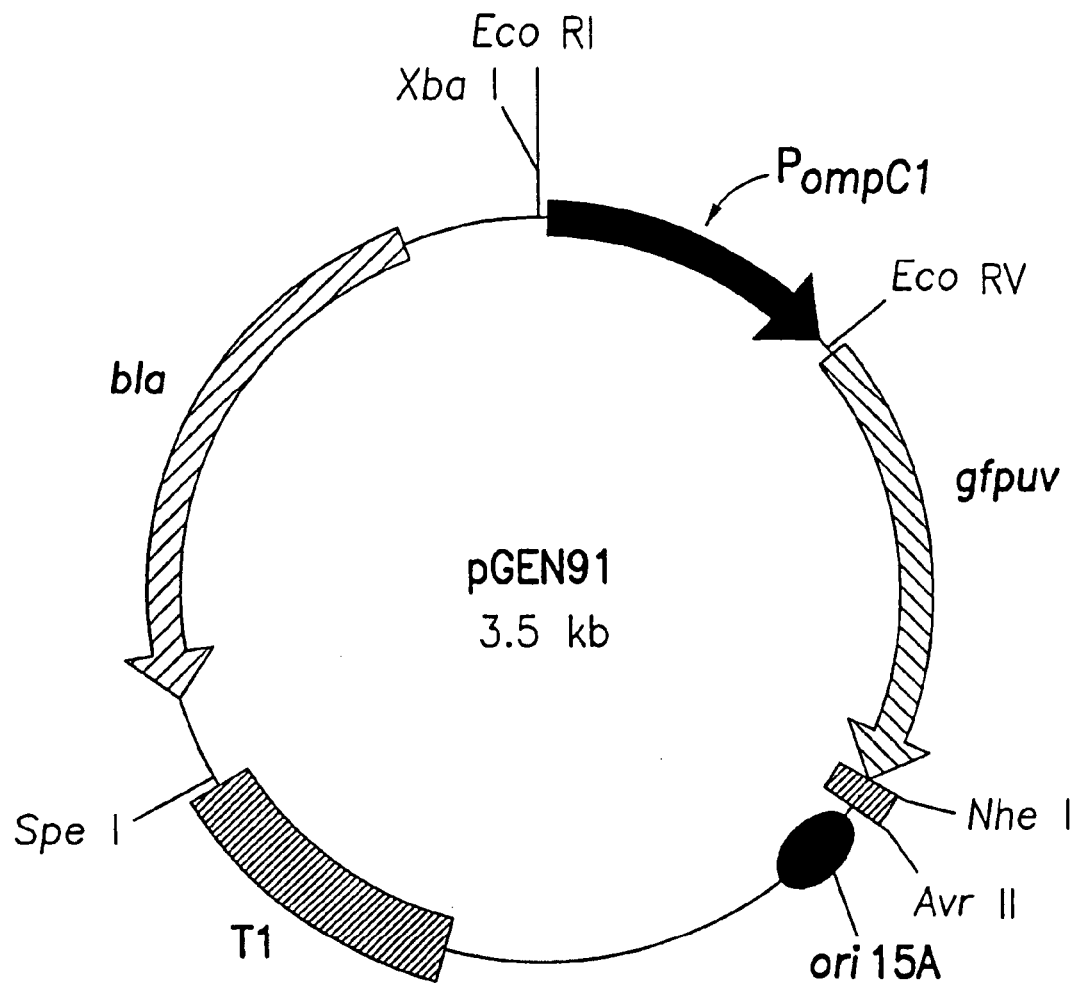
Figure 7B:
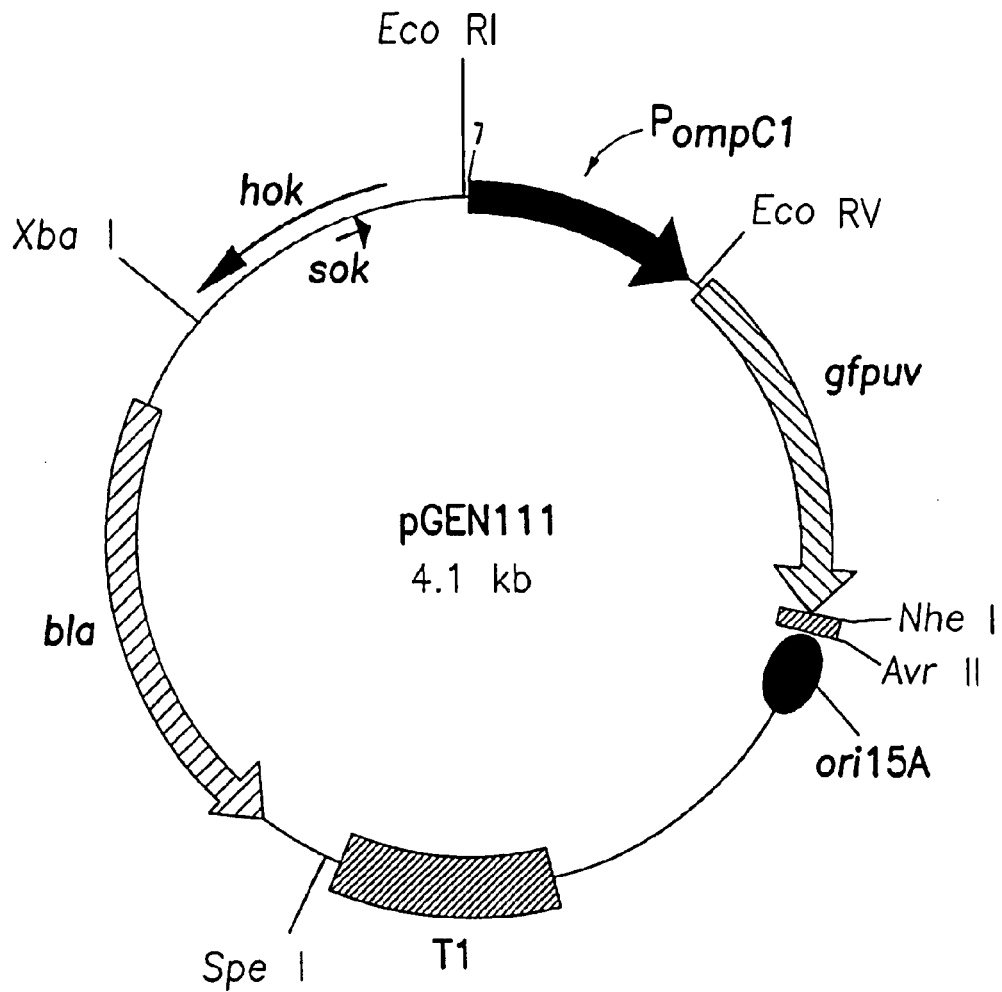

Specific components of the Plasmid Maintenance System can be systematically inserted into the basic expression replicons to assess any individual or synergistic influence of these functions on plasmid stability in the presence and absence of selection. For example, a post-segregational killing function (e.g., the hok-sok locus) can be inserted as an EcoRI-XbaI cassette, such that flanking transcription from surrounding loci, such as the antigen and selection cassettes, is divergent and will not significantly disturb the wild type transcription levels which control the lethality of this locus (FIG. 7B, pGEN111).

Figure 7C:
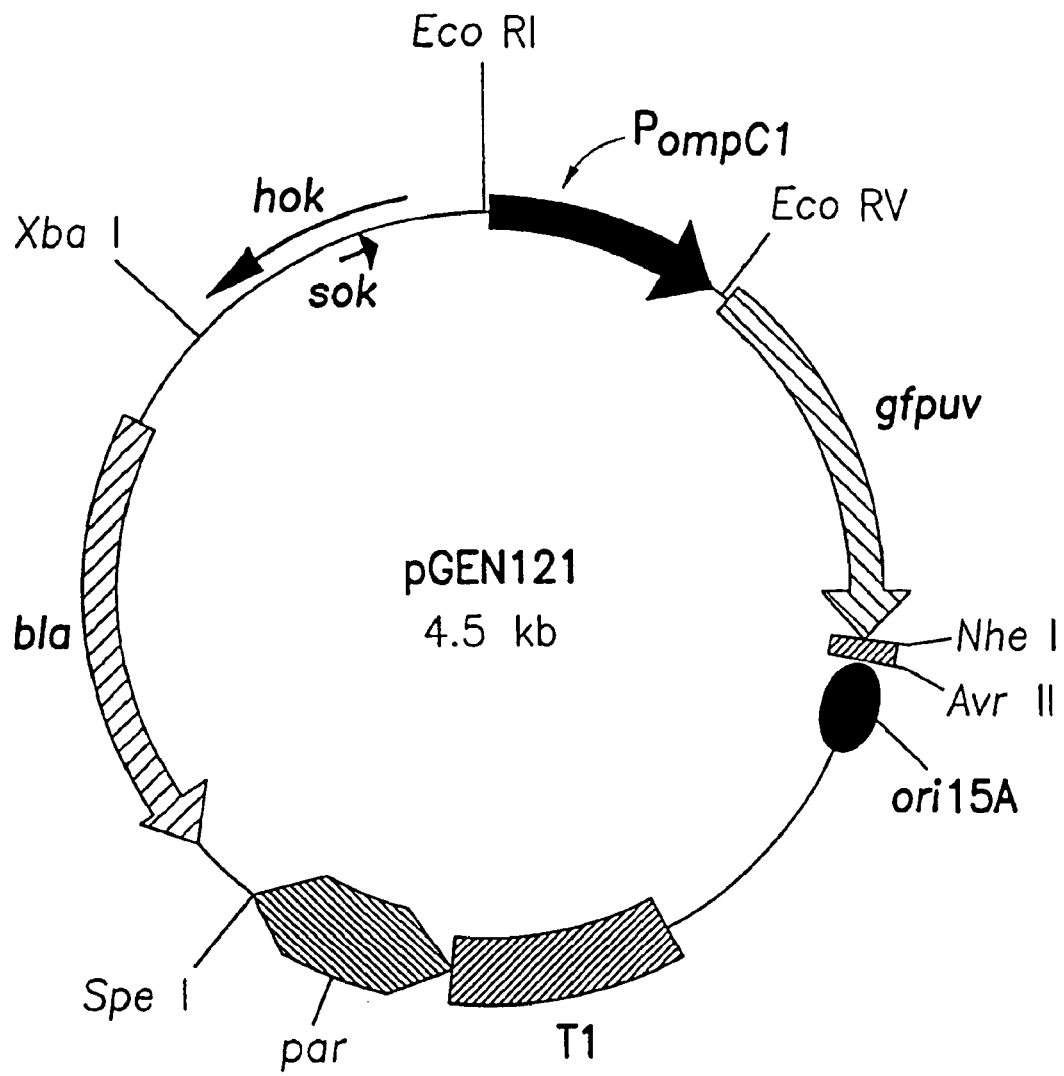

Similarly, the par passive partition locus can be inserted as a BamHI-BglII fragment between the origin of replication and selection cassettes (FIG. 7C, pGEN 121). Interestingly, in the work leading to the present invention, it was observed that the orientation of the par locus enhances synthesis of GFPuv on solid medium when inserted in the natural orientation found within ori101 of pSC101; this orientation was adopted for all of the expression plasmids.

Figure 7D:
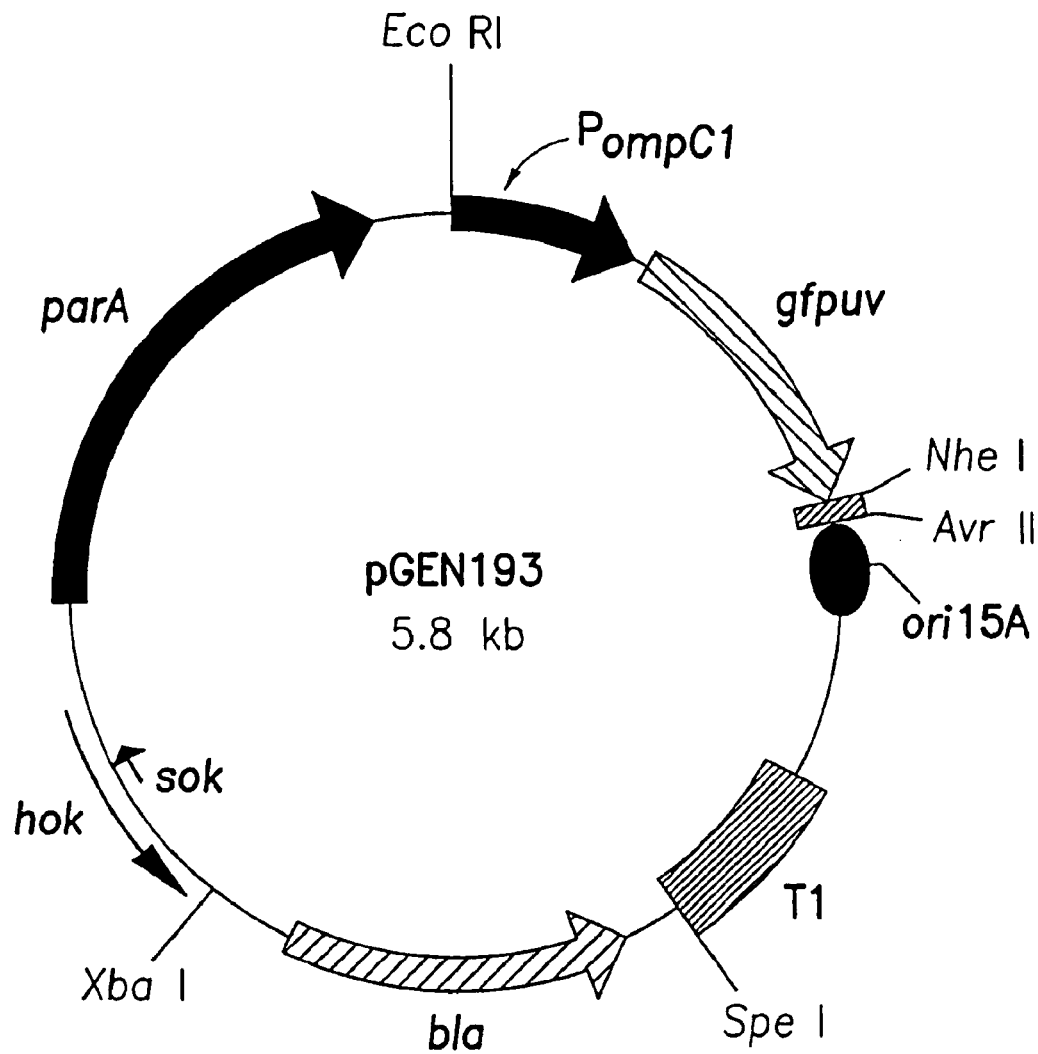
Figure 7E:
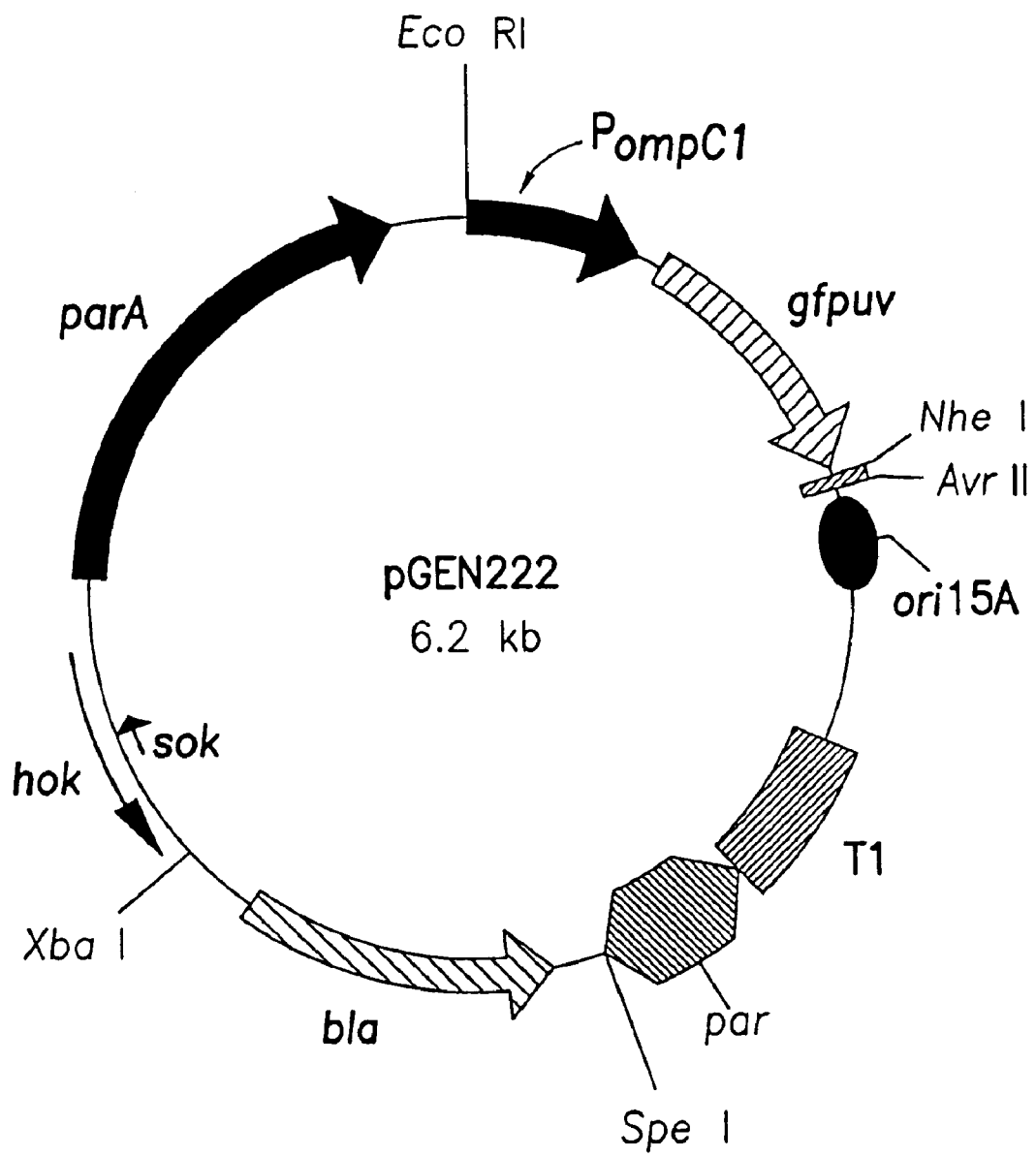

The active partitioning locus is preferably the parA locus, constructed as an XhoI-EcoRI cassette from the same pR1 resistance plasmid from which hok-sok was adapted. To preserve natural transcription levels and regulation within this locus, the cassette is preferably positioned within an area of the expression plasmids such that flanking transcription progresses away from parA (FIGS. 7D and 7E, pGEN193 and pGEN222).

5.8 Components of the Antigen Expression and Replication Cassettes 5.8.1 Promoter It will be appreciated by one of skill in the art that a wide variety of components known in the art may be included in the expression cassettes of the present invention, including a wide variety of transcription signals, such as promoters and other sequences that regulate the binding of RNA polymerase to the promoter. The operation of promoters is well known in the art and is described in Doi, Regulation of Gene Expression, *Modern Microbial Genetics* pages 15–39 (1991) (the entire disclosure of which is incorporated herein by reference). The ensuing description uses the ompC promoter by way of example, and is not meant to delimit the invention.

The promoter is preferably an environmentally regulatable promotor controlled by a biologically relevant signal such as osmolarity. In a preferred mode, the promoter is the ompC promoter. The ompC gene encodes a porin protein which inserts as a trimer into the outer membrane of a bacterial cell. Expression and control of ompC is complex and has recently been reviewed in considerable detail in Pratt et al., *Molecular Microbiology* 20:911, 1996 and Egger et al., Genes to Cells 2:167, 1997 (the disclosures of which are incorporated herein by reference).

Synthesis of the OmpC protein is ultimately controlled at the level of transcription by the osmolarity of the surrounding environment such that increases in osmolarity are accompanied by increases in the transcription of ompC. However, increases in osmolarity do not directly mediate increases in the transcription of ompC. Rather, the bacterium senses the surrounding osmolarity using a two-component signal transduction system encoded by the ompB operon. This operon is composed of two genes transcribed in the order envZ-ompR. The envZ gene encodes a 450 amino acid (a.a.) protein, containing two transmembrane regions, which inserts into the bacterial inner membrane (perhaps as a dimer) with an N-terminal 118 a.a. osmotic-sensing domain extending into the periplasmic space and a C-terminal 270 a.a. catalytic domain extending into the cytoplasm. The C-terminal catalytic domain possesses both kinase and phosphatase activities which are modulated by osmolarity such that as osmolarity increases, kinase activity predominates, and as osmolarity drops, phosphatase activity predominates.

EnvZ kinase activity phosphorylates aspartic acid residue 55 of the 239 a.a. cytoplasmic protein OmpR, creating OmpR-P. It is the OmpR-P modified protein which binds to the ompC promoter and activates transcription by RNA polymerase; therefore, as osmolarity increases, increasing kinase activity of EnvZ produces higher levels of OmpR-P, which in turn lead to greater transcription of ompC. OmpR–P binds to a region of the ompC promoter spanning bases −41 (relative to the transcriptional start site of +1) to −102, with initial binding of OmpR-P to bases −78 through −102 being followed by additional binding to bases extending to −41 as the concentration of OmpR-P increases with osmolarity. In addition, OmpR-P has been shown to bind to an AT-rich upstream region extending back to base −405 which further enhances ompC transcription.

In a preferred embodiment the ompC promoter fragment from *E. coli* spans nucleotides +70 through −389. This promoter can direct transcription within attenuated *S. typhi* strains of an antibiotic resistance gene, such as the kanamycin resistance gene in an osmotically sensitive manner. For example, our experiments have demonstrated that when the concentration of NaCl in liquid growth medium was increased from 0 mM to 300 mM, resistance to kanamycin increased from 0 μg/ml to >800 μg/ml.

5.8.2 Origin of Replication

Due to varying degrees of toxicity associated with different heterologous antigens (i.e. higher toxicity for antigens derived from parasitic organisms such *Plasmodium falciparum* vs. virtually no toxicity for the fragment C of tetanus toxin), the present invention provides live vector vaccines which preferably express such antigens from either low or medium copy plasmids. It will be appreciated by one skilled in the art that the selection of an origin of replication will depend on the degree of toxicity, i.e., the copy number should go down as toxicity to the bacterial strain goes up. In a preferred mode, the Plasmid Maintenance System(s) used are capable of stabilizing replicons of low or medium copy numbers.

It is preferable for the origin of replication to confer an average copy number which is between about 2 and about 75. In a preferred mode the origin of replication is selected to confer an average copy number which is between about 5 and about 50. More preferably the range is from about 5 to about 30. Optimally, the range is from about 15 to about 20.

In one aspect, the origin of replication is from pSC101, conferring a copy number of approximately 5 per genome equivalent.

The oriE1 locus specifies synthesis of a 555 base transcript called RNA I and synthesis of a 110 base antisense RNA transcript called RNA II. As RNA I is synthesized, the 5'-proximal region of the transcript adopts a stem-loop structure composed of 3 domains which can hybridize to a complementary stem-loop structure formed by RNA II, resulting in a double stranded RNA-RNA structure forming which causes plasmid replication to abort.

As synthesis of RNA I continues, generating the full-length 555 base transcript, a rearrangement of the secondary structure of the transcript destroys the initial 3 domain stem-loop structure to form an alternate stem-loop configuration which no longer hybridizes to RNA II. Formation of this alternate structure allows the transcript to hybridize to one DNA strand of the plasmid itself, forming an RNA-DNA complex which is nicked by endogenous RNAse H to trigger synthesis of the first DNA strand of the plasmid and plasmid replication.

Plasmid replication is therefore controlled by synthesis of RNA I, which undergoes a cascade of structural configurations leading to initiation of replication. The necessary progression of the RNA I folding cascade (and resulting replication initiation) is interrupted by competition of the domains with RNA II. This mechanism is essentially the same in plasmids containing either oriE1 ori15A.

The reason these two types of plasmids can coexist within the same bacterium is due to sequence divergence within the region of hybridization between RNA I and RNA II, such that the RNA II from ori15A will not hybridize to RNA I from oriE1; this sequence divergence also affects the stability of the RNA I: RNA II hybrid, accounting for the differences in copy number between plasmids carrying the oriE1 or ori15A origins of replication.

The structural organization of the engineered origins of replication cassettes for pSC101 (ori101; ~5 copies per genome equivalent), pACYC184 (ori15A derivative; ~15 copies per genome equivalent), and pAT153 (oriE1 derivative; ~60 copies per genome equivalent) are analogous in structure and function.

5.8.3 Expressed Protein or Peptide

When the expression cassette is used to screen Plasmid Maintenance Systems, it preferably expresses a protein or peptide with no metabolic activity. A preferred protein is the green flourescent protein (GFP) of the bioluminescent jellyfish *Aequorea victoria*, a 23B amino acid protein which undergoes a post-translational modification in which 3 internal amino acids ($^{65}$Ser-Tyr-Gly$^{67}$) are involved in a cyclization and oxidation reaction. The resulting fluorophore emits blue-green light maximally at a wavelength of 509 nm upon irradiation with long-wave ultraviolet light at a wavelength of 395 nm. In addition, fluorescence activity is remarkably constant over a wide range of pH from 5.5–12 and at temperatures up to 70° C.

Since GFP has no known catalytic activity, the level of observed fluorescence within individual bacteria expressing GFP can provide a direct indication of transcription levels of the gfp gene carried by each bacterium. Expression of the GFP protein has now been quantitated in a variety of both prokaryotic and eukaryotic cells and requires no additional cofactors or enzymes from *A. victoria*. Fluorophore formation is apparently dependent either on ubiquitous enzymes and cofactors, or is an autocatalytic event.

Individual bacteria expressing GFP can be quantitated either alone or within macrophages, epithelial cell lines, and infected animal tissues using flow cytometry. GFP fluorescence is absolutely dependent on residues 2–232 of the undenatured protein. However, fusion of unrelated biologically active protein domains to the N-terminus of GFP has still resulted in fusion proteins with the expected heterologous biological activity which continue to fluoresce as well.

It has been confirmed by sequence analysis (Clontech) that the gfp allele preferred here (i.e. gfpuv) expresses a GFP mutant (GFPuv) containing 3 amino acid substitutions (not involving the fluorophore) which increase fluorescence 18-fold over that of wildtype GFP.

In addition, 5 rarely used arginine codons have been optimized for efficient expression of GFP in *E. coli*. Since comparison of expression levels of various heterologous proteins in *E. coli* and CVD908 has demonstrated equivalent or superior expression within CVD908, it was expected that gfpuv will function efficiently in CVD908-htrA.

A coding sequence is inserted in a correct relationship to a promoter where the promoter and the coding sequence are so related that the promoter drives expression of the coding sequence, so that the encoded peptide or protein is ultimately produced. It will be understood that the coding sequence must also be in correct relationship with any other regulatory sequences which may be present.

5.8.4 Heterologous Antigens

The expression plasmids of the present invention preferably express an antigen for presentation to a host to elicit an immune response resulting in immunization and protection from disease. While Shiga toxins are presented herein as examples of antigens usefully expressed by the vaccine expression plasmids disclosed herein, the invention is broad in scope and encompasses the expression of any antigen which does not destroy the bacterial live vector and which elicits an immune response when the bacterial live vector containing said expression plasmid(s) is administered to a host, i.e., a human or other animal.

The vaccine expression plasmids provided herein are used to genetically transform attenuated bacterial strains, preferably strains used for human vaccination and most preferably used to transform attenuated *S. typhi* vaccine strains such as CVD908-htrA, and preferably encode either the B subunit of Stx2 or a genetically detoxified Stx2 holotoxin.

A subset of STEC most often referred to as enterohemorrhagic *E. coli* (EHEC) are capable of causing severe clinical syndromes including hemorrhagic colitis, hemolytic uremic syndrome (HUS) and thrombotic thrombocytopenic purpura (TTP) in a small proportion of infected individuals, in addition to causing non-bloody diarrhea in most others.

Hemorrhagic colitis is characterized by copious bloody diarrhea, usually without fever or with only low-grade fever and a relative paucity of fecal leukocytes demonstrable in the diarrheal stools. These features differentiate hemorrhagic colitis from dysentery caused by *Shigella* which is typically scanty stools of blood and mucus, preceded by high fever and with large numbers of fecal leukocytes visible by microscopy.

HUS, a potentially fatal disease that most often affects young children but may afflict individuals of any age, is characterized by the triad of microangiopathic hemolytic anemia, thrombocytopenia and uremia. Currently in North America, HUS is the most frequent cause of acute renal failure in infants and young children. In a study by Siegler et al. of 288 patients treated for postdiarrheal HUS in Utah from 1970–1994, severe disease (defined as anuria lasting longer than 7 days, oliguria lasting for longer than 14 days, or extrarenal structural damage such as stroke) occurred in 25% of cases and was associated with children less than two years of age; about one third of these severe cases of HUS resulted in death (5%) or severe sequelae including end-stage renal disease (5%) or chronic brain damage (3–5%), with less severe chronic problems involving hypertension, proteinuria, or azotemia.

TTP, which most often affects adults, is characterized by neurologic complications such as stroke, in addition to thrombocytopenia, hemolytic anemia and renal disease.

By far the most common EHEC serotype is O157:H7. Nevertheless, other EHEC serotypes also cause HUS and hemorrhagic colitis, including O26:H11, O111:H8 and a number of others. EHEC strains associated with HUS always elaborate one or more Shiga toxins and carry a 60 MDa virulence plasmid. In addition, most also harbor a chromosomal pathogenicity island (so-called LEE) having a set of genes that encode the ability to attach and efface. It is well accepted that Shiga toxins elaborated by EHEC play a key role in the pathogenesis of hemorrhagic colitis and HUS.

As described in detail below, the Shiga toxin family is comprised of two groups of toxins, Stx1 (which is essentially identical to cytotoxin/neurotoxin/enterotoxin produced by *Shigella dysenteriae* type 1, the *Shiga bacillus*) and Stx2 (which is immunologically distinct from Stx1 and has several related variants). In the USA, the overwhelming majority of EHEC associated with cases of HUS express Stx2, either alone or in conjunction with Stx1.

The most important reservoir of EHEC infection are bovines. The single most important mode of transmission of EHEC to humans is via the consumption of under-cooked contaminated beef, most often ground beef. Less commonly, a variety of other food vehicles and other modes of transmission have been incriminated. Most notably, EHEC are one of the handful of bacterial enteric pathogens, which, like *Shigella*, can be transmitted by direct contact or by contact with contaminated fomites.

There is great anticipation and optimism on the part of most epidemiologists that irradiation of meat sold in the USA will drastically curtail the transmission of EHEC to humans, since it will curtail the single most important mode of transmission. Nevertheless, certain risk groups exposed to other modes of transmission of EHEC will not benefit from this intervention. For example, the exposure of abattoir workers to EHEC, an occupational hazard, occurs at a point in the meat processing cycle prior to when irradiation would be utilized. For such special groups such as these for whom risk will remain even after irradiation of meat becomes commonplace, anti-EHEC vaccines can be useful. The present invention provides vaccines against EHEC useful for the prevention of infection (in the animal reservoirs or in humans) and for preventing the severe complications of EHEC infection by stimulating neutralizing Shiga antitoxin.

Studies with attenuated *Vibrio cholerae* O1 expressing Stx1 B subunit have demonstrated the feasibility of eliciting neutralizing Shiga antitoxin by mucosal immunization with live vectors. However, since virtually all EHEC associated with HUS cases in the USA express Stx2, alone or in conjunction with Stx1, it is preferable that a vaccine for preventing the severe complications of EHEC infection via elicitation of toxin-neutralizing antibodies should stimulate anti-Stx2 as well as Stx1. It is within the broad scope of the present invention to provide a stabilized plasmid system for expressing Stx2 antigens, alone or in conjunction with Stx1, in an attenuated *S. typhi* live vector.

Other antigens which may be suitably delivered according to the compositions and methods of the present invention include, for example, those for hepatitis B, *Haemophilus influenzae* type b, hepatitis A, acellular pertussis ($_{ac}$P), varicella, rotavirus, *Streptococcus pneumoniae* (pneumococcal), and *Neisseria meningitidis* (meningococcal). See Ellis et al., *Advances in Pharm.*, 39: 393–423, 1997 (incorporated herein by reference).

In one aspect, the antigens encoded by the expression plasmids of the present invention are cancer vaccines.

In another aspect, the antigens encoded by these plasmids are designed to provoke an immune response to autoantigens, B cell receptors and/or T cell receptors which are implicated in autoimmune or immunological diseases. For example, where inappropriate immune responses are raised against body tissues or environmental antigens, the vaccines of the present invention may immunize against the autoantigens, B cell receptors and/or T cell receptors to modulate the responses and ameliorate the diseases. For example, such techniques can be efficacious in treating myasthenia gravis, lupus erythematosis, rheumatoid arthritis, multiple sclerosis, allergies and asthma.

5.8.4.1 The Shiga Toxin Family

Conradi in 1903 first reported that *S. dysenteriae* 1 produced a powerful exotoxin. Because injection of this toxin led to hind limb paralysis of rabbits it was originally called a neurotoxin. Subsequently this toxin, Shiga toxin, was shown to be lethal for certain cells in tissue culture (i.e., it was a cytotoxin). Vicari et al. and then Keusch et al. demonstrated that it also functioned as an enterotoxin.

Scientists now recognize the existence of a family of Shiga cytotoxins which inhibit protein synthesis, leading to cell death for susceptible cells. For many years after the revelation that such toxins were produced by certain *E. coli* strains in addition to the original Shiga toxin produced by *Shigella dysenteriae* type 1, the nomenclature for this family of toxins was confusing. Since early reports described the activity of these toxins on Vero cells (a cell line derived from African green monkey kidney epithelial cells), many investigators called them verotoxins. Others referred to these toxins expressed in *E. coli* as Shiga-like toxins.

The protein toxins are collectively referred to herein as Shiga toxins (Stx), and the genes encoding these toxins are designated as stx with subscripts denoting the group and variant [i.e. $stx_1$ for the Shiga toxin produced by *E. coli* that is essentially identical to that of *Shigella dysenteriae* type 1 (stx), and $stx_2$, $stx_{2c}$, $stx_{2d}$, $stx_{2e}$ for the antigenically distinct group of related toxins].

The structure, biochemistry and antigenicity of Shiga toxins are well described in Melton-Celsa et al., *Eschericia coli* 0157:H7 and *Other Shiga Toxin-producing E. coli Strains*, 1998; Takeda, *Bacterial Toxins and Virulence Factors in Disease*, 1995; Gyles, Canadian *J. of Microbiology*, 38:734, 1992; and O'Brien et al., *Current Topics in Microbiology and Immunology*, 180:165, 1992 (the disclosures of which are incorporated herein by reference).

These Shiga cytotoxins are composed of a single catalytic A subunit of approximately 32 kDa non-covalently associated with a pentameric receptor binding domain of approximately 7.7 kDa B subunits. These subunits are encoded by a single operon of the order stxA-stxB; transcription of the stx and $stx_1$ operons are iron-regulated in both *S. dysenteriae* type 1 and *E. coli*, but no environmental control signals have as yet been determined for any $stx_2$ operon. None of these toxins is encoded on a plasmid; rather they are phage-encoded (Stx1, Stx2, Stx2c, and Stx2d) or are chromosomally encoded (Stx, Stx2e).

As mentioned above, all members of the Shiga toxin family are cytolytic toxins which inhibit protein synthesis within susceptible cells by blocking the binding of elongation factor 1-dependent aminoacyl-tRNA to ribosomes. For all toxins identified from human infections, penetration of susceptible cells by endocytosis follows binding of the holotoxin to the necessary cell surface glycolipid receptor globotriaosyl ceramide ($Gb_3$), trafficking of the toxin to the Golgi apparatus and endoplasmic reticulum, followed by release into the cytoplasm. Shiga toxins are RNA N-glycosidases which depurinate a single adenine from the 28S RNA of the eukaryotic 60S ribosomal subunit, thus inactivating the 60S subunit and eventually leading to cell death.

There are six prototypic members of the Shiga toxin family: Stx, Stx1, Stx2, Stx2c, Stx2d, and Stx2e, which differ from one another immunologically and in toxic activity. Significant detail has been included here to provide background for understanding the significance of point mutations discussed below, which are required for the genetically detoxified holotoxins. The members of the Shiga toxin family differ from one another in 3 fundamental ways, as recently summarized by Melton-Celsa et al., *Eschericia coli* 01 57:H7 and *Other Shiga toxin-producing E. coli strains.*, 1998.

(1) Immunologically: The Shiga toxin family is composed of two serogroups, Stx/Stx1 and Stx2; antisera raised against Stx/Stx1 do not neutralize members of the Stx2 serogroup, as judged by the Vero cell cytotoxicity assay.

(2) Structurally: Stx and Stx1 are essentially identical, differing in a single amino acid at position 45 of the mature A subunit, and the crystal structure for the Stx holotoxin has been solved. The prototype Stx2 is only 55% homologous to residues of the mature A subunit of Stx/Stx1 and 57% homologous to the mature B subunit, which explains why antisera raised against Stx/Stx1 do not neutralize members of the Stx2 group. Within the Stx2 group, Stx2e is most distantly related, sharing 93% amino acid homology to the mature A subunit of Stx2 and 84% homology to the mature B subunit; Stx2c and Stx2d are very similar to Stx2, sharing 99–100% homology in mature A subunit residues and 97% homology in mature B subunit residues.

(3) Cytotoxicity: Stx2 is among the most lethal of the Shiga toxins, with an $LD_{50}$ for mice injected intraperitoneally of 0.5–2 ng. The $LD_{50}$ for Stx1 and Stx2e is 200–400 ng, and 1–5 ng for Stx2d; however, Stx2d is unusual in that this toxin can become activated by murine intestinal mucus to increase the toxicity of the toxin, lowering the $LD_{50}$ to 0.5 ng.

5.8.5 Site-Specific Mutagensis of Shiga Toxins

In one aspect, the invention provides a genetically detoxified Shiga toxin. The detoxification is accomplished by site-specific mutagenesis, introducing two defined and well-separated point mutations altering critical residues within the catalytic site of the A subunit. The invention also introduces two additional defined and well-separated point mutations within the B subunit to alter critical residues within the primary binding site (i.e. SITE I) residing within the cleft formed by adjacent B subunits of the holotoxin pentameric ring.

Prior attempts have been made to alter the lower affinity binding SITE II. However, this binding site has only been identified from molecular modeling studies, and is not extensively supported by mutational studies which favor SITE I binding of the $Gb_3$ receptor. Even if SITE II is an alternate low-affinity binding site allowing entry of our mutant holotoxin into susceptible cells, the inactivation of the catalytic domain will still prevent cell death.

Based on amino acid sequence alignments, X-ray crystallography studies, and molecular modeling studies, essential amino acids have been identified comprising the active site within the catalytic A subunit of Stx, as well as those residues comprising the binding SITE I within the B subunit pentamer of Stx/Stx1. It is the inventor's conclusion that the amino acids essential to the active site are selected from the group consisting of Tyr 77, Tyr 114, Glu 167, Arg 170, and Trp 203. The residues believed to be required for receptor binding to the clefts formed by adjacent B subunits include Lys 13, Asp 16, Asp 17, Asp 18, Thr 21, Glu 28, Phe 30, Gly 60, and Glu 65. These site predictions are consistent with functional studies and in vivo experiments using defined single and double mutations, within individual domains of the holotoxin, introduced by site-specific mutagenesis. A summary of such mutations is presented in Table 1. Based on these data and crystallographic predictions, it is within the broad practice of the invention to provide expression plasmids encoding Shiga toxins having two specific sets of point mutations within both the A and B subunits to create non-toxic mutant Stx2 holotoxins for use as vaccines, such as by expression within attenuated S. typhi live vectors such as CVD908-htrA.

The carrier or carriers must be pharmaceutically acceptable in the sense that they are compatible with the therapeutic ingredients and are not unduly deleterious to the recipient thereof. The therapeutic ingredient or ingredients are provided in an amount and frequency necessary to achieve the desired immunological effect.

The mode of administration and dosage forms will affect the therapeutic amounts of the compounds which are desirable and efficacious for the vaccination application. The bacterial live vector materials are delivered in an amount capable of eliciting an immune reaction in which it is effective to increase the patient's immune response to the expressed mutant holotoxin or to other desired heterologous antigen(s). An immunizationally effective amount is an amount which confers an increased ability to prevent, delay or reduce the severity of the onset of a disease, as compared to such abilities in the absence of such immunization. It will be readily apparent to one of skill in the art that this amount will vary based on factors such as the weight and health of the recipient, the type of protein or peptide being expressed, the type of infecting organism being combatted, and the mode of administration of the compositions.

The modes of administration may comprise the use of any suitable means and/or methods for delivering the bacterial live vector vaccines to a corporeal locus of the host animal where the bacterial live vector vaccines are immunostimulatively effective.

Delivery modes may include, without limitation, parenteral administration methods, such as subcutaneous (SC) injection, intravenous (IV) injection, transdermal, intramuscular (IM), intradermal (ID), as well as non-parenteral, e.g., oral, nasal, intravaginal, pulmonary, opthalmic and/or rectal administration.

The dose rate and suitable dosage forms for the bacterial live vector vaccine compositions of the present invention

TABLE 1

SITE-SPECIFIC MUTAGENESIS STUDIES

| SUBUNIT | TOXIN | MUTATION | DROP IN CYTOTOXICITY | DROP IN LETHALITY | NEUTRALIZING ANTIBODIES |
|---|---|---|---|---|---|
| A | Stx1 | Leu201 → Val + of residues 202–213 | NO cytotoxicity | — | — |
| | Stx1 | Glu167 → Asp | $10^3$ | — | — |
| | Stx1 | Arg170 → Leu | $10^3$ | — | — |
| | Stx2 | Glu167 → Asp | $10^3$ | — | — |
| | Stx2e | Glu167 → Asp | $10^4$ | — | — |
| | Stx2e | Arg170 → Lys | 10 | — | — |
| | Stx2e | Glu167 → Asp Arg170 → Lys | $10^4$ $10^4$ | — — | — — |
| | Stx2e | Glu167 → Gln | $10^6$ | $10^4$ | Y |
| B | Stx | Asp16 → His + Asp17 → His | NO cytotoxicity | — | — |
| | Stx | Arg33 → Cys | $10^8$ | — | — |
| | Stx | Gly60 → Asp | $10^6$ | — | — |
| | Stx1 | Phe30 → Ala | $10^5$ | 10 | Y |
| | Stx2 | Ala42 → Thr | $10^3$–$10^4$ | Y | Y |
| | Stx2 | Gly59 → Asp | $10^3$–$10^4$ | Y | Y |

5.9 Pharmaceutical Formulations

It is contemplated that the bacterial live vector vaccines of the present invention will be administered in pharmaceutical formulations for use in vaccination of individuals, preferably humans. Such pharmaceutical formulations may include pharmaceutically effective carriers, and optionally, may include other therapeutic ingredients, such as various adjuvants known in the art.

may be readily determined by those of ordinary skill in the art without undue experimentation, by use of conventional antibody titer determination techniques and conventional bioefficacyl biocompatibility protocols. Among other things, the dose rate and suitable dosage forms depend on the particular antigen employed, the desired therapeutic effect, and the desired time span of bioactivity.

The bacterial live vector vaccines of the present invention may be usefully administered to the host animal with any other suitable pharmacologically or physiologically active agents, e.g., antigenic and/or other biologically active substances.

Formulations of the present invention can be presented, for example, as discrete units such as capsules, cachets, tablets or lozenges, each containing a predetermined amount of the vector delivery structure, or as a suspension.

6. EXAMPLES

An isogenic series of expression plasmids composed of individual cassettes has been constructed for use in bacterial live vector vaccines, such as *E. coli* and *Salmonella*. With the exception of ribosomal binding sites (RBS), the key genetic loci controlling transcription initiation and termination, plasmid replication, or encoding expressed proteins are contained within defined restriction fragments, as depicted by the representative plasmid diagram of pGEN2 seen in FIG. 1A. The basic structure of these expression plasmids will first be highlighted and then the data demonstrating the function of each locus within the attenuated vaccine strain CVD908-htrA will be summarized.

6.1 pGEN Structure

Transcription of any heterologous antigen to be expressed within CVD908-htrA is primarily controlled by an inducible promoter contained on an EcoRI-BglII cassette. Since the expression plasmids were initially modeled after pTETnir15, early versions carried the anaerobically-activated nir15 promoter ($P_{nir15}$). However, this promoter has been replaced with a more tightly regulated osmotically controlled promoter $P_{ompC}$ which is easily manipulated in vitro by varying the concentration of NaCl.

Heterologous antigens are contained on a BglII-AvrII cassette, flanked by an optimized RBS at the 5,'-proximal end and a trpA transcriptional terminator at the 3'-distal end of this cassette. The origin of replication for these expression plasmids has been designed as an AvdII-BglII cassette, and is protected from read-through transcription originating in flanking regions. These cassettes carry an extremely efficient derivative of the T1T2 transcriptional terminator at one terminus with the trpA transcriptional terminator from the heterologous antigen cassette at the opposite end of the replication cassette.

The flanking BglII and SpeI sites (see FIG. 2) between the replication cassette and the selection cassette are intended for insertion of a plasmid maintenance function, such as the par locus from pSC101. The selection cassettes contained within the plasmids are contained within SpeI-XbaI cassettes, and can, for example, be used to encode resistance to carbenicillin (the bla gene) or resistance to tetracycline (the tetA gene, see FIG. 1).

The drug resistance cassette can be replaced with the ssb gene encoding the essential single stranded binding protein of *Salmonella typhi* CVD908-htrA.

The flanking XbaI and EcoRI sites between the selection cassette and $P_{ompC}$ are intended for insertion of additional maintenance functions, including a PSK locus such as hok-sok (see FIGS. 1 and 2), or an additional partition function such as the parA locus from pR1 (see FIG. 7).

6.2 Modified ompC Promoter

It was intended that any promoter controlling transcription of a heterologous gene be responsive to an environmental signal of biological relevance. For the expression plasmids described here, an ompC promoter cassette ($P_{ompC}$) from *E. coli* was used, which is induced by increases in osmolarity. Construction of this cassette was based on the published sequence of $P_{ompC}$ published by Norioka et al (Norioka et al. 1986) and was carried out using synthetic primers to create a 459 bp EcoRI-BglII cassette in which the natural RBS was removed.

To confirm that this promoter was osmotically controlled within CVD 908-htrA, a derivative of pTETnir15 was constructed in which $P_{nir15}$-toxC was replaced by a cassette comprised of $P_{ompC}$ driving expression of a promoterless aphA-2 cassette conferring resistance to kanamycin. This plasmid, designated pKompC, was introduced into CVD 908-htrA by electroporation, and recipients were screened for resistance to kanamycin on LB medium. The osmotically regulated expression of aphA-2 was determined by inoculating CVD 908-htrA(pKompC) into 50 ml of supplemented nutrient broth (NB) containing increasing concentrations of kanamycin from 0 to 300 μg/ml; a parallel set of cultures were set up with the identical ranges of kanamycin added, but also containing 10% sucrose to induce $P_{ompC}$. Cultures were incubated overnight at 37° C., and the O.D.$_{600}$ was measured. Results are reported in the Table 2, Experiment 1.

TABLE 2 shows induction with osmolarity of the promoter $P_{ompC}$ controlling expression of resistance to kanamycin, within the attenuated *S. typhi* live vector CVD 908-htrA.

TABLE 2

| EXPERIMENT[1] | | | EXPERIMENT[2] | | |
|---|---|---|---|---|---|
| Concentration of kanamycin (μg/ml) | Low osmolarity (O.D.$_{600}$) | 10% sucrose (O.D.$_{600}$) | Concentration of kanamycin (μg/ml) | Low osmolarity (O.D.$_{600}$) | 300 mM NaCl (O.D.$_{600}$) |
| 0 | 0.92 | 0.35 | 0 | 0.95 | 1.04 |
| 50 | 0.13 | 0.35 | 200 | 0.04 | 0.99 |
| 100 | 0.07 | 0.31 | 400 | 0.02 | 0.96 |
| 200 | 0.03 | 0.21 | 600 | 0.01 | 0.92 |
| 300 | 0.02 | 0.19 | 800 | 0.01 | 0.92 |

[1]A culture of CVD908-htrA(pKompC) was set up in LB broth supplemented with 0.0001% (w/v) 2,3-dihydroxybenzoic acid (DHB) and 50 μg/ml of kanamycin, and was incubated for 16 hr at 37° C. This initial culture was then diluted 1:10 into fresh medium and incubated at 37° C. for two hrs to provide a seed culture of exponentially growing bacteria. 50 μl of this culture were then inoculated into 50 ml Nutrient Broth (NB) cultures supplemented with DHB as above, but with increasing concentrations of kanamycin; a parallel set of cultures were set up with the identical ranges of kanamycin added, but also containing 10% sucrose to hopefully induce $P_{ampC}$. Cultures were incubated overnight at 37° C., and the O.D.$_{600}$ was measured.
[2]A culture of CVD908-htrA(pKompC) in supplemented LB broth and kanamycin was incubated for 16 hr at 37° C., diluted 1:10 into fresh medium, and incubated at 37° C. for two hrs to provide a seed culture of exponentially growing bacteria. 100 μl aliquots of this culture were then inoculated into 50 ml NB broth cultures containing increasing concentrations of kanamycin from 200 to 800 μg/ml; a parallel set of cultures were set up containing 300 mM NaCl, and all cultures were incubated at 37° C. for 16 hr. and the O.D.$_{600}$ was measured.

Regardless of selective pressure using kanamycin, the presence of 10% sucrose had an inhibitory effect on the growth of CVD 908-htrA(pKompC). However, the results suggested that *E. coli* $P_{ompC}$ was osmotically controlled when driving aphA-2 gene expression within CVD 908-htrA (pKompC). To confirm this, CVD 908-htrA(pKompC) was inoculated into 50 ml of supplemented NB broth, containing increasing concentrations of kanamycin from 200 to 800 μg/ml; a parallel set of cultures was again set up containing 300 mM NaCl to induce $P_{ompC}$. Cultures were incubated at 37° C. for 16 hr, and results are reported in Table 2, Experiment 2. It was confirmed that $P_{omp}$-driven expression of the aphA-2 gene within CVD 908-htrA confers resistance to kanamycin at levels up to 800 µg/ml in an osmotically regulated manner.

The aph gene cassette was then replaced with a 756 bp BglII-NheI cassette containing the gfpuv allele encoding GFPuv. During the visual screening of *E. coli* colonies sub-illuminated with ultraviolet light, one very brightly fluorescing colony and another representative fluorescent colony were chosen for further study, designated clone 1 and clone 3, respectively. Upon purification of the plasmids involved, it was determined that clone 1 contained a plasmid that no longer carried a BglII site separating $P_{ompC}$, and gfpuv, while clone 3 carried the expected BglII site. We examined the induction of GFP expression when clones 1 and 3 are grown on nutrient agar in the presence or absence of NaCl, and determined by visual inspection that clone 3 displayed very little fluorescence when grown on nutrient agar containing no NaCl but fluoresced brightly when plated on nutrient agar containing 300 mM NaCl (data not shown). Clone 1, however, had a higher background level of fluorescence when uninduced, but fluoresced intensely when induced with 300 mM NaCl. To rule out mutations within the gfpuv gene which might affect fluorescence, we replaced $P_{ompC}$ from clone 1 with $_{ompC}$ from clone 3, and confirmed the expected decrease in fluorescence as judged by sub-illumination (data not shown). We therefore concluded that differences in observed fluorescence were controlled by two genetically distinct versions of the $P_{ompC}$ promoter, which we designate as $P_{ompC1}$ (higher transcription levels with less osmotic control) and $P_{ompC3}$ (moderate transcription levels with osmotic control similar to that observed for the $P_{ompC}$-aph cassette described above); we designate the plasmids containing these expression cassettes as pGFPompC1 and pGFPompC3, respectively.

To quantify the differences in induced and uninduced expression of gfpuv controlled by $P_{ompC1}$ and $P_{ompC}$, GFPuv synthesis was monitored within both *E. coli* DH5α and *S. typhi* CVD 908-htrA using flow cytometry. This powerful technique has the unique advantages of allowing rapid measurement of GFPuv expression within large numbers of individual bacteria, as well as accurately determining the mean intensity of fluorescence due to GFPuv synthesis within each bacterial population analyzed. To accomplish this, pGFPompC1 and pGFPompC3 were introduced by electroporation, and colonies were isolated on supplemented 1× LB agar containing 100 µg/ml of carbenicillin grown at 30° C. for 48 hr. Isolated colonies were then grown up and cultures frozen down as master stocks. Fresh colonies were then inoculated into either supplemented nutrient broth or supplemented nutrient broth containing 150 mM NaCl, and grown at 37° C./250 rpm for 24 hr; the difference in O.D.$_{600}$ for any culture was never greater than 0.07. Induction of expression of gfpuv, controlled by $P_{ompC1}$ and $P_{ompC3}$, was analyzed by flow cytometry, and results are presented in Table 3.

TABLE 3 shows a comparison of induction of $P_{ompC1}$ and $P_{ompC3}$, controlling expression of GFPuv, within the host strains *E. coli* DH5α and CVD 908-htrA.[1]

TABLE 3

| STRAIN | Low osmolarity (O.D.$_{600}$) | Mean Fluorescence Intensity | 150 mM NaCl (O.D.$_{600}$) | Mean Fluorescence Intensity | Induction Ratio |
|---|---|---|---|---|---|
| DH5α | 0.61 | 0.28 | 0.95 | 0.29 | NA[3] |
| DH5α (pGFPompC1) | 0.56 | 4.45 | 0.72 | 7.69 | 1.7 |
| DH5α (pGFPompC3) | 0.58 | 1.77 | 0.73 | 4.21 | 2.4 |
| CVD 908-htrA | 0.58 | 0.27 | 0.65 | 0.26 | NA |
| CVD 908-htrA (pGFPompC1) | 0.60 | 5.37 | 0.54 | 23.4 | 4.4 |
| CVD 908-htrA (pGFPompC3) | 0.54 | 2.56 | 0.53 | 17.1 | 6.7 |

[1]All strains were streaked from frozen master stocks onto 2X LB agar supplemented with DHB and 50 µg/ml of carbenicillin, and incubated for 36 hr at 30° C. Isolated colonies were pooled into 300 µl of NB broth supplemented with DHB and carbenicillin, from which 25 µl were inoculated into 25 ml supplemented NB broth, with and without 150 mM NaCl and incubated at 37° C., 250 rpm for 24 hr. Bacteria were then pelleted, resuspended in 1 ml PBS pH 7.4, and then diluted 1:1000 into PBS for analysis by flow cytometry.
[2]Defined as the ratio of mean fluorescent intensity measured after induction with 150 mM NaCl, divided by basal level of mean fluorescent intensity measured at low osmolarity.
[3]NA = not applicable.

The basal level of expression for the $P_{ompC1}$-gfpuv cassette is 2.5 times higher than for the $P_{ompC3}$-gfpuv cassette, when expressed in DH5α, and 2.1 times higher when expressed within CVD 908-htrA; however, the basal level of fluorescence detected for synthesis of GFPuv never exceeded a mean fluorescent intensity of 5.37, regardless of host background. If we define induction ratio as the ratio of mean fluorescent intensity measured after induction, divided by basal level of mean fluorescent intensity, it was observed that when induced with 150 mM NaCl, $P_{ompC1}$ and $P_{ompC3}$ displayed within DH5α induction ratios of 1.7 and 2.4 respectively. Surprisingly, the induction ratio for $P_{ompC1}$ when measured in CVD 908-htrA was 4.4, and produced a maximum mean fluorescence intensity of 23.4 for these experiments. Although the induction ratio for $P_{ompC3}$ within CVD 908-htrA was 6.7, the mean fluorescence intensity of 17.1 was lower than measured for $P_{ompC1}$. Based on these data, it appears that $P_{ompC1}$ is the strongest and yet osmotically controlled of the two ompC promoters. $P_{ompC1}$ was therefore chosen for synthesis of the widest possible range of heterologous test antigen to examine the effects of such synthesis on plasmid stability.

These data clearly show that when driving expression of gfpuv within the live vector strain CVD 908-htrA, $P_{ompC1}$ and $P_{ompC3}$ are inducible with increasing osmolarity, although the basal level of transcription is still noteworthy in both cases. The results observed under conditions of low osmolarity further support our observations using solid media that $P_{ompC1}$ drives higher heterologous antigen expression than $P_{ompC3}$. Since $P_{ompC3}$ was noted to possess the intended 3'-terminal BglII site, which was not detected for $P_{ompC1}$, we determined the nucleotide sequence for $P_{ompC1}$ to perhaps detect point mutation(s) which might explain the strength of $P_{ompC}$. The only differences identified were located at the 3'-terminus of the cassette. The intended sequence within this region was 5'- . . . catataacAGATCTtaatcatccacAGGAGGatatctgATG-3'(SEQ ID NO: 4) (from left to right, upper case denotes the BglII site, ribosome binding site, and GFPuv start codon respectively); the actual sequence proved to be 5'- . . . catataacAGATCGATCTtaaAcatccacAGGAGGAtAtctgAT- G-3(SEQ ID NO: 5) (inserted or changed bases denoted with underlined bold upper case). These changes detected within the ompC1 promoter sequence are apparently responsible for increasing the observed strength of $P_{ompC1}$ by an unknown mechanism, since neither the basic ompC promoter sequence, nor the optimized ribosome binding site have been spontaneously altered.

6.3 Origins of Replication and Selection Cassettes

The success of expressing potentially toxic or otherwise problematic heterologous antigens within CVD908-htrA depends on the copy number of the expression plasmid. In addition, observed immune responses to a given heterologous antigen are affected by the copy number of the gene(s) encoding the antigen, with chromosomally expressed antigens eliciting poorer immune responses when compared to plasmid-based expression.

An optimized immune response will depend on multicopy plasmid-based expression of the heterologous antigen(s) from plasmids with the appropriate copy number.

Since the appropriate copy number for a given heterologous gene cannot be known a priori, the present invention provides a set of expression plasmids which contain the origins of replication oriE1 (amplified from pAT153; copy number ~60), ori15A (amplified from pACYC184; copy number ~15), and ori101 (amplified from pSC101; copy number ~5). These self-contained replication cassettes are all carried on BglII-BamHI fragments, and are depicted for a set of 3 tetracycline-resistance expression plasmids shown in FIGS. 1A–1C.

Expression of the $P_{ompC1}$-controlled gfpuv expression cassette contained on these expression plasmids was analyzed using flow cytometry. These experiments were designed to detect whether differences in the level of observed fluorescence could be correlated with the expected copy number of a given expression plasmid. CVD908-htrA strains carrying pGEN2, pGEN3, and pGEN4 were streaked onto the rich medium SuperAgar supplemented with DHB and 20 µg/ml tetracycline where appropriate. SuperAgar was used because it is a very rich medium (3× LB agar). Plates were incubated at 30° C. to reduce the toxicity of GFP synthesis and allow bacteria to grow luxuriously on the plates. Isolated colonies were then inoculated into 45 ml of SuperBroth supplemented with DHB and 20 µg/ml tetracycline where appropriate, and incubated at 37° C. for 16 hr. Bacteria were concentrated by centrifugation and resuspended in 1 ml of sterile PBS, pH=7.4, and diluted 1:100 in PBS, pH=7.4 prior to FACS analysis. Bacteria were analyzed by flow cytometry, as described above, for two independent growth experiments, and results are displayed in Table 4 at the end of this section.

These data support the conclusion that overexpression of GFPuv within CVD908-htrA is toxic to the bacteria. As the theoretical copy number increases for the plasmids pGEN4, pGEN3, and pGEN2 expressing GFPuv under identical growth conditions from the identical $P_{ompC1}$ promoter, the percentage of the growing population which fluoresces declines. It is expected that the "dim" bacteria are not viable bacteria and may no longer contain the expression plasmid, since these cultures were grown in the presence of 20 µg/ml tetracycline. It is noted, however, that when streaked onto solid medium and grown at 37° C. for 24–36 hr, CVD908-htrA(pGEN2) grows poorly and fails to produce isolated colonies, while CVD908-htrA(pGEN3) and CVD908-htrA (pGEN4) grow quite well and produce intensely fluorescing isolated colonies.

GFPuv is employed herein as representative of other problematic heterologous antigens which would be of interest to include in a bacterial live vector, such as the S. typhi-based live vector; however, it will be appreciated that GFPuv can be replaced by any non-metabolic protein or peptide antigen.

The data above show that although use of medium-copy expression plasmids containing oriE1 replicons can be of use in expression of some antigens, expression of antigens of higher toxicity will be more successfully expressed from lower copy number plasmids which employ origins of replication yielding average copy numbers between 2 and 30, such as ori10 or ori15A origins of replication.

TABLE 4

| | Experiment 1 | | | | Experiment 2 | | | |
|---|---|---|---|---|---|---|---|---|
| Strain | Percent Dim Bacteria | Mean Fluorescence Of Dim Bacteria (Relative Units) | Percent Fluorescing Bacteria | Mean Fluorescence (Relative Units) | Percent Dim Bacteria | Mean Fluorescence Of Dim Bacteria (Relative Units) | Percent Fluorescing Bacteria | Mean Fluorescence (Relative Units) |
| CVD908-htrA | 100 | 0.6 | 0 | 0 | 100 | 0.3 | 0 | 0 |
| CVD908-htrA(pGEN2) | 19.9 | 0.1 | 80.1 | 38.5 | 37.2 | 0.3 | 62.8 | 10.1 |
| CVD908-htrA(pGEN3) | 17.1 | 0.1 | 82.9 | 28.1 | 4.9 | 0.2 | 95.1 | 8.28 |
| CVD908-htrA(pGEN4) | 12.1 | 0.1 | 88.0 | 22.4 | 9.4 | 0.3 | 90.6 | 4.25 |

6.4 The hok-sok Antisense Post-Segregational Killing Locus

Using the polymerase chain reaction, the hok-sok PSK genes were amplified using the multiple antibiotic resistance R-plasmid pR1 as the template in these reactions. All initial attempts to clone this locus onto either high or medium copy number plasmids were unsuccessful. In order to directly select for the hok-sok locus during subcloning, a set of primers was designed for use in overlapping PCR reactions such that the final product was a fragment containing a genetic fusion of the hok-sok locus from pR1 and a promoterless tetA gene from pBR322 encoding resistance to tetracycline. This cassette was engineered such that transcription of the hok gene would continue into tetA; the two loci within this cassette were separated by an XbaI restriction site for future manipulations.

Construction of this cassette not only allowed for direct selection of the hok-sok locus, but also allowed for confirmation that the PSK function would operate in S. typhi CVD908-htrA. After electroporation of plasmids carrying the cassette into CVD908-htrA, transformants could be selected using tetracycline. Successful recovery of isolated colonies indicates successful synthesis of the hok-tetA mRNA, and successful synthesis of the antisense sok RNA to prevent translation and synthesis of Hok, which would kill the bacteria. Recovery of the hok-sok-tetA cassette then became straightforward, and was easily incorporated into our expression plasmids to create the selectable marker cassette of the plasmids pGEN2, pGEN3, and pGEN4 depicted in FIGS. 1A–1C.

Experiments were then initiated to determine the effect of the hok-sok PSK function on the stability of expression plasmids containing ori1 and the resistance marker bla encoding β-lactamase which confers resistance to carbenicillin. The hok-sok cassette was inserted into the pAT153-based expression plasmid pTETnir15, in which the Pnir15-toxC heterologous antigen cassette was replaced with our $P_{ompC1}$-gfpuv cassette, creating the plasmids pJN72 (without hok-sok) and pJN51 (with hok-sok). An additional set of plasmids was created by replacing $P_{ompC}$ with the weaker promoter $P_{ompC3}$, creating pJN10 and pJN12; the structures of these four isogenic plasmids are represented in FIG. 2. CVD908-htrA strains carrying either pJN72, pJN51, pJN10, or pJN12 were streaked onto the rich medium SuperAgar supplemented with DHB and 100 μg/ml carbenicillin, and plates were incubated as above for the pGEN plasmids at 30° C. to reduce the toxicity of GFPuv synthesis and allow bacteria to grow luxuriously on the plates.

Isolated colonies were then inoculated into 45 ml of Super broth supplemented with DHB and 100 μg/ml carbenicillin and grown at 37° C. for 24 hours for analysis by flow cytometry of fluorescence. A second independent experiment was carried out exactly as the first, except isolated colonies were suspended in 500 μl of Super broth and 250 μl each inoculated into 45 ml paired Super broth cultures with or without 300 mM NaCl added to induce the $P_{ompC1}$-gfpuv cassettes; cultures were incubated at 37° C. for 48 hrs and again analyzed by flow cytometry; and results for both experiments are displayed in Table 5. Fluorescence histograms for uninduced and induced expression plasmids from experiment 2 are represented in FIGS. 3A–3H.

increases; however, since multicopy plasmids are involved, relatively few bacteria succeed in losing all resident plasmids, but the average copy number of pJN72 per bacterium drops.

Quantitation by flow cytometry of GFPuv production for an uninduced population of healthy growing CVD 908-htrA (pJN72) indicates that the majority of bacteria express GFPuv and few non-fluorescing cells are detected (FIG. 3A). However, increasing production of GFPuv by induction of the $P_{ompC1}$-gfpuv cassette increases the metabolic stress on CVD 908htrA(pJN72), and although the production of GFP doubles, the percentage of non-fluorescent bacteria increases as more plasmids are lost from the population (FIG. 3B).

In a similar population of growing CVD 908-htrA (pJN51), each bacterium carries multicopy plasmids encoding both GFPuv and a PSK function. The frequency of plasmid loss for pJN51 remains the same as for pJN72, but in this case as individual bacteria lose copies of the expression plasmid, the 1:1 stoichiometry between the mRNA levels of hok and sok is disturbed, and production of Hok leads to cell death; therefore, the only CVD 908-htrA (pJN51) bacteria that will grow rapidly will be those which retain all of their expression plasmids. Accordingly, it is not surprising that quantitation by flow cytometry of GFPuv production for an uninduced population of healthy growing CVD 908-htrA(pJN51) now detects a population of fluorescing bacteria which displays levels of GFPuv fluorescence equivalent to those observed for CVD 908-htrA (pJN72) grown under inducing conditions (FIG. 3C vs FIG. 3B); however, the percentage of non-fluorescing bacteria rises to over half the overall population of organisms.

Figure 2A:
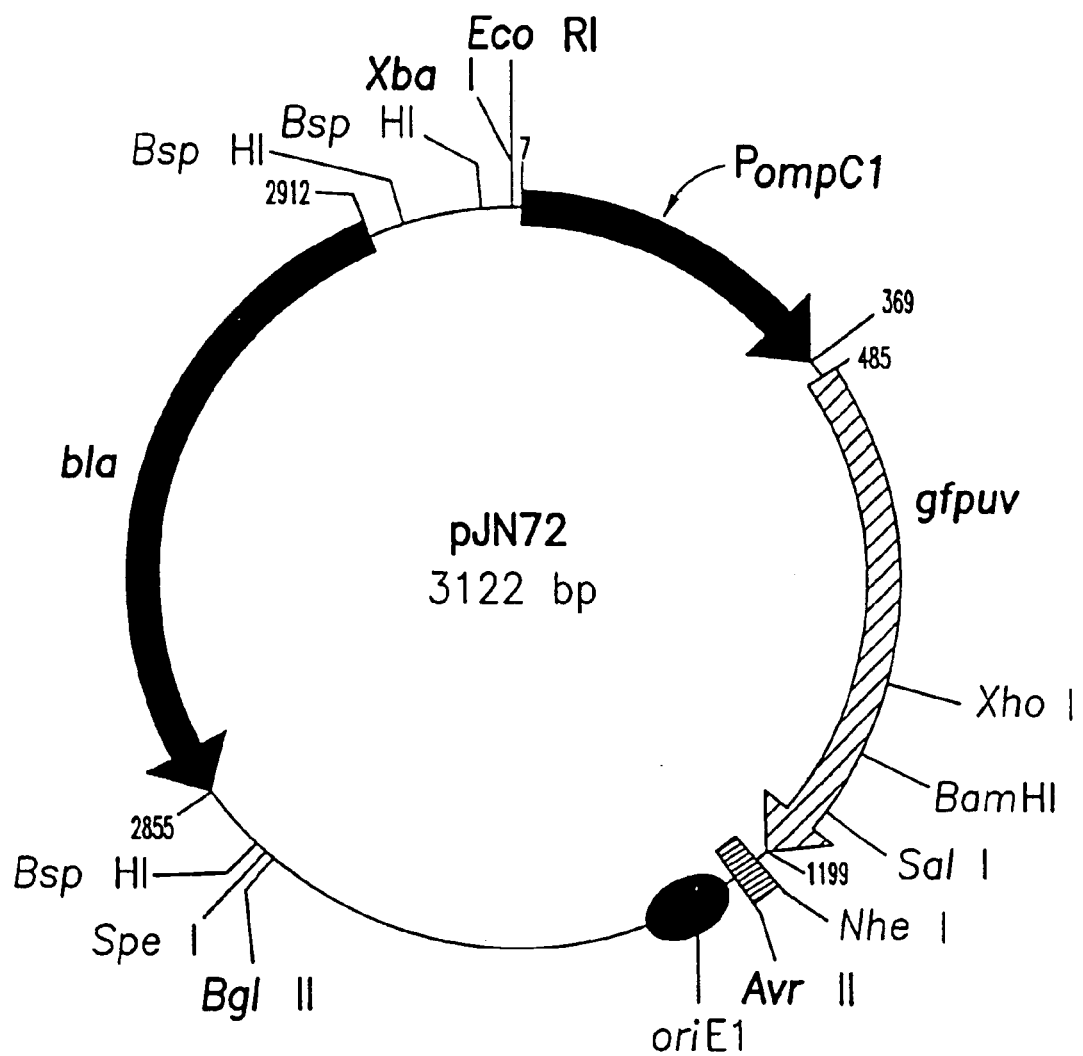
Figure 2B:
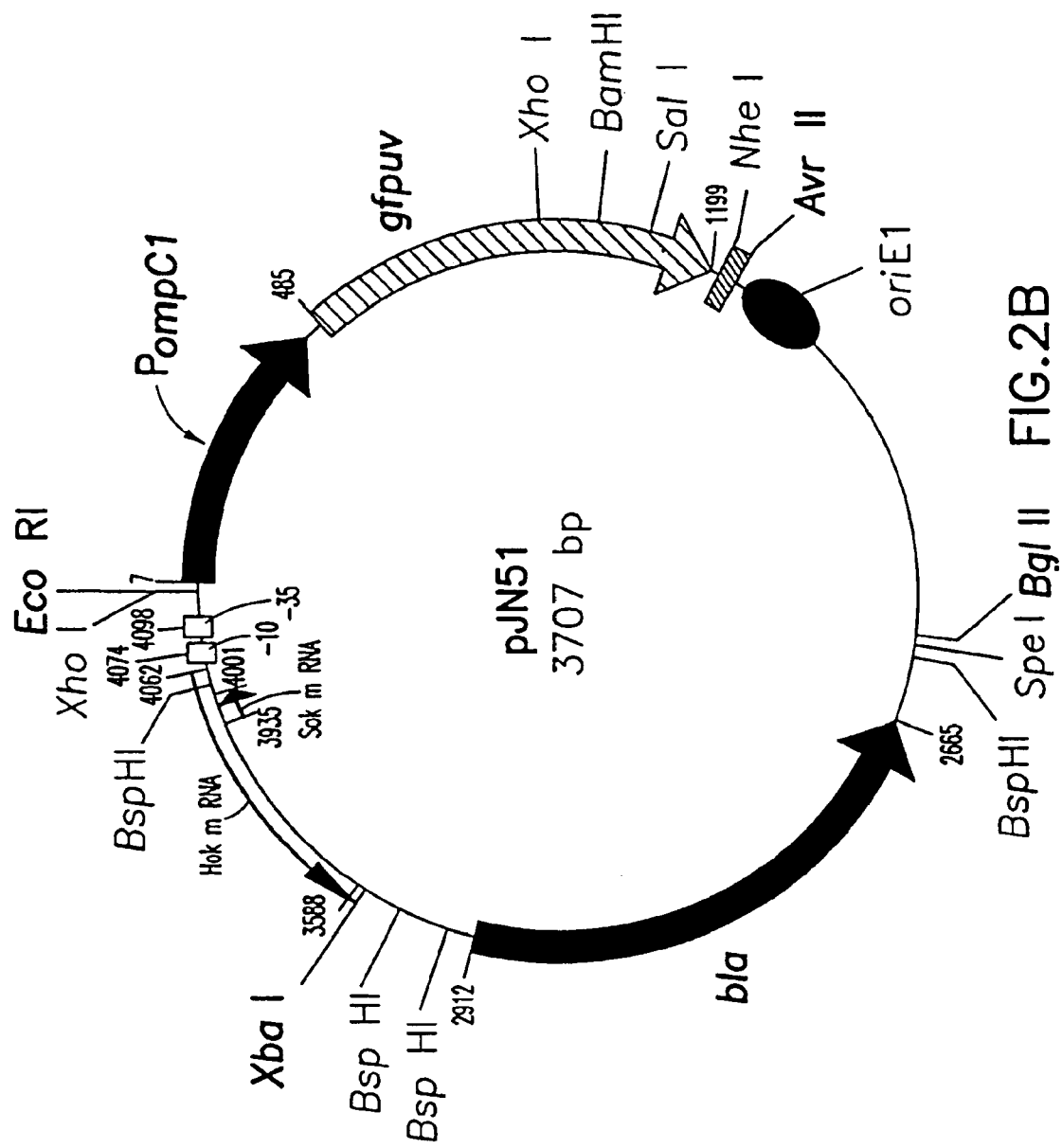
Figure 2C:
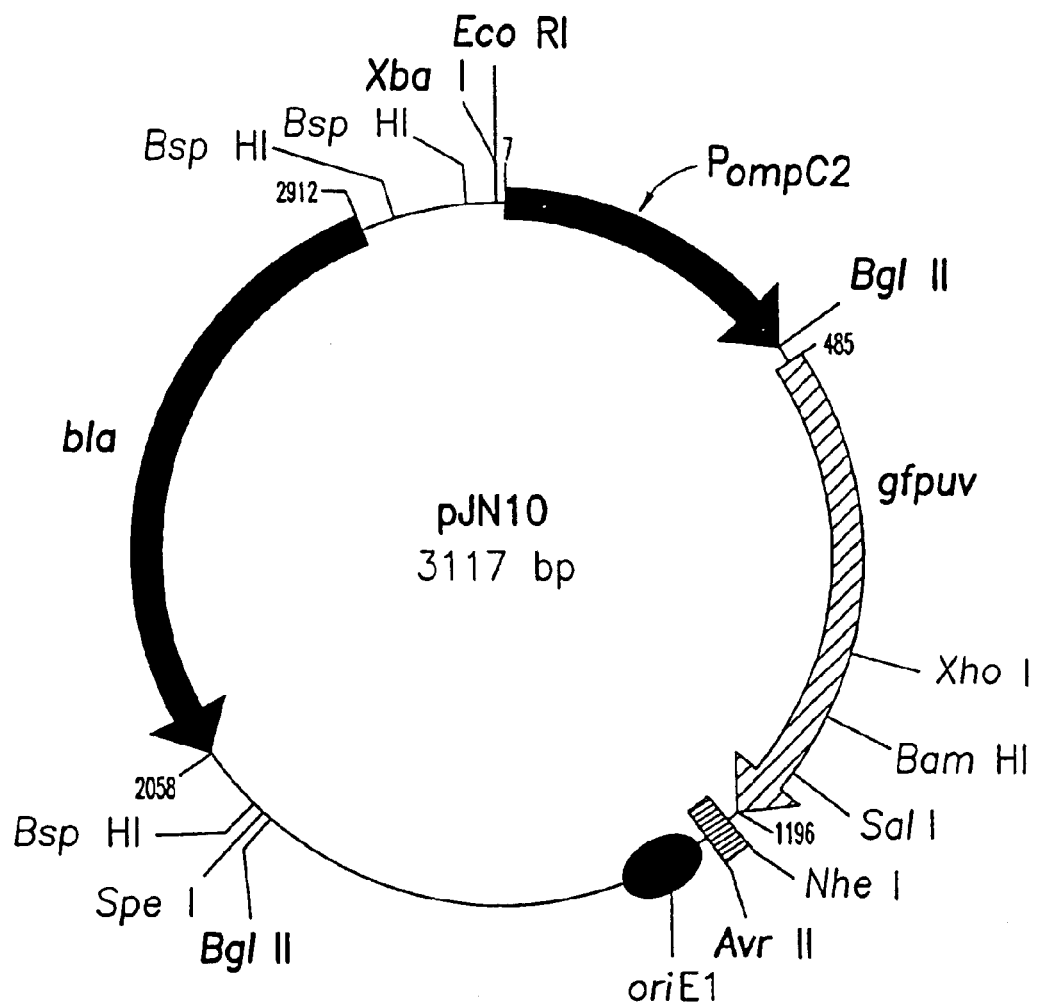
Figure 2D:
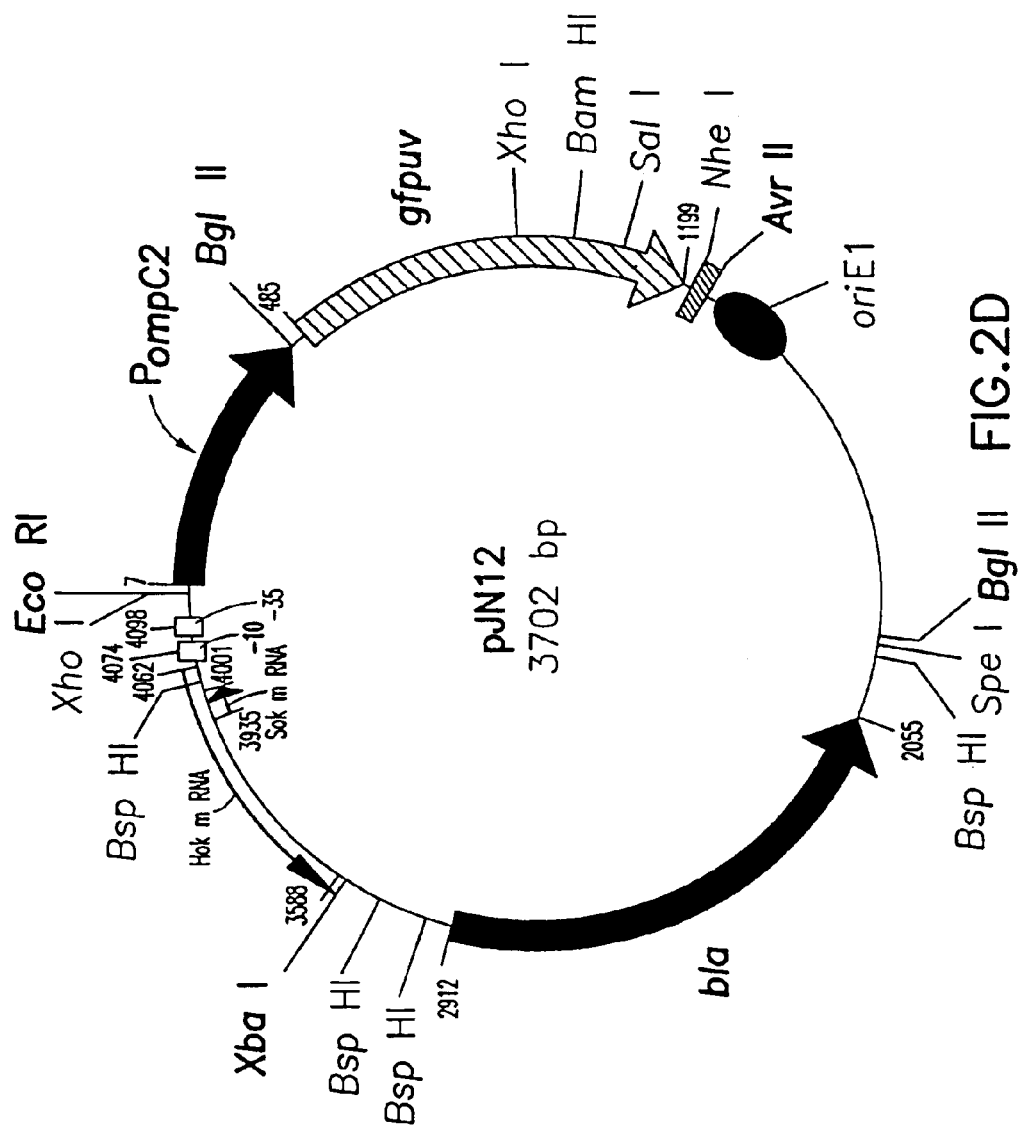

Increasing production of GFPuv in this population by induction of the $P_{ompC1}$-gfpuv cassette in CVD 908-htrA (pJN51) again increases the metabolic stress on the live vector, but now the percentage of non-fluorescent bacteria almost completely overtakes the few fluorescing bacteria as many plasmids are presumably lost from the population and bacteria are killed (FIG. 2D).

TABLE 5

| | Experiment 1 | | | | | Experiment 2 | | | |
| --- | --- | --- | --- | --- | --- | --- | --- | --- | --- |
| Strain | Percent Dim Bacteria | Mean Fluorescence Of Dim Bacteria | Percent Fluorescing Bacteria | Mean Fluorescence | O.D.$_{600}$ | +/− 300 mM NaCl | % Dim Bacteria | Mean Fluorescence Dim Bacteria | % Fluorescing Bacteria | Mean Fluorescence |
| CVD908-htrA | 100 | 0.3 | | | 0.73 | − | 100 | 0.3 | 0 | 0 |
| CVD908-htrA(pJN72) | 3.1 | 0.2 | 96.9 | 10.2 | 0.75 | − | 2.3 | 0.3 | 97.7 | 11.7 |
| | | | | | 0.89 | + | 22.2 | 0.3 | 77.8 | 22.5 |
| CVD908-htrA(pJN51) | 58.1 | 0.3 | 41.9 | 6.29 | 0.62 | − | 56.3 | 0.3 | 43.7 | 18.4 |
| | | | | | 0.82 | + | 95.4 | 0.3 | 4.6 | 21.0 |
| CVD908-htrA(pJN10) | 5.4 | 0.2 | 94.6 | 7.43 | 0.72 | − | 1.7 | 0.3 | 98.3 | 8.3 |
| | | | | | 0.96 | + | 29.9 | 0.3 | 70.1 | 19.8 |
| CVD908-htrA(pJN12) | 18.9 | 0.2 | 81.1 | 6.60 | 0.47 | − | 45.2 | 0.3 | 54.8 | 16.4 |
| | | | | | 0.68 | + | 95.6 | 0.3 | 4.4 | 13.2 |

These flow cytometry results can be explained as follows: expression of GFPuv (or other potentially detrimental heterologous antigen) from a multicopy expression plasmid such as pJN72 increases the metabolic stress on the CVD 908-htrA(pJN72) live vector, and increases plasmid instability in the absence of selection. Since the selectable marker of the expression plasmid encodes the secreted enzyme β-lactamase, then as time increases the concentration of carbenicillin in the surrounding medium declines, selective pressure decreases, and the frequency of plasmid loss One would expect that if a weaker promoter is used to control expression of GFPuv, the overall fluorescence of the population would be decreased (compared to that observed for a similar population of organisms grown with a strong promoter expressing GFPuv under identical conditions), and the percentage of non-fluorescent bacteria should drop due to the overall drop in GFPuv synthesis. However, as seen in FIGS. 3E–3H, use of the weaker $P_{ompC3}$-gfpuv cassette did not significantly improve the viability of induced bacteria carrying a killing system, even though overall expression of GFPuv was reduced.

It is concluded that in order to maximize the percentage of a population of live vectors expressing the heterologous antigen of choice, it is not sufficient only to incorporate a PSK function into a given expression plasmid, whether it be a drug resistance marker, the asd system, an alternate ssb system, or the hok-sok killing system. In addition to optimizing copy number and expression levels, the segregation frequencies of these plasmids must also be improved to ensure that each daughter cell in an actively growing population will inherit at least one expression plasmid and those that do not will be killed and removed from the population. It is therefore within the scope of the present invention to provide an expression plasmid having a PSK function and further having optimized copy number and/or expression levels, coupled with incorporation of one or more SEG functions.

6.5 Complementation-based Killing System

It is also within the broad scope of the present invention to provide an expression plasmid comprising a complementation-based killing system, for example, a system involving the deletion of the chromosomal ssb locus of CVD908-htrA by homologous recombination, and trans-complementation of this lesion using multicopy plasmids carrying functional ssb.

To carry out such constructions requires cloning the relevant section of the *S. typhi* chromosome encompassing the ssb gene and flanking sequences, into which specific deletions can be introduced for chromosomal mutagensis.

Since our original submission, substantial progress has been made in the sequenceing of the *Salmonella typhi* chromosome at the Sanger Centre in London. The Sanger Centre is a genome research center set up in 1992 by the Wellcome Trust and the Medical Research Council in order to further our knowledge of genomes. Among other projects, the Sanger Centre is sequencing the 4.5 Mb genome of *S. typhi*, in collaboration with Gordon Dougan of the Department of Biochemistry, Imperial College, London. They are sequencing strain CT18, a highly pathogenic, multiple drug resistant strain isolated from a typhoid patient in Cho Quan Hospital, Ho Chi Minh City, Vietnam. This strain is known to harbor pVN100 (a 130 kb multidrug resistance plasmid) and a cryptic 80 kb plasmid. The genome is being sequenced by a whole genome shot gun approach using a 2 kb pUC library, generated inhouse from chromosomal DNA supplied by Prof. Dougan's lab. Each insert is being sequenced once from each end. The shotgun phase is now complete, and finishing has begun. At present there are 60 contigs over 1 kb in the database; a total of 5.106 Mb of sequence assembled from 87,331 reads.

Based on updated results posted Oct. 4, 1999, we have identified Contig 343, which contains the *S. typhi* ssb locus and critical flanking sequences within a 205,199 bp region. We have designed primers 1 and 4 (listed below) to amplify by PCR a 3535 bp fragment of the *S. typhi* chromosome in which the ssb locus is flanked by 1.5 kb of chromosomal sequence; this flanking symmetry is required for optimal crossover frequenceis to introduce the counter-selectable sacB—neo cassette and replace ssb. Using the methodology previously filed, we will use primers 1 and 2 to engineer a 5'-proximal 1.5 kb EcoRI-XmaI cassette, upstream of ssb. Primers 3 and 4 will be used to generate the 3'-distal 1.5 kb XmaI-EcoRI cassette, downstream of ssb; both 1.5 kb cassettes will be ligated together, forming the 3 kb EcoRI fragment containing a unique XmaI site exactly in the middle of the cassette. The sacB—neo cassette can now easily be inserted into the XmaI site, to complete construction of the mutagenesis cassette to be inserted into pCON (previously described in our first filing). The required complementing ssb-1 cassette will be constructed using primers 5 and 6 as a NheI cassette for replacement of drug resistance markers within the XbaI-SpeI cassettes of pGEN211, pGEN 222, pGEN 206, or any later version of the expression plasmids detailed herein.

```
PRIMER 1:                    (SEQ ID NO:6)
5'-gaattcGCGCGCTTCGCGATTCAGTCGCGTTCCTTCACAG

CTGGCGCAGGGGCGATTACTGATGAA-3'

PRIMER 2:                    (SEQ ID NO:7)
5'-cccggGAGTCTCCTGAATACGTTTCATAAATAGTGTAAAC

GCGTGAGTGTACCATTTCCACGTAGC-3'

PRIMER 3:                    (SEQ ID NO:8)
5'-cccggGTAAAAAACTCAAAGCGTTATTTGCATTTTCGCTA

TAGTTCTCGTCTGCTGAAATGCCTGGTGT-3'

PRIMER 4:                    (SEQ ID NO:9)
5'-gaattcCATTTCTATCAATAAATTACTATTAGTTTTGTCT

TCTAACCAAGCCTCTATTTTATGAGTATCCTCTTCAG-3'

PRIMER 5:                    (SEQ ID NO:10)
5'-gctagcATGGCCAGCAGAGGCGTAAACAAGGTGATTCTCG

TTGGTAATCTGGGCCAGGACCCGGAAGTACGC-3'

PRIMER 6:                    (SEQ ID NO:11)
5'-gctagcTCAGAACGGAATGTCGTCGTCAAAATCCATTGGC

GGTTCGTTAGACGGCGCTGGCGCG-3'
```

6.6 Stability of Expression Plasmids in the Absence of Selection

In order to develop a non-catalytic plasmid maintenance system to enhance the stability of multicopy expression plasmids encoding foreign antigens within CVD 908-htrA, experiments were initiated to monitor plasmid stability by quantitating expression of GFPuv by flow cytometry when strains were passaged in the absence of antibiotic selection. These experiments were designed to address 3 fundamental questions: 1] What is the effect of the induction level of $P_{ompC1}$ on the stability of plasmids encoding a heterologous antigen such as GFPuv? 2] What is the effect of copy number on the stability of plasmids expressing GFPuv? 3] How do the hok-sok, par, and parA maintenance functions affect plasmid retention, both as individual components and synergistically?

Initial flow cytometry experiments were carried out in which CVD 908htrA carried replicons with either the oriE1, ori15A, or ori101 origin of replication. It was quickly determined that replicons carrying the higher copy number oriE1 origins were very unstable, even when strains were grown in the presence of antibiotic selection. Flow cytometry results indicated that even when cultured in the presence of carbenicillin, the percentage of the bacterial populations no longer expressing detectable GFPuv ranged from approximately 50% for pGEN71 (carrying hok-sok) and pGEN84 (hok-sok+par) to 62% for pGEN211 (hok-sok+par+parA). Since replicons carrying an oriE1 origin clearly did not allow for optimal synthesis of the heterologous GFPuv test antigen within the majority of a growing population of live vector bacteria, this series of expression plasmids was not examined further.

CVD 908-htrA carrying expression plasmids with an ori15A origin were then examined. Strains were inoculated into 25 ml cultures of 1× LB+DHB (no antibiotic selection) containing either 50 mM, 150 mM, or 300 mM NaCl. Cultures were incubated for 24 hr at 37° C./250 rpm, diluted 1:1000 into fresh medium of identical osmolarity, and incubated for another 24 hr; samples from all cultures were analyzed for levels of GFPuv synthesis by flow cytometry. Results for the first passage in the absence of selection are listed in Table 6, and the histograms representing these data are shown in FIG. 8.

TABLE 6 shows stability within CVD 908-htrA of ori15A replicons, containing plasmid maintenance systems of increasing complexity, grown without selection and in the presence of increasing osmolarity.[1]

rescence intensity of 53.3. As the concentration of NaCl increases to 300 mM NaCl, the percentage of the population expressing GFPuv drops to 56.7%; nevertheless, the mean fluorescence intensity rises to 105.3. However, it is notable that for strains carrying pGEN222 with a complete plasmid maintenance system (i.e hok-sok+par+parA), the percentage of the population expressing the heterologous antigen remains at approximately 95%, while the mean fluorescence intensity increases from 52.1 (50 mM NaCl) to 89.2 (300 mM NaCl). It was noted that upon further passage of these strains for an additional 24 hrs in the absence of antibiotic selection, less than 5% of bacteria continued to express functional GFPuv. Streaks of these cultures onto solid medium, prior to flow analysis, indicated that non-fluorescing bacteria remained viable, but were sensitive to antibiotic selection. When non-fluorescing bacteria were

TABLE 6

| STRAIN[2] | 50 mM NaCl | | | 150 mM NaCl | | | 300 mM NaCl | | |
|---|---|---|---|---|---|---|---|---|---|
| | $O.D._{600}$ | Percent Fluorescing Bacteria | Mean Fluorescence Intensity | $O.D._{600}$ | Percent Fluorescing Bacteria | Mean Fluorescence Intensity | $O.D._{600}$ | Percent Fluorescing Bacteria | Mean Fluorescence Intensity |
| CVD 908-htrA | 0.98 | 100 | 0.6 | 1.11 | 100 | 0.6 | 1.12 | 100 | 0.6 |
| pGEN91 | 1.00 | 13.2 | 28.6 | 1.17 | 11.4 | 42.9 | 1.26 | 10.9 | 65.5 |
| pGEN111 | 1.26 | 47.4 | 51.8 | 1.17 | 28.9 | 93.6 | 1.12 | 42.4 | 65.1 |
| pGEN121 | 1.01 | 80.5 | 53.3 | 1.20 | 73.8 | 74.0 | 1.15 | 56.7 | 105.3 |
| pGEN193 | 1.11 | 71.4 | 50.9 | 1.24 | 65.2 | 64.7 | 1.22 | 53.7 | 90.8 |
| PGEN222 | 1.01 | 96.8 | 52.1 | 1.28 | 93.3 | 67.8 | 1.13 | 95.3 | 89.2 |

[1] These data are represented as histograms in FIG. 8.
[2] All strains were streaked from frozen master stocks onto 2X LB agar supplemented with DHB and 50 μg/ml of carbenicillin, and incubated for 36 hr at 30° C. Isolated colonies were pooled into 300 μl of 1X LB broth supplemented with DHB, from which 25 μl were inoculated into 25 ml of 1X LB broth containing DHB and either 50 mM, 150 mM, or 300 mM NaCl; cultures were incubated at 37° C., 250 rpm for 24 hr. For the results presented in this table, bacteria were then pelleted, resuspended in 1 ml PBS pH 7.4, and then diluted 1:1000 into PBS for analysis by flow cytometry.

[1] These data are represented as histograms in FIG. 8.
[2] All strains were streaked from frozen master stocks onto 2× LB agar supplemented with DHB and 50 μg/ml of carbenicillin, and incubated for 36 hr at 30° C. Isolated colonies were pooled into 300 μl of 1× LB broth supplemented with DHB, from which 25 μl were inoculated into 25 ml of 1× LB broth containing DHB and either 50 mM, 150 mM, or 300 mM NaCl; cultures were incubated at 37 ° C., 250 rpm for 24 hr. For the results presented in this table, bacteria were then pelleted, resuspended in 1 ml PBS pH 7.4, and then diluted 1:1000 into PBS for analysis by flow cytometry.

In general, as osmolarity increases and induction of $P_{ompC1}$ rises, the percentage of the live vector population expressing GFPuv drops; nevertheless, the mean level of fluorescence intensity increases as expected. For example, in the presence of 50 mM NaCl, 80.5% of a population of CVD908-htrA(pGEN121) express GFPuv with a mean fluosorted and plated, they were confirmed to be sensitive to antibiotic and non-fluorescent when irradiated with ultraviolet light, indicating loss of resident plasmids.

A passage experiment involving CVD 908-htrA carrying expression plasmids with an ori100 origin detected no significant loss of GFPuv expression after passage of strains for 48 hrs without selection, regardless of osmolarity. Therefore, strains were passaged in a separate experiment for 96 hrs (i.e. 4×24 hr) in the presence of either 50, 150, or 300 mM NaCl. Populations were analyzed by flow cytometry after 3 and 4 passages, and results are recorded in Table 7.

TABLE 7 shows stability within CVD 908-htrA of ori101 replicons, containing plasmid maintenance systems of increasing complexity, grown without selection and in the presence of increasing osmolarity.

TABLE 7

| STRAIN (Passage Number)[1] | 50 mM NaCl | | | 150 mM NaCl | | | 300 mM NaCl | | |
|---|---|---|---|---|---|---|---|---|---|
| | $O.D._{600}$ | Percent Fluorescing Bacteria | Mean Fluorescence Intensity | $O.D._{600}$ | Percent Fluorescing Bacteria | Mean Fluorescence Intensity | $O.D._{600}$ | Percent Fluorescing Bacteria | Mean Fluorescence Intensity |
| CVD 908-htrA (#3) | ND[2] | 100 | 0.6 | ND | 100 | 0.5 | ND | 100 | 0.5 |
| CVD 908-htrA (#4) | 1.00 | 100 | 0.3 | 1.18 | 100 | 0.3 | 1.19 | 100 | 0.3 |
| pGEN132 (#3) | ND | 45.5 | 29.0 | ND | 33.2 | 36.9 | ND | 81.3 | 47.3 |
| PGEN132 (#4) | 1.03 | 10.9 | 27.8 | 1.20 | 7.6 | 36.1 | 1.32 | 51.3 | 47.5 |
| pGEN142 (#3) | 1.05 | 99.5 | 35.5 | 1.23 | 98.9 | 45.1 | 1.28 | 96.5 | 47.8 |

TABLE 7-continued

| | 50 mM NaCl | | | 150 mM NaCl | | | 300 mM NaCl | | |
| --- | --- | --- | --- | --- | --- | --- | --- | --- | --- |
| STRAIN (Passage Number) [1] | $O.D._{600}$ | Percent Fluorescing Bacteria | Mean Fluorescence Intensity | $O.D._{600}$ | Percent Fluorescing Bacteria | Mean Fluorescence Intensity | $O.D._{600}$ | Percent Fluorescing Bacteria | Mean Fluorescence Intensity |
| pGEN142 (#4) | 1.17 | 94.4 | 38.0 | 1.29 | 91.5 | 45.0 | 1.33 | 93.9 | 47.7 |
| pGEN206 (#3) | 1.08 | 98.1 | 36.2 | 1.25 | 94.5 | 42.8 | 1.29 | 95.2 | 47.4 |
| pGEN206 (#4) | 1.13 | 80.2 | 32.6 | 1.26 | 68.6 | 36.6 | 1.33 | 93.5 | 41.3 |

[1] All strains were streaked from frozen master stocks onto 2X LB agar supplemented with DHB and 50 µg/ml of carbenicillin, and incubated for 36 hr at 30° C.. Isolated colonies were pooled into 300 µl of 1X LB broth supplemented with DHB, from which 24 µl were inoculated into 25 ml of 1X LB broth containing DHB and either 50 mM, 150 mM, or 300 mM NaCl; cultures were incubated at 37° C., 250 rpm for 24 hr (defined here as passage #1). For passage #2, 25 µl from passage #1 were inoculated into 25 ml (i.e. 1:1000 dilution) of identical medium and incubated at 37° C., 250 rpm for an additional 24 hr without selection. Passages 3 and 4 were carried out in identical fashion, but after the next passage had been set up the remaining bacteria were then pelleted, resuspended in 1 ml PBS pH 7.4, and then diluted 1:1000 into PBS for analysis by flow cytometry.
[2] ND = not done.

Live vectors carrying unstabilized ori101 replicons eventually lost the capacity to synthesize the heterologous antigen after 96 hr. For example, after 96 hr growth in the presence of 50 mM NaCl, only 10.9% of CVD 908-htrA (pGEN132) expressed GFPuv and fluoresced. As the concentration of NaCl in the medium was increased to 150 mM, fluorescence was detected in only 7.6% of the population; curiously, at 300 mM NaCl, the percentage recovered to 51.3% fluorescing bacteria. Remarkably, CVD 908-htrA carrying either pGEN142 (hok-sok) or pGEN206 (hok-sok+ parA) retained synthesis of GFPuv in greater than 95% of the population after 3 passages (72 hr), regardless of osmolarity (see Table 7). The percentage of fluorescing CVD 908htrA (pGEN142) remained near this level after 4 passages (96 hr), while decreasing slightly for CVD 908-htrA (pGEN206).

Taken together, these data show that as copy number is reduced, the apparent stability of resident plasmids and proficiency of a live vector to synthesize a heterologous antigen such as GFPuv increases; as plasmid maintenance systems accumulate within a given plasmid, apparent stability and antigen synthesis are further enhanced. In addition, as the induction of $P_{ompC1}$ and concomitant production of the heterologous antigen increases, the percentage of a growing population remaining capable of synthesizing antigen can be dramatically reduced.

6.7 Bacterial Strains and Culture Conditions

All plasmid constructions were recovered in *Escherichia coli* strain DH5α or DH5αF'IQ (Gibco BRL). Construction of the hok-sok gene cassette used pR1 template DNA isolated from *E. coli* strain J53(pR1), a generous gift from James B. Kaper. The live vector *S. typhi* CVD 908-htrA is an auxotrophic derivative of the wild type strain Ty2 with deletions in aroC, aroD, and htrA (Tacket et al. 1997b). All strains used for examination of plasmid stability were grown in media supplemented with 2,3-dihydroxybenzoic acid (DHB) as previously described (Hone et al. 1991; Galen et al. 1997). When grown on solid medium, plasmid-bearing strains of CVD 908-htrA were streaked from frozen (−70° C.) master stocks onto 2× Luria-Bertani agar containing (per liter) 20 g Bacto tryptone, 10 g Bacto yeast extract, and 3 g NaCl (2× LB agar) plus carbenicillin at a concentration of 50 µg/ml. Plates were incubated at 30° C. for 24–36 hr to obtain isolated colonies ~2 mm in diameter; strains were incubated at 30° C. to minimize the toxicity of GFPuv expression in CVD 908-htrA.

When grown in liquid medium, cultures were incubated at 37° C., 250 rpm for 16–24 hr. To examine the osmotic induction of the ompC promoter ($P_{ompC}$) within either *E. coli* DH5α or CVD 908-htrA, strains were grown in Bacto nutrient broth (Difco) containing DHB and either NaCl or sucrose; cultures were supplemented either with 50 µg/ml of carbenicillin or increasing concentrations of kanamycin where $P_{ompC}$-aphA-2 cassettes were examined. For quantitation of GFPuv synthesis using flow cytometry, 6–8 isolated colonies from master stocks streaked onto 2× LB agar as above were inoculated into 25 ml of 1× LB broth supplemented with 50 µg/ml carbenicillin where desired and NaCl at increasing concentrations to increase the induction of ompC promoters. Cultures were incubated at 37° C., 250 rpm for 16–24 hr prior to pelleting bacteria for flow cytometry as described below.

6.8 Molecular Genetic Techniques.

Standard techniques were used for the construction of the plasmids represented here (Sambrook et al., 1989). Unless otherwise noted, native Taq DNA polymerase (Gibco BRL) was used in polymerase chain reactions (PCR). *S. typhi* was prepared for electroporation of recombinant plasmids after harvesting from Miller's LB broth (Gibco BRL) supplemented with DHB; after pelleting bacteria, the cells were washed thrice with one culture volume of sterile distilled water and resuspended in sterile distilled water to a final volume of 1/100 of the original culture volume. Electroporation of strains was performed in a Gene Pulser apparatus (Bio-Rad) set at 2.5 kV, 200 Ω, and 25 µF. Following electroporation, bacteria were repaired using SOC medium and incubating at 37° C., 250 rpm for 45 min; bacteria were then plated on 1× LB medium containing DHB plus 50 µg/ml carbenicillin, and incubated at 30° C. for 24 hr. Isolated colonies were then swabbed onto supplemented 2× LB and incubated at 30° C. for 16 hr. Frozen master stocks were prepared by harvesting bacteria into SOC medium without further supplementation and freezing at −70° C.

6.9 Construction of Expression Vectors

The expression vectors listed in the following Table 8 were prepared in the course of the recent work.

TABLE 8

| Plasmid | Size (Kb) | Relevant genotype | Reference |
| --- | --- | --- | --- |
| pTETnir15 | 3.7 | oriE1 toxC bla | Oxer et al. (1991) |
| pJN1 | 1.9 | oriE1 bla | This work |
| pJN2 | 3.4 | oriE1 toxC bla | This work |

TABLE 8-continued

| Plasmid | Size (Kb) | Relevant genotype | Reference |
|---|---|---|---|
| pGFPuv | 3.3 | pUC19ori gfpuv bla | Clontech |
| pGFPompC | 3.5 | oriE1 gfpuv bla | This work |
| pNRB1 | 3.5 | oriE1 gfpuv tetA | This work |
| pGEN2 | 4.2 | oriE1 gfpuv tetA hok-sok | This work |
| pGEN3 | 4.1 | ori15A gfpuv tetA hok-sok | This work |
| pGEN4 | 5.6 | ori101 gfpuv tetA hok-sok | This work |
| pJN5 | 3.1 | oriE1 gfpuv bla | This work |
| pJN6 | 3.7 | oriE1 gfpuv bla hok-sok | This work |
| pJN7 | 4.1 | oriE1 gfpuv bla hok-sok par | This work |
| pJN8 | 5.4 | oriE1 gfpuv bla hok-sok parA | This work |
| pGEN51 | 3.6 | oriE1 gfpuv bla | This work |
| pGEN71 | 4.2 | oriE1 gfpuv bla hok-sok | This work |
| pGEN84 | 4.5 | oriE1 gfpuv bla hok-sok par | This work |
| pGEN183 | 5.9 | oriE1 gfpuv bla hok-sok parA | This work |
| pGEN211 | 6.2 | oriE1 gfpuv bla hok-sok par parA | This work |
| pGEN91 | 3.5 | ori15A gfpuv bla | This work |
| pGEN111 | 4.1 | ori15A gfpuv bla hok-sok | This work |
| pGEN121 | 4.5 | ori15A gfpuv bla hok-sok par | This work |
| pGEN193 | 5.8 | ori15A gfpuv bla hok-sok parA | This work |
| pGEN222 | 6.2 | ori15A gfpuv bla hok-sok par parA | This work |
| pGEN132 | 4.8 | ori101 gfpuv bla par | This work |
| pGEN142 | 5.4 | ori101 gfpuv bla par hok-sok | This work |
| pGEN206 | 7.1 | ori101 gfpuv bla par hok-sok parA | This work |

6.9.1 Construction of pJN1 and pJN2

The expression plasmids constructed for these studies are composed of 3 basic cassettes encoding 1] expression of a heterologous antigen, 2] a plasmid origin of replication, and 3] selection and maintenance functions. To accomplish this, a basic replicon was constructed in which these cassettes were separated by unique restriction sites. The primers used in construction of the plasmid cassettes are set forth in the following Table 9:

TABLE 9

| Primer number | Sequence[1] | Cassette created | GenBank Accession Number | Region of Homology[2] | Region of Complementarity[3] |
|---|---|---|---|---|---|
| 1 | 5'-GCAGGAAAGAACATGTGAG CCTAGGGCCAGCAAAAGGCCA GGAAC-3' (SEQ ID NO: 12) | oriE1 | J01749 | 2463–2507 | |
| 2 | 5'-CATGACCAAAATCCCTTA ACTAGTGTTTTAGATCTACT GAGCGTCAGACCCCG-3' (SEQ ID NO: 13) | " | " | | 3197–3145 |
| 3 | 5'-CGGGGTCTGACGCTCAGT AGATCTAAAACACTAGTTAA GGGATTTTGGTCATG-3' (SEQ ID NO: 14) | bla | " | 3145–3197 | |
| 4 | 5'-GCTGTCAAACATGAGAA TTCTAGAAGACGAAAGGGC CTCGTGATACGCC-3' (SEQ ID NO: 15) | " | " | | 17–1, 4361–4330 |
| 5 | 5'-ACAGCCTGCAGACAG ATCTTGACAGCTGGATCG CACTCTGGTATAATTGGG AAGCCCTGCAAAG-3' (SEQ ID NO: 16) | aphA-2 | V00618 | 1–64 | |
| 6 | 5'-CGAAGCCCAACCTTTCAT AGAAGCTAGCGGTGGATCC GAAATCTCGTGATGGCAGGT TG-3' (SEQ ID NO: 17) | " | " | | 1044–986 |
| 7 | 5'-AACAAGCGTTATAGGAA TTCTGTGGTAGCA-3' (SEQ ID NO: 18) | P$_{ampC}$ | K00541 | 4–33 | |
| 8 | 5'-ACTTTCATGTTATTAAAGA TCTGTTATATG-3' (SEQ ID NO: 19) | " | " | | 498–469 |
| 9 | 5'-AGATCTTAATCATCCACAG GAGGCTTTCTGATGAGTAAA GGAGAAGAACTTTTCAC TGG-3' (SEQ ID NO: 20) | gfpuv | U62636 | 289–317 | |
| 10 | 5'-GCTAGCTCATTATTTGT AGAGCTCATCCATGC-3' (SEQ ID NO: 21) | " | " | | 1008–983 |
| 11 | 5'-AGATCTGAATTCTAGAT CATGTTTGACAGCTTATCAT CGATAAGCTTTAATGCG-3' (SEQ ID NO: 22) | tetA | J01749 | 4–41 | |

TABLE 9-continued

| Primer number | Sequence[1] | Cassette created | GenBank Accession Number | Region of Homology[2] | Region of Complementarity[3] |
|---|---|---|---|---|---|
| 12 | 5'-AGATCTTATCAGGTCGAG GTGGCCCGGCTCCATGCACC GCGACGCAACGCG-3' (SEQ ID NO: 23) | " | " | | 1275–1234 |
| 13 | 5'-CGCGAATTCTCGAGACAA ACTCCGGGAGGCAGCGTGAT GCGGCAACAATCACACGGAT TTC-3' (SEQ ID NO: 24) | hok-sok-tetA | X05813 | 2–48 | |
| 14 | 5'-ATGAGCGCATTGTTAGA TTTCATTTTTTTTCCTCCTT ATTTTCTAGACAACATCAGC AAGGAGAAAGG-3' (SEQ ID NO: 25) | " | J01749, X05813 | | 108–86, 580–559 |
| 15 | 5'-CCTTTCTCCTTGCTGAT GTTGTCTAGAAAATAAGG AGGAAAAAAAAATGAAAT CTAACAATGCGCTCAT-3' (SEQ ID NO: 26) | " | X05813, J01749 | 559–580, 86–108 | |
| 16 | 5'-GCTACATTTGAAGAGAT AAATTGCACTGGATCCTAG AAATATTTTATCTGATTAA TAAGATGATC-3' (SEQ ID NO: 27) | ori15A | X06403 | | 1461–1397 |
| 17 | 5'-CGGAGATTTCCTGGAA GATGCCTAGGAGATACTT AACAGGGAAGTGAGAG-3' (SEQ ID NO: 28) | " | " | 780–829 | |
| 18 | 5'-GTCTGCCGGATTGCTTA TCCTGGCGGATCCGGTTGA CAGTAAGACGGGTAAGCCT GTTGAT-3' (SEQ ID NO: 29) | ori101 | X01654 | 4490–4550 | |
| 19 | 5'-CCTAGGTTTCACCTGTT CTATTAGGTGTTACATGCTG TTCATCTGTTACATTGTCGAT CTG-3' (SEQ ID NO: 30) | " | " | | 6464–6408 |
| 20 | 5'-AGGCTTAAGTAGCACCC TCGCAAGATCTGGCAAATC GCTGAATATTCCTTTTGTC TCCGAC-3' (SEQ ID NO: 31) | par | X01654 | | 4918–4858 |
| 21 | 5'-GAGGGCGCCCCAGCTGG CAATTCTAGACTCGAGCAC TTTTGTTACCCGCCAAACA AAACCCAAAAACAAC-3' (SEQ ID NO: 32) | aphA2-parA | V00618, X04268 | 38–16, 1–37 | |
| 22 | 5'-AGAAGAAAAATCGAATTC CAGCATGAAGAGTTTCAGAA AATGACAGAGCGTGAGCAA GTGC-3' (SEQ ID NO: 33) | " | X04268 | | 1704–1644 |
| 23 | 5'-CGAAGCCCAACCTTTCA TAGAAACTAGTGGTGGAA TCGAAATCTCGTGATGGCA GGTTG-3' (SEQ ID NO: 34) | " | V00618 | | 1044–986 |
| 24 | 5'-GTTGTTTTTGGGTTTTGTT TGGCGGGTAACAAAAGTGC TCGAGTCTAGAATTGCCAGC TGGGGCGCCCTC-3' (SEQ ID NO: 35) | " | X04268, V00618 | 37–1, 16–38 | | pTETnir15 (see Table 8; Oxer et al. 1991) was re-engineered such that the oriE1 origin of replication and bla gene were separated by a unique SpeI site. Toward this end, an oriE1 cassette was synthesized by PCR using Vent polymerase with primers 1 and 2 and pCVD315 (Galen et al. 1990) as the template. The resulting 735 bp fragment carries engineered SpeI and BglII sites 5'-proximal to the promoter controlling transcription of RNA II, and an engineered AvrII site 675 bases from these sites. A separate PCR reaction was carried out using primers 3 and 4 to create a 1234 bp bla cassette containing an engineered XbaI site 5'-proximal to the original EcoRI site. The products from these two PCR reactions were gel purified and used in an overlapping PCR with primers 1 and 4 to yield a final 1916 bp oriE1-bla fragment which was self-ligated to create pJN1. The $P_{nir15}$-toxC fragment from pTETnir15 was excised as an EcoRI (partial digestion)-AvaI fragment, in which the AvaI terminus was polished, and inserted into the multiple cloning region from pSL1180 (Brosius, 1989) cleaved with EcoRI and StuI; this cassette was then re-excised as an EcoRI (partial digestion)-AvrII fragment and inserted into pJN1 cleaved with EcoRI-AvrII, creating pJN2 (see Table 8).

6.9.2 Construction of pGFPompC

To facilitate screening of a functional osmotically regulated $P_{ompC1}$ allele from *Escherichia coli*, an aphA-2 cassette was constructed, encoding resistance to the aminoglycosides neomycin and kanamycin (Shaw et al. 1993). A polymerase chain reaction (PCR) was carried out using primers 5 and 6 with the template pIB279 (Blomfield et al. 1991) to generate a 1044 bp product, from which a promoterless 903 bp aphA-2 BglII-NheI fragment was cleaved for replacement of a BglII-NheI toxC cassette encoding fragment C of tetanus toxin in pTETnir15. The anaerobically regulated $P_{nir15}$ promoter was replaced with a 459 bp EcoRI-BglII $P_{ompC}$ allele constructed using primers 7 and 8 with chromosomal template DNA from *E. coli* DH5α to create pKompC. After confirming osmotic induction of $P_{ompC}$ by examining the increase in resistance to kanamycin with increasing osmolarity, the aphA-2 cassette was then replaced with a gfpuv gene encoding a prokaryotic codon-optimized GFPuv allele (Clontech; Crameri et al. 1996). The gfpuv gene was recovered by PCR using primers 9 and 10 with the template pGFPuv to generate a 751 bp BglII-NheI fragment which was inserted into pKompC, to generate pGFPompC. Colonies were screened for functional GFPuv, and the brightest colonies were then examined for induction of fluorescence with increasing concentrations of NaCl. A $P_{ompC1}$-gfpuv cassette was cleaved from pGFPompC1 as an EcoRI-NheI fragment and inserted into a derivative of pJN2 cleaved with EcoRI-NheI to create pJJ4.

6.9.3 Construction of pNRB1, pGEN2, pGEN3, and pGEN4

Since it was intended that copy number not be influenced by transcription originating from promoters outside the origin of replication, it was necessary to ensure that all replication cassettes were flanked at both ends by transcription terminators. Because the origin and antigen cassettes of pJN2 are separated by the trpA terminator, it was only necessary to insert one additional terminator between the origin and bla cassettes.

To facilitate construction of additional plasmids later on, a tetA-TlT2 cassette was created. pYA292 (Galan et al. 1990) was first cleaved with HindIII and BglII, and the T1T2 terminator fragment was polished and inserted into the SmaI site of the pBluescript II KS (Stratagene) mutiple cloning region; when the proper orientation was identified, this cassette was re-excised as a BamHI-PstI fragment and inserted into pIB307 (Blomfield et al. 1991) cleaved with BamHI-PstI, creating pJG14. It was later determined by sequence analysis that the cassette had undergone a deletion of approximately 100 bp, removing half of the T2 terminator.

Using pBR322 as a template, primers 11 and 12 were used to synthesize a 1291 bp tetA BglII fragment. This tetA BglII fragment was then inserted into the BamHI site of pJG14 such that transcription of the tetA gene is terminated at the T1T2 terminator, creating pJG14tetA. Finally, this tetA-T1T2 cassette was cleaved from pJG14tetA as an EcoRI-PstI fragment in which the PstI site had been removed by polishing; the resulting fragment was inserted into pJJ4, cleaved with SpeI, polished, and recleaved with EcoRI to replace the bla cassette and create pNRB1.

The non-catalytic post-segregational killing function to be incorporated into the plasmid maintenance systems of the expression plasmids described here was the hok-sok locus, from the multiple drug resistance R-factor pR1. Initial attempts at recovering the hok-sok locus after PCR were unsuccessful. It was therefore necessary to use overlapping PCR to generate a cassette in which hok-sok was transcriptionally fused to a promoterless tetA gene such that transcription originating from the hok promoter would continue into tetA and result in a transcript encoding both Hok and resistance to tetracycline. pR1 plasmid DNA was purified from *E. coli* J53(pR1) in which pR1 encodes resistance to both carbenicillin and chloramphenicol. A 640 bp hok-sok fragment was synthesized using primers 13 and 14; a promoterless 1245 bp tetA fragment was recovered in a separate PCR using primers 15 and 12 with pNRB1 as the template. The products from these two PCR reactions were then used in an overlapping PCR with primers 12 and 13 to yield the final 1816 bp hok-sok-tetA fragment. This fragment was inserted as an EcoRI-SphI fragment into pNRB1 cleaved with EcoRI-SphI, regenerating the tetA gene and creating pGEN1.

A set of 3 isogenic plasmids was then constructed, differing only in copy number, from which all further expression plasmids would be derived. The BglII-AvrII origin of replication cassette of pGEN1 was replaced by a BglII-AvrII oriE1 cassette from pJN2 to generate pGEN2. An ori15A replication cassette was synthesized by PCR using primers 16 and 17 with pACYC184 template to generate a 629 bp BamHI-AvrII fragment, which was inserted into pGEN2 cleaved with BglII-AvrII to create pGEN3. Finally, an ori101 replication cassette was synthesized by PCR using primers 18 and 19 with pSC101 template, generating a 1949 bp BamHI-AvrII fragment which was inserted into pGEN2 cleaved with BglII-AvrII to create pGEN4.

6.9.4 Construction of pJN5, pGEN51, pGEN91, and pGEN132

The principle set of isogenic expression plasmids, to which individual elements of a plasmid maintenance system were sequentially added, was composed of pGEN51 (containing oriE1), pGEN91 (containing ori15A), and pGEN132 (containing ori101). The basic replicon from which these 3 plasmids were constructed was pJN5, which was assembled by cleaving the $P_{ompC}$-gfpuv cartridge as an EcoRI-NheI fragment from pGFPompC to replace the $P_{nir15}$-toxC cassette of pJN2. Construction of pGEN51 was then accomplished by removal of the replication cassette from pGEN2 as a BamHI fragment, and replacement of the origin of replication within pJN5 digested with BglII and BamHI, thereby regenerating the gfpuv gene. Construction of pGEN91 and pGEN132 were constructed in an identical manner by excision of origin cassettes as BamHI fragments from pGEN3 and pGEN4 respectively (see FIG. 7 for representation of isogenic expression plasmids based on pGEN91).

6.9.5 Construction of pJN6, pGEN71, pGEN111, and pGEN142

The hok-sok locus was then inserted as an XbaI-Sa/I fragment into pJN5 cleaved with XbaI and Sa/I, again regenerating the gfpuv gene to create pJN6 (see Table 2). Construction of pGEN71, pGEN111, and pGEN142 was then carried out exactly as for pGEN51, pGEN91, and pGEN1132 by insertion into pJN6 of origin cassettes as BamHI fragments from pGEN 2, pGEN3, and pGEN4 respectively.

6.9.6 Construction of pJN7, pGEN84, and pGEN121

Construction of oriE1 and oriE15A expression plasmids containing a plasmid maintenance system, composed of both a post-segregational killing system and at least one partition function, was first attempted using the par function from pSC101. A 377 bp BamHI-BglII fragment was synthesized using primers 18 and 20 with pSC101 template DNA; this fragment was inserted into pJN6 cleaved with BglII to create pJN7. As in the constructions above, origin cassettes from pGEN2 and pGEN3 were then excised as BamHI fragments and inserted into pJN7 digested with BglII and BamHI to create pGEN84 and pGEN121.

6.9.7 Construction of pJN8, pGEN183, pGEN193, pGEN206, pGEN211 and pGEN222

The final expression plasmids were constructed by introduction of the parA active partitioning locus from pR1. As with hok-sok, initial attempts at recovering the parA locus after PCR were unsuccessful. It was necessary to use overlapping PCR to generate an aph-parA cassette, in which aph and parA were divergently transcribed and separated by XbaI and XhoI sites, to enable subcloning of the parA locus. A 1737 bp parA fragment was synthesized using primers 21 and 22 with pR1 template; a 1076 bp aphA-2 fragment was recovered in a separate PCR using primers 23 and 24 with pIB279 as the template. The products from these two PCR reactions were then used in an overlapping PCR with primers 22 and 23 to yield the final 2743 bp aphA2-parA fragment. This fragment was inserted as a 2703 EcoRI-SpeI fragment into pJN6. The parA cassette was then re-excised as an XhoI fragment and inserted again into pJN6 cleaved with XhoI, regenerating the gfpuv gene, and creating pJN8.

Plasmids carrying a plasmid maintenance system composed of the post-segregational killing hok-sok function and parA, were constructed by excision of oriE1 and ori15A BamHI-SpeI cassettes from pGEN51 and pGEN91 respectively, and insertion into pJN8 cleaved with BamHI and SpeI to create pGEN183 and pGEN193 respectively. Plasmids containing the full complement of hok-sok, par, and parA maintenance functions were constructed by insertion of par-containing origin cassettes as BamHI-SpeI cassettes from pGEN84, pGEN121, and pGEN132 into pJN8 cleaved with BamHI and SpeI to create pGEN211, pGEN222, and pGEN206 respectively.

6.10 Quantitation of GFPuv and Plasmid Maintenance

Quantitation of GFPuv and plasmid maintenance were analyzed by measuring the fluorescence of plasmid-bearing live vectors using an Epics Elite ESP flow cytometer/cell sorter system (Coulter) with the argon laser exciting bacteria at 488 nm and emissions detected at 525 nm. 25 ml 1× LB cultures grown as described above were pelleted, and bacteria were resuspended into 1 ml of PBS. Cells were then diluted 1:1000 into PBS prior to determination of viable counts and flow analysis. Forward versus side light scatter, measured with logarithmic amplifiers, was used to gate on bacteria. A minimum of 50,000 events were acquired from each sample at a collection rate of approximately 3500 events per second. Mean fluorescence intensity for a given bacterial population was determined using the Epics Elite Software Analysis Package. The levels of autofluorescence, determined using plasmidless S. typhi CVD 908-htrA and E. coli DH5α strains, were used to place markers quantitating the percentages of bacteria in a given population expressing GFPuv.

6.11 Conclusions

The broad objective of the research presented in Sections 6.6–6.10 was to investigate the feasibility of developing a plasmid maintenance system for the stabilization of multicopy expression plasmids encoding foreign antigens in an S. typhi live vector vaccine strain, without additional modification of the chromosome. The maintenance of expression plasmids was enhanced at two independent levels. First, dependence upon balanced-lethal maintenance systems that involve catalytic enzymes expressed from multicopy plasmids was removed; this was accomplished through incorporation into expression plasmids of a post-segregational killing system based on the non-catalytic hok-sok plasmid addiction system from the antibiotic-resistance factor pR1. At least one naturally occurring plasmid partition function was also introduced into these expression plasmids, to potentially eliminate random segregation of such plasmids, thereby enhancing their inheritance and stability.

Although these expression plasmids are ultimately intended to express immunogenic and protective antigens for delivery to the human immune system, GFPuv was selected as a test reporter antigen because quantitation of mean fluorescence in a population of growing live vectors could be used as a measure of the stability of resident plasmids within the live vector. All expression plasmids carried an identical antigen expression cassette, with a $P_{ompC1}$ allele controlling transcription, and translation optimized by incorporation of a consensus ribosome binding site. Because no catalytic activity is associated with the fluorescence of GFPuv, the level of fluorescence intensity measured by flow cytometry within individual bacteria could be correlated directly with gene dosage and copy number. In addition, use of an osmotically regulated ompC promoter allowed an assessment of plasmid stability and live vector viability as increasing osmolarity induced higher levels of GFPuv synthesis and presumably higher levels of metabolic stress on the live vector. As seen in Table 2, we confirmed that the $P_{ompC1}$ allele engineered for these studies was responsive to increased osmolarity; when driving expression of an aph-2 resistance gene, resistance to less than 50 μg/ml kanamycin was observed in the absence of osmotic pressure but resistance increased to greater than 800 μg/ml in the presence of 300 mM NaCl. It was surprising that although the $P_{ompC1}$ allele was engineered from the chromosomal locus of E. coli, it appeared to function more efficiently in S. typhi. The uninduced level of expression of GFPuv was the same for both DH5α and CVD 908-htrA (mean fluorescence intensity of 4.45 vs 5.37 respectively, Table 3). However, GFPuv synthesis increased 70% in DH5α after induction, but rose over 300% in CVD 908-htrA (mean fluorescence intensity of 7.69 vs 23.4 respectively). This effect was not limited to the $P_{ompC1}$ allele but was equally remarkable when using $P_{ompC3}$ (Table 3). These data do not agree with recent observations of Martinez-Flores et al (1999) who reported that E. coli $P_{ompC1}$-lacZ genetic fusions expressed constitutively within S. typhi, and that this constitutive level of expression was comparable to induced levels within E. coli. Although we have identified a defined locus of point mutations at the 3'-terminus of our E. coli $P_{ompC1}$ allele which could explain its osmotically controlled behavior within S. typhi CVD 908-htrA, such mutations were not identified within $P_{ompC3}$, which also responds to osmolarity within CVD 908-htrA. It should be noted, however, that the genetic fusions studied by Martinez-Flores et al involved 1,150 bp of the E. coli 5' ompC upstream control region, while the $P_{ompC}$ alleles constructed here involve only 459 bp of the 5'-proximal control region of ompC. Regardless of this discrepancy, it is encouraging that the highest levels of regulated heterologous gene expression are observed within the attenuated S. typhi live vector vaccine strain.

The contributions of several plasmid maintenance systems to the stability of plasmids within CVD 908-htrA, growing in the absence of antibiotic selection, were then examined. No combination of maintenance functions could stabilize plasmids containing oriE1 origins of replication; in fact, these constructs were difficult to propagate even in the presence of antibiotic. These observations cast doubt upon the rationale for using higher copy number plasmids to optimize expression of heterologous antigens within the cytoplasm of *S. typhi*-based live vectors, a strategy that, heretofore, has been followed by other groups investigating *Salmonella* as live vectors (Covone et al. 1998).

Incorporation of plasmid maintenance systems into plasmids carrying an ori15A origin of replication was more encouraging. When live vectors carrying such plasmids were passage without selection for 24 hr at 37° C., the effects of various combinations of maintenance functions became apparent. In the absence of maintenance functions, the ori15A replicon pGEN91 was lost from greater than 90% of the population, regardless of the level of induction of $P_{ompC1}$ (see Table 6 and FIG. 8). With incorporation of the hok-sok post-segregational killing locus in pGEN111, the percentage of bacteria expressing GFPuv tripled under all induction conditions, confirming the observations of others that the hok-sok locus enhances the stability of ori15A replicons (Gerdes et al. 1985; Gerdes, 1988; Gerdes et al. 1997b). However, it was still noted that regardless of induction conditions, greater than 50% of the bacterial population no longer fluoresced. Since it was confirmed that at least a portion of this non-fluorescing population was still viable and lacked drug resistance, these data confirm previous reports (Gerdes et al. 1986; Wu and Wood, 1994; Pecota et al. 1997) that the presence of a hok-sok post-segregational killing system is insufficient by itself to ensure that plasmidless viable bacteria will not arise in a growing population.

One possible mechanism that allows for escape from the influence of hok-sok involves spontaneous point mutations arising within the lethal Hok open reading frame, which could conformationally inactivate Hok and thereby allow plasmid loss to occur without lethality. This point emphasizes the requirement of multiple mechanisms for enhancing the stability of resident plasmids within growing bacteria; should one maintenance function become inactivated, the probability of other independent functions simultaneously becoming inactivated becomes vanishingly small. Indeed, such redundancy in maintenance functions is widespread within naturally occurring low copy number plasmids (Nordstrom and Austin, 1989). For example, the *Escherichia coli* sex factor F contains one active partitioning function (sop) and two killing systems (ccd and flm) (Loh et al. 1988; Golub and Panzer, 1988; Van Melderen et al. 1994; Niki and Hiraga, 1997). Similarly, the drug resistance plasmid pR1 contains the active partitioning function parA, as well as the post-segregational killing system hok-sok, in addition, it carries yet another recently defined kis-kid killing system (Bravo et a]. 1987; Bravo et al. 1988; Ruiz-Echevarria et al. 1995). We demonstrate in work reported here that insertion into multicopy ori15A replicons of a more complete maintenance system, composed of both a post-segregational system and two partition functions, dramatically improves the stability of these expression plasmids in the absence of selection, regardless of induction conditions for heterologous antigen expression. However, after passage without selection for 48 hrs, plasmids were eventually lost from the bacterial population, due to escape from the lethality of Hok. This problem has recently been addressed by Pecota et al (1997) who reported that incorporation of dual killing systems significantly improved plasmid stability when compared to the use of hok-sok alone; no partition functions were present in these plasmids. Perhaps inclusion of the kis-kid killing system, to more fully represent the complement of pR1 stability functions, may be required for optimal stability of higher copy expression plasmids within *S. typhi* live vectors; since phd-doc PSK cassettes have recently been constructed, we are also examining the compatibility of this PSK function in our expression plasmids pGEN211, pGEN222 and pGEN206.

A comparison of strains carrying pGEN121 (an ori15A replicon carrying hok-sok+par, ~15 copies per chromosomal equivalent) with the much lower copy number plasmid pGEN142 (an ori101 replicon carrying hok-sok+par; ~5 copies per chromosomal equivalent) shows that under conditions of maximum induction of $P_{ompC1}$ with 300 mM NaCl, 57% of a population of CVD 908-htrA(pGEN121), passaged for only 24 hr without selection, fluoresce with a mean fluorescence intensity of 105.3; for a population of CVD 908-htrA(pGEN142), passaged for 96 hr without selection under identical induction conditions, 94% of the bacteria analyzed by flow cytometry still maintain a mean fluorescence intensity of 47.7. Based on such results with GFPuv as a test antigen, it is tempting to speculate that an optimum level of heterologous antigen presented by an attenuated *S. typhi*-based live vector vaccine to the human immune system can be achieved by decreasing the copy number of resident expression plasmids to perhaps 5 copies per chromosomal equivalent.

The efficiency of eliciting an immune response directed against a heterologous antigen will depend in part upon the ability of the live vector to present such antigens to the immune system. The ability of a live vector to present antigens will in turn depend upon the stability of multicopy expression plasmids that encode the heterologous antigens. Our results demonstrate that inclusion of a plasmid maintenance system within multicopy expression plasmids, without further genetic manipulation of the live vector, enhances the stability of such expression plasmids. However, the presence of multicopy plasmids may also influence the metabolic fitness of the live vector. This is relevant because some foreign antigens of interest exert a deleterious effect on the live vector.

While we do not intend to be bound to this theory, we conclude that a significant metabolic burden is placed upon CVD 908-htrA carrying a multicopy expression plasmid; as copy number and/or level of gene expression increases, metabolic burden increases. Studies with *E. coli* have clearly established that plasmid-bearing bacteria grow slower than plasmidless bacteria (Boe et al. 1987; McDermott et al. 1993; Wu and Wood, 1994; Pecota et al. 1997; Summers, 1998). It has also been demonstrated that as copy number increases, the growth rate of such strains decreases; similarly, as induction of heterologous genes increases, growth rate decreases further (Wu and Wood, 1994; Pecota et al. 1997). Clearly, spontaneous plasmid loss would remove any metabolic burden and allow plasmidless bacteria to quickly outgrow the population of plasmid-bearing bacteria. In elegant studies, Wu and Wood (Wu and Wood, 1994) showed that plasmid-bearing *E. coli* strains maintained plasmids under conditions where cloned gene expression was low for 100 hr when passaged in the absence of selection; in contrast, under maximum induction conditions, complete plasmid loss occurred within 10 hr. Interestingly, when the hok-sok locus was inserted into these expression plasmids, the plasmids were maintained for 300 hr. under uninduced conditions and 30 hr. under inducing conditions. Such a shift in antigen expression within a population of live vector bacteria would be expected to reduce the efficiency of stimulating any immune response specific to the foreign antigen. Our analysis leads us to conclude that the goal for an effective multivalent *S. typhi*-based live vector vaccine is to optimize viability using stabilized lower copy number expression vectors, capable of expressing high levels of heterologous antigen in response to an environmental signal likely to be encountered in vivo after the vaccine organisms have reached an appropriate ecological niche. We are currently testing this strategy using the murine intranasal model to examine the immunogenicity of fragment C of tetanus toxin expressed within CVD 908-htrA from our expression vectors pGEN211 (oriE1), pGEN222 (ori15A), and pGEN206 (ori101), all of which carry identical plasmid maintenance systems and differ only in copy number. The work presented herein enables the development of single dose, oral *S. typhi*-based live vector vaccines capable of inducing protective immune responses against multiple unrelated human pathogens.

7. REFERENCES

The disclosures of the following references are incorporated herein in their entirety:

Acheson, D. W. K. 1998. Nomenclature of enterotoxins. Lancet 351:1003.

Acheson, D. W. K., M. M. Levine, J. B. Kaper, and G. T. Keusch. 1996. Protective immunity to Shiga-like toxin I following oral immunization with Shiga-like toxin I B-subunit-producing Vibrio cholerae CVD 103-HgR. *Infection and Immunity* 64:355.

Austin, S. J. 1988. Plasmid partition. *Plasmid* 20:1.

Austin, S., S. Friedman, and D. Ludtke. 1986. Partition functions of unit-copy plasmids can stabilize the maintenance of plasmid pBR322 at low copy number. *J Bacteriol* 166: 1010–1013.

Barry, E. M., O. G. Gomez-Duarte, S. Chatfield, R. Rappuoli, M. Pizza, G. Losonsky, J. E. Galen, and M. M. Levine. 1996. Expression and immunogenicity of pertussis toxin SI subunit-tetanus toxin fragment C fusions in *Salmonella typhi* vaccine strain CVD 908. *Infection and Immunity* 64:4172–4181

Barth, P. T., H. Richards, and N. Datta. 1978. Copy numbers of coexisting plasmids in *Escherichia coli* K-12. *J Bacteriol* 135: 760–765.

Bast, D. J., J. L. Brunton, M. A. Karmali, and S. E. Richardson. 1997. Toxicity and immunogenicity of a verotoxin 1 mutant with reduced globotriaosylceramide receptor binding in rabbits. *Infection and Immunity* 65:2019.

Baumler, A. J., J. G. Kusters, I. Stojiljkovic, and F. Heffron. 1994. *Salmonella typhimurium* loci involved in survival within macrophages. *Infection and Immunity* 62:1623.

Beaucage, S. L., C. A. Miller, and S. N. Cohen. 1991. Gyrase-dependent stabilization of pSC101 plasmid inheritance by transcriptionally active promoters. *EMBO J* 10: 2583–2588.

Blattner, F. R., G. Plunkett III, C. A. Bloch, N. T. Perna, V. Burland, M. Riley, J. Collado-Vides, J. D. Glasner, C. K. Rode, G. F. Mayhew, J. Gregor, N. W. Davis, H. A. Kirkpatrick, M. A. Goeden, D. J. Rose, B. Mau, and Y. Shao. 1997. The complete genome sequence of *Escherichia coli* K-12. *Science* 277:1453.

Blomfield, I. C., V. Vaughn, R. F. Rest, and B. J. Eisenstein. 1991. Allelic exchange in *Escherichia coli* using the *Bacillus subtilis sacB gene and a temperature-sensitive pSC*101 replicon. *Molecular Microbiology* 5:1447–1457.

Boe, L. and K. V. Rasmussen. 1996. Suggestions as to quantitative measurements of plasmid loss. *Plasmid* 36:153.

Boe, L., K. Gerdes, and S. Molin. 1987. Effects of genes exerting growth inhibition and plasmid stability on plasmid maintenance. *Journal of Bacterology* 169:4646–4650.

Bokman, S. H. and W. W. Ward. 1981. Renaturation of *Aequorea* green-fluorescent protein. *Biochemical and Biophysical Research Communications* 101:1372.

Bosworth, B. T., J. E. Samuel, H. W. Moon, A. D. O'Brien, V. M. Gordon, and S. C. Whipp. 1996. Vaccination with genetically modified Shiga-like toxin lie prevents edema disease in swine. *Infection and Immunity* 64:55.

Bouvier, J., C. Richaud, W. Higgins, O. Bogler, and P. Stragier. 1992. Cloning, characterization, and expression of the dapE gene of *Escherichia coli. Journal of Bacteriology* 174:5265.

Boyd, B. and C. A. Lingwood. 1989. Verotoxin receptor glycolipid in human renal tissue. *Nephron* 51:207.

Bravo, A., G. de Torrontegui, and R. Diaz. 1987. Identification of components of a new stability system of plasmid R1, ParD, that is close to the origin of replication of this plasmid. *Mol Gen Genet* 210: 101–110.

Bravo, A., S. Ortega, G. de Torrontegui, and R. Diaz. 1988. Killing of *Escherichia coli* cells modulated by components of the stability system pard of plasmid R1. *Mol Gen Genet* 215: 146–151.

Brosius, J. 1989. Superpolylinkers in cloning and expression vectors. *DNA* 8: 759–777.

Butterton, J. R., E. T. Ryan, D. W. Acheson, and S. B. Calderwood. 1997. Coexpression of the B subunit of Shiga toxin 1 and EaeA from enterohemorrhagic *Escherichia coli* in Vibrio cholerae vaccine strains. *Infection and Immunity* 65:2127–2135.

Cabello, F., K. Timmis, and S. N. Cohen. 1976. Replication control in a composite plasmid constructed by in vitro linkage of two distinct replicons. *Nature* 259: 285–290.

Calderwood, S. B., D. W. K. Acheson, G. T. Keusch, T. J. Barrett, P. M. Griffin, N. A. Strockbine, B. Swaminathan, J. B. Kaper, M. M. Levine, B. S. Kaplan, H. Karch, A. D. O'Brien, T. G. Obrig, Y. Takeda, P. I. Tarr, and I. K. Wachsmuth. 1996. Proposed new nomenclature for SLT (VT) family. *ASM News* 62:118.

Calderwood, S. B., F. Auclair, A. Donohue-Rolfe, G. T. Keusch, and J. J. Mekalanos. 1987. Nucleotide sequence of the Shiga-like toxin genes of *Escherichia coli. Proceedings of the National Academy of Sciences USA* 84:4364.

Carlini, L. E., R. D. Porter, U. Curth, and C. Urbanke. 1993. Viability and preliminary in vivo characterization of site-specific mutants of *Escherichia coli* single-stranded DNA-binding protein. *Molecular Microbiology* 10:1067.

Carter, P. B. and F. M. Collins. 1974. Growth of typhoid and paratyphoid bacilli in intravenously infected mice. *Infection and Immunity* 10:816.

Cerin, H. and J. Hackett. 1989. Molecular cloning and analysis of the incompatibility and partition functions of the virulence plasmid of *Salmonella typhimurum. Microbial Pathogenesis* 7:85.

Cerin, H. and J. Hackett. 1993. The parVP region of the *Salmonella typhimurium* virulence plasmid pSLT contains four loci required for incompatibility and partition. *Plasmid* 30:30.

Chalfie, M., Y. Tu, G. Euskirchen, W. W. Ward, and D. C. Prasher. 1994. Green fluorescent protein as a marker for gene expression. *Science* 263: 802.

Chambers, S. P., S. E. Prior, D. A. Barstow, and N. P. Minton. 1988. The pMTLnic cloning vectors. I. Improved pUC polylinker regions to facilitate the use of sonicated DNA for nucleotide sequencing. *Gene* 68–139.

Chang, A. C. Y., and S. N. Cohen. 1978. Construction and characterization of amplifiable multicopy DNA cloning vehicles derived from the P15A cryptic miniplasmid. *J Bacteriol* 134: 1141–1156.

Chase, J. W. and K. R. Williams. 1986. Single-stranded DNA binding proteins required for DNA replication. *Annual Reviews in Biochemistry* 55:103.

Chase, J. W., J. B. Murphy, R. F. Whittier, E. Lorensen, and J. J. Sninsky. 1983. Amplification of ssb-1 mutant single-stranded DNA-binding protein in *Escherichia coli*. *Journal of Molecular Biology* 163,164:193.

Chatfield, S., K. Strahan, D. Pickard, I. G. Charles, C. E. Hormaeche, and G. Dougan. 1992. Evaluation of *Salmonella typhimurium* strains harbouring defined mutations in htrA and aroA in the murine salmonellosis model. *Microbial Pathogenesis* 12:145.

Clark, C., D. Bast, A. M. Sharp, P. M. St. Hilaire, R. Agha, P. E. Stein, E. J. Toone, R. J. Read, and J. L. Brunton. 1996. Phenylalanine 30 lays an important role in receptor binding of verotoxin-1. *Molecular Microbiology* 19:891.

Conradi, H. 1903. Ueber losliche, durch aseptische autolyse erhaltene giftstoffe von ruhr-und Typhusbazillen. *Dtsch. Med. Wochenschr.* 29:26.

Covarrubias, L., L. Cervantes, A. Covarrubias, X. Soberon, 1. Vichido, A. Blanco, Y. M. Kupersztoch-Portnoy, and F. Bolivar. 1981. Construction and characterization of new cloning vehicles. V. Mobilization and coding properties of pBR322 and several deletion derivatives including pBR327 and pBR328. *Gene* 13: 2535.

Covone, M. G., M. Brocchi, E. Palla, W. D. da Silveira, R. Rappuoli, and C. L Galeotti. 1998. Levels of expression and immunogenicity of attenuated *Salmonella enterica* serovar typhimurium strains expressing *Escherichia coli* mutant heat-labile enterotoxin. *Infection and Immunity* 66:224–231.

Crameri, A., E. A. Whitehorn, E. Tate, and W. P. Stemmer. 1996. Improved green fluorescent protein by molecular evolution using DNA shuffling. *Nat Biotechnol* 14: 315–319.

Dam, M. and K. Gerdes. 1994. Partitioning of plasmid R1: ten direct repeats flanking the parA promoter constitute a centromere-like partition site parC, that expresses incompatibility. *Journal of Molecular Biology* 236:1289–1298.

Dopf, J. and T. M. Horiagon. 1996. Deletion mapping of the Aequorea victoria green fluorescent protein. *Gene* 173:39.

Downes, F. P., T. J. Barrett, J. H. Green, C. H. Aloisio, J. S. Spika, N. A. Strockbine, and I. K. Wachsmuth. 1988. Affinity purification and characterization of Shiga-like toxin 11 and production of toxin-specific monoclonal antibodies. *Infection and Immunity* 56:1926.

Egger, L. A., H. Park, and M. Inouye. 1997. Signal transduction via the histidyl-aspartyl phosphorelay. *Genes to Cells* 2:167.

Endo, Y., K. Tsurugi, T. Yutsudo, Y. Takeda, T. Ogasawara, and K. Igarashi. 1988. Site of action of a Vero toxin (VT2) from *Escherichia coli* O157:H7 and of Shiga toxin on eukaryotic ribosomes: RNA N-glycosidase activity of the toxins. *European Journal of Biochemistry* 171:45.

Forrest, B. D., J. T. Labrooy, S. R. Attridge, G. Boehm, L. Beyer, R. Morona, D. J. C. Shearman, and D. Rowley. 1989. Immunogenicity of a candidate live oral typhoid/cholera hybrid vaccine in humans. *J. Infect. Dis.* 159: 145.

Fraser, M. E., M. M. Chernaia, Y. V. Kozlov, and M. N. G. James. 1994. Crystal structure of the holotoxin from *Shigella dysenteriae* at 2.5 A resolution. *Nature Structural Biology* 1:59.

Galan, J. E., K. Nakayama, and R. Curtiss III. 1990. Cloning and characterization of the asd gene of *Salmonella typhimurium*: use in stable maintenance of recombinant plasmids in *Salmonella* vaccine strains. *Gene* 94:29–35.

Galen, J. E. and M. M. Levine. 1995. Improved suicide vectors for chromosomal mutagenesis in *Salmonella typhi*. Abstracts of the Annual Meeting of the American Society of Microbiology H192:(Abstract)

Galen, J. E. and M. M. Levine. 1996. Further refinements of suicide vector-mediated chromosomal mutagenesis in *Salmonella typhi*. Abstracts of the Annual Meeting of the American Society of Microbiology H260:(Abstract)

Galen, J. E., O. G. Gomez-Duarte, G. Losonsky, J. L. Halpern, C. S. Lauderbaugh, S. Kaintuck, M. K. Reymann, and M. M. Levine. 1997. A murine model of intranasal immunization to assess the immunogenicity of attenuated *Salmonella typhi* live vector vaccines in stimulating serum antibody responses to expressed foreign antigens. *Vaccine* 15:700–708.

Galen, J. E., E. R. Vimr, L. Lawrisuk, and J. B. Kaper. 1990. Cloning, sequencing, and expression of the gene, nanH, for *Vibrio cholerae* neuraminidase. In *Advances in research on cholera and related diarrheas* (Edited by Sack R. B. and Zinnake Y. Tokyo: KTK Scientific Publishers. pp. 143–153.

Gay, P., D. Le Coq, M. Steinmetz, E. Ferrari, and J. A. Hoch. 1983. Cloning structural gene sacB, which codes for exoenzyme levansucrase of *Bacillus subtilis*: expression of the gene in *Escherichia coli*. *Journal of Bacteriology* 153:1424.

Gerdes, K. 1988. The parB (hok-sok) locus of plasmid R1: a general purpose plasmid stabilization system. *Bio/Technology* 6: 1402–1405.

Gerdes, K. and S. Molin. 1986. Partitioning of plasmid R1: structural and functional analysis of the parA locus. *Journal of Molecular Biology* 190:269.

Gerdes, K., A. P. Gultyaev, T. Franch, K. Pedersen, and N. D. Mikkelsen. 1997. Antisense RNA-regulated programmed cell death. *Annual Reviews in Genetics* 31:1–31.

Gerdes, K., J. S. Jacobsen, and T. Franch. 1997b. Plasmid stabilization by post-segregational killing. *Genet Eng* (*NY*) 19: 49–61.

Gerdes, K., J. E. Larsen, and S. Molin. 1985. Stable inheritance of plasmid R1 requires two different loci. *J Bacteriol* 161: 292–298.

Gerdes, K., P. B. Rasmussen, and S. Molin. 1986. Unique type of plasmid maintenance function: postsegregational killing of plasmid-free cells. *Proc Natl Acad Sci USA* 83: 3116–3120.

Gerichter, C. B. 1960. The dissemination of *Salmonella typhi*, *S. paratyphi A*, and *S. paratyphi B* through the organs of the white mouse by oral infection. *Journal of Hygiene, Cambridge* 58:307.

Gerichter, C. B. and D. L. Boros. 1962. Dynamics of infection of the blood stream and internal organs of white mice with *Salmonella typhi* by intraperitoneal injection. *Journal of Hygiene, Cambridge* 60:311.

Golub, E. I., and H. A. Panzer. 1988. The F factor of *Escherichia coli* carries a locus of stable plasmid inheritance stm, similar to the parB locus of plasmid R1. *Mol Gen Genet* 214: 353–357.

Gomez-Duarte, O. G., J. E. Galen, S. N. Chatfield, R. Rappuoli, L. Eidels, and M. M. Levine. 1995. Expression of fragment C of tetanus toxin fused to a carboxyl-terminal fragment of diphtheria toxin in *Salmonella typhi* CVD 908 vaccine strain. *Vaccine* 13:1596.

Gonzalez, C., D. M. Hone, F. Noriega, C. O. Tacket, J. R. Davis, G. Losonsky, J. P. Nataro, S. Hoffman, A. Malik, E. Nardin, M. Sztein, D. G. Heppner, T. R. Fouts, A. Isibasi, and M. M. Levine. 1994. *Salmonella typhi* vaccine strain CVD 908 expressing the circumsporozoite protein of *Plasmodium falciparum*: strain construction and safety and immunogenicity in humans. *Journal of Infectious Diseases* 169: 927–931.

Gordon, V. M., S. C. Whipp, H. W. Moon, A. D. O'Brien, and J. E. Samuel. 1992. An enzymatic mutant of Shiga-like toxin II variant is a vaccine candidate for edema disease of swine. *Infection and Immunity* 60:485.

Gottesman, S., W. P. Clark, V. de Crecy-Lagard, and M. R. Maurizi. 1993. ClpX, an alternative subunit for the ATP-dependent Clp protease of *Escherichia coli*. *Journal of Biological Chemistry* 268:22618.

Green, J. M., B. P. Nichols, and R. G. Matthews. 1996. Folate biosynthesis, reduction, and polyglutamylation. In *Escherichia coli* and *Salmonella: Cellular and molecular biology*. 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 665.

Griffin, P. M. 1995. *Escherichia coli* O157:H7 and other enterohemorrhagic *Escherichia coli*. In *Infections of the gastrointestinal tract*. M. J. Blaser, P. D. Smith, J. I. Ravdin, H. B. Greenberg and R. L. Guerrant, eds. Raven Press, Ltd, New York, p. 739.

Gyles, C. L. 1992. *Escherichia coli* cytotoxins and enterotoxins. *Canadian Journal of Microbiology* 38:734.

Heim, R., D. C. Prasher, and R. Y. Tsien. 1994. Wavelength mutations and posttranscriptional autoxidation of green fluorescent protein. *Proceedings of the National Academy of Sciences USA* 91:12501.

Hiszczynska-Sawicka, E., and J. Kur. 1997. Effect of *Escherichia coli* IHF mutations on plasmid p15A copy number. *Plasmid* 38: 174–179.

Hoiseth, S. K. and B. A. Stocker. 1981. Aromatic-dependent *Salmonella typhimurium* are non-virulent and effective as live vaccines. *Nature* 291:238.

Hone, D. M., A. M. Harris, S. Chatfield, G. Dougan, and M. M. Levine. 1991. Construction of genetically defined double aro mutants of *Salmonella typhi*. *Vaccine* 9: 810–816.

Hovde, C. J., S. B. Calderwood, J. J. Mekalanos, and R. J. Collier. 1988. Evidence that glutamic acid 167 is an active-site residue of Shiga-like toxin I. *Proceedings of the National Academy of Sciences USA* 85: 2568.

Jackson, M. P., E. A. Wadolkowski, D. L. Weinstein, R. K. Holmes, and A. D. O'Brien. 1990. Functional analysis of the Shiga toxin and Shiga-like toxin type II variant binding subunits by using site-directed mutagenesis. *Journal of Bacteriology* 172:653.

Jackson, M. P., R. J. Neill, A. D. O'Brien, R. K. Holmes, and J. W. Newland. 1987. Nucleotide sequence analysis and comparison of the structural genes for Shiga-like toxin I and Shiga-like toxin II encoded by bacteriophages from *Escherichia coli*. *FEMS Microbiology Letters* 44:109.

Jackson, M. P., R. L. Deresiewicz, and S. B. Calderwood. 1990. Mutational analysis of the Shiga toxin and Shiga-like toxin II enzymatic subunits. *Journal of Bacteriology* 172:3346.

Jarvis, K. G. and J. B. Kaper. 1996. Secretion of extracellular proteins by enterohemorrhagic *Escherichia coli* via a putative type III secretion system. *Infection and Immunity* 64:4826.

Jarvis, K. G., J. A. Giron, A. E. Jerse, T. K. McDaniel, M. S. Donnenberg, and J. B. Kaper. 1995. Enteropathogenic *Escherichia coli* contains a putative type III secretion system necessary for the export of proteins involved in attaching and effacing lesion formation. *Proceedings of the National Academy of Sciences USA* 92:7996.

Jensen, R. B. and K. Gerdes. 1995. Programmed cell death in bacteria: proteic plasmid stabilization systems. *Molecular Microbiology* 17:205.

Jensen, R. B. and K. Gerdes. 1997. Partitioning of plasmid R1. The ParM protein exhibits ATPase activity and interacts with the centromere-like ParR-parC complex. *Journal of Molecular Biology* 269:505–513.

Karem, K. L., S. Chatfield, N. Kuklin, and B. T. Rouse. 1995. Differential induction of carrier antigen-specific immunity by *Salmonella typhimurium* live-vaccine strains after single mucosal or intravenous immunization of BALB/c mice. *Infection and Immunity* 63:4557–4563.

Karmali, M. A. 1989. Infection by verocytotoxin-producing *Escherichia coli*. *Clinical Microbiological Reviews* 2: 15.

Karmali, M. A., M. Petric, C. Lim, P. C. Fleming, and B. T. Steele. 1983. *Escherichia coli* cytotoxin, haemolytic-uraemic syndrome, and haemorrhagic colitis. *Lancet ii*: 1299.

Karmali, M. A., M. Petric, C. Lim, P. C. Fleming, G. S. Arbus, and H. Lior. 1985. The association between idiopathic hemolytic uremic syndrome and infection by verotoxin-producing *Escherichia coli*. *Journal of Infectious Diseases* 151:775.

Karpman, D., H. Connell, M. Svensson, F. Scheutz, P. Alm, and C. Svanborg. 1997. The role of lipopolysaccharide and Shiga-like toxin in a mouse model of *Escherichia coli* O0157:H7 infection. *Journal of Infectious Diseases* 175:611.

Keusch, G. T., G. F. Grady, L. J. Mata, and J. McIver. 1972. Pathogenesis of *shigella* diarrhea. 1. Enterotoxin production by *Shigella dysenteriae* 1. *Journal of Clinical Investigation* 51:1212.

Killeen, K. P., V. Escuyer, J. J. Mekalanos, and R. J. Collier. 1992. Reversion of recombinant toxoids: mutations in diphtheria toxin that partially compensate for active-site deletions. *Proceeding of the National Academy of Sciences USA* 89: 6207.

Kim, J. Y., H. A. Kang, and D. D. Ryu. 1993. Effects of the par locus on the growth rate and structural stability of recombinant cells. *Biotechnology Progress* 9:548.

Konowalchuk, J., J. I. Speirs, and S. Stavric. 1977. Vero response to a cytotoxin of *Escherichia coli*. *Infection and Immunity* 18:775.

Langermann, S., S. Palaszynski, A. Sadziene, C. K. Stover, and S. Koenig. 1994. Systemic and mucosal immunity induced by BCG vector expressing outer-surface protein A of *Borrelia burgdorferi*. *Nature* 372: 552–555.

Lee, S. F., R. J. March, S. A. Halpern, G. Faulkner, and L. Gao. 1999. Surface expression of a protective recombinant pertussis toxin S1 subunit fragment in *Streptococcus gordonii*. *Infect Immun* 67: 1511–1516.

Lehnherr, H. and M. B. Yarmolinsky. 1995. Addiction protein Phd of plasmid prophage P1 is a substrate of the ClpXP serine protease of *Escherichia coli. Proceedings of the National Academy of Sciences USA* 92:3274.

Lehnherr, H., E. Maguin, S. Jafri, and M. B. Yarmolinsky. 1993. Plasmid addiction genes of bacteriophage P1: doc, which causes cell death on curing of prophage, and phd, which prevents host death when prophage is retained. *Journal of Molecular Biology* 233:414.

Levine, M. M., J. E. Galen, E. M. Barry, F. Noriega, S. Chatfield, M. Sztein, G. Dougan, and C. O. Tacket. 1996. Attenuated *Salmonella* as live oral vaccines against typhoid fever and as live vectors. *Journal of Biotechnology* 44:193.

Lindgren, S. W., J. E. Samuel, C. K. Schmitt, and A. D. O'Brien. 1994. The specific activities of Shiga-like toxin type II (SLT-II) and SLT-II-related toxins of enterohemorrhagic *Escherichia coli* differ when measured by Vero cell cytotoxicity but not by mouse lethality. *Infection and Immunity* 62:623.

Lloyd, R. G. and K. B. Low. 1996. Homologous recombination. In *Escherichia coli* and *Salmonella: Cellular and molecular biology*. 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 2236.

Loh, S. M., D. S. Cram, and R. A. Skurray. 1988. Nucleotide sequence and transcriptional analysis of a third function (FIm) involved in F plasmid maintenance. *Gene* 66: 259–268.

Lohman, T. M. and M. E. Ferrari. 1994. *Escherichia Coil* single-stranded DNA-binding protein: multiple DNA-binding modes and cooperativities. *Annual Reviews in Biochemistry* 63:527.

Louise, C. B. and T. G. Obrig. 1995. Specific interaction of *Escherichia coli* O157:H7-derived Shiga-like toxin II with human renal endothelial cells. *Journal of Infectious Diseases* 172:1397.

Love, C. A., P. E. Lilley, and N. E. Dixon. 1996. Stable high-copy-number bacteriophage lambda promoter vectors for overproduction of proteins in *Escherichia coli*. *Gene* 176:49.

Lynch, A. S. and E. C. C. Lin. 1996. Responses to molecular oxygen. In *Escherichia coli and Salmonella: Cellular and molecular biology*. 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 1526.

Magnuson, R., H. Lehnherr, G. Mukhopadhyay, and M. B. Yarmolinsky. 1996. Autoregulation of the plasmid addiction operon of bacteriophage P1. *Journal of Biological Chemistry* 271:18705.

Makoff, A. J., and A. E. Smallwood. 1988. Heterologous expression in *Escherichia coli*: effects of alterations in the sequence 5' to the initiation codon. *Biochem Soc Trans* 16: 48–49.

Mangeney, M., C. A. Lingwood, S. Taga, B. Caillou, T. Tursz, and J. Wiels. 1993. Apoptosis induced in Burkitt's lymphoma cells via Gb$_3$/CD77, a glycolipid antigen. *Cancer Research* 53:5314.

Marshall, J., R. Molloy, G. W. J. Moss, J. R. Howe, and T. E. Hughes. 1995. The jellyfish green fluorescent protein: a new tool for studying ion channel expression and function. *Neuron* 14:211.

Martinez-Flores, I., R. Cano, V. H. Bustamante, E. Calva, and J. L. Puente. 1999. The ompB operon partially determines differential expression of ompC in *Salmonella typhi* and *Escherichia coli*. *J Bacteriol* 181: 556–562.

Matthews, R. G. 1996. One-carbon metabolism. In *Escherichia coli and Salmonella: Cellular and molecular biology*. 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 600.

Maurizi, M. R., W. P. Clark, Y. Katayama, S. Rudikoff, J. Pumphrey, B. Bowers, and S. Gottesman. 1990. Sequence and structure of Clp P, the proteolytic component of the ATP-dependent Clp protease of *Escherichia coli*. *Journal of Biological Chemistry* 265:12536.

McClelland, M. and. R. Wilson. 1998. Sample sequencing of the *Salmonella typhi* genome: comparison to the *E. coli* K-12 genome. *Infection and Immunity*.

McDaniel, T. K., K. G. Jarvis, M. S. Donnenberg, and J. B. Kaper. 1995. A genetic locus of enterocyte effacement conserved among diverse enterobacterial pathogens. *Proceedings of the National Academy of Sciences USA* 92:1664.

McDermott, P. J., P. Gowland, and P. C. Gowland. 1993. Adaptation of *Escherichia coli* growth rates to the presence of pBR322. *Lett Appl Microbiol* 17: 139–143.

Meacock, P. A., and S. N. Cohen. 1980. Partitioning of bacterial plasmids during cell division: a cis-acting locus that accomplishes stable plasmid inheritance. *Cell* 20: 529–542.

Medaglini, D., G. Pozzi, T. P. King, and V. A. Fischetti. 1995. Mucosal and systemic immune responses to a recombinant protein expressed on the surface of the oral commensal bacterium *Streptococcus gordonii* after oral colonization. *Proc Natl Acad Sci USA* 92: 6868–6872.

Melton-Celsa, A. R. and A. D. O'Brien. 1998. The structure, biology, and relative toxicity for cells and animals of Shiga toxin family members. In *Escherichia coli* O157:H7 and other Shiga toxin-producing *E. coli* strains. J. B. Kaper and A. D. O'Brien, eds. ASM Press, Washington, D.C. In press.

Mikkelsen, N. D. and K. Gerdes. 1997. Sok antisense RNA from plasmid R1is functionally inactivated by RNaseE and polyadenylated by poly(A) polymerase I. *Molecular Microbiology* 26:311.

Miller, C. A., S. L. Beaucage, and S. N. Cohen. 1990. Role of DNA superhelicity in partitioning of the pSC101 plasmid. *Cell* 62: 127–133.

Moxley, R. A. and D. H. Francis. 1998. Overview of Animal Models. In *Escherichia coli* O157:H7 and other Shiga toxin-producing *E. coli* strains. J. B. Kaper and A. D. O'Brien, eds. ASM Press, Washington, D.C. In press.

Muhldorfer, I., J. Hacker, G. T. Keusch, D. W. Acheson, H. Tschape, A. V. Kane, A. Ritter, T. Olschlager, and A. Donohue-Rolfe. 1996. Regulation of the Shiga-like toxin II operon in *Escherichia coli*. *Infection and Immunity* 64:495.

Nakayama, K., S. M. Kelley, and R. Curtiss III. 1988. Construction of an Asd$^+$ expression-cloning vector: stable maintenance and high level expression of cloned genes in a *Salmonella* vaccine strain. *Bio/Technology* 6: 693–697.

Nakayama, K., S. M. Kelley, and R. Curtiss III. 1988. Construction of an Asd$^+$ expression-cloning vector: stable maintenance and high level expression of cloned genes in a *Salmonella* vaccine strain. *Bio/Technology* 6:693.

Nelson, S., S. E. Richardson, C. A. Lingwood, M. Petric, and M. A. Karmali. 1994. Biological activity of verocytotoxin (VT)2c and VT1/VT2c chimeras in the rabbit model. In *Recent advances in <verocytotoxin-producing Escherichia coli infections*. M. A. Karmali and A. G. Goglio, eds. Elsevier Science, New York, p. 245.

Niki, H., and S. Hiraga. 1997. Subcellular distribution of actively partitioning F plasmid during the cell division cycle of *E. coli*. *Cell* 90. 951–957.

Nordstrom, K. and S. J. Austin. 1989. Mechanisms that contribute to the stable segregation of plasmids. *Annual Reviews in Genetics* 23:37.

Noriega, F. R., G. Losonsky, J. Y. Wang, S. B. Formal, and M. M. Levine. 1996. Further characterization of ΔaroA ΔvirG *Shigella flexneri* 2a strain CVD 1203 as a mucosal *Shigella* vaccine and as a live-vector vaccine for delivering antigens of enterotoxigenic *Escherichia coli*. *Infect Immun* 64: 23–27.

Norioka, S., G. Ramakrishnan, K. Ikenaka, and M. Inouye. 1986. Interaction of a transcriptional activator, OmpR, with reciprocally osmoregulated genes, ompF and ompC, of *Escherichia coli*. *Journal of Biological Chemistry* 261:17113–17119.

Nyholm, P., G. Magnusson, Z. Zheng, R. Norel, B. Binnington-Boyd, and C. A. Lingwood. 1996. Two distinct binding sites for globotriaosyl ceramide on verotoxins: identification by molecular modelling and confirmation using deoxy analogues and a new glycolipid receptor for all verotoxins. *Chemistry and Biology* 3:263.

Nyholm, P., J. L. Brunton, and C. A. Lingwood. 1995. Modelling of the interaction of verotoxin-1 (VT1) with its glycolipid receptor, globotriaosylceramide ($Gb_3$). *Intentional Journal of Biological Macromolecules* 17:199.

O'Brien, A. D. 1982. Innate resistance of mice to *Salmonella typhi* infection. *Infection and Immunity* 38:948.

O'Brien, A. D., V. L. Tesh, A. Donohue-Rolfe, M. P. Jackson, S. Olsnes, K. Sandvig, A. A. Lindberg, and G. T. Keusch. 1992. Shiga toxin: biochemistry, genetics, mode of action, and role in pathogenesis. *Current Topics in Microbiology and Immunology* 180:65.

Olitsky, P. K. and I. J. Kligler. 1920. Toxins and antitoxins of *Bacillus dysenteriae* Shiga. *Journal of Experimental Medicine* 31:19.

Orosz, A., I. Boros, and P. Venetianer. 1991. Analysis of the complex transcription termination region of the *Escherichia coli* rrnB gene. *European Journal of Biochemistry* 201:653.

Oxer, M. D., C. M. Bentley, J. G. Doyle, T. C. Peakman, I. G. Charles, and A. J. Makoff. 1991. High level heterologous expression in *E. coli* using the anaerobically-activated nirB promoter. *Nucleic Acids Research* 19:2889–2892.

Pallen, M. J. and B. W. Wren. 1997. The HtrA family of serine proteases. *Molecular Microbiology* 26:209.

Pecota, D. C., C. S. Kim, K. Wu, K. Gerdes, and T. K. Wood. 1997. Combining the hoklsok, parDE, and pnd postsegregational killer loci to enhance plasmid stability. *Applied and Environmental Microbiology* 63:1917–1924.

Perera, L. P., J. E. Samuel, R. K. Holmes, and A. D. O'Brien. 1991. Mapping the minimal contiguous gene segment that encodes functionally active Shiga-like toxin II. *Infection and Immunity* 59:829.

Perera, L. P., J. E. Samuel, R. K. Holmes, and A. D. O'Brien. 1991. Identification of three amino acid residues in the B subunit of Shiga toxin and Shiga-like toxin type II that are essential for holotoxin activity. *Journal of Bacteriology* 173:1151.

Pittard, A. J. 1996. Biosynthesis of the aromatic amino acids. In *Escherichia coli and Salmonella: Cellular and molecular biology*. 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 458.

Polisky, B. 1986. Replication control of the ColE1-type plasmids. *In Maximizing gene expression*. W. S. Reznikoff and L. Gold, eds. Butterworths, Boston, p. 143.

Porter, R. D., S. Black, S. Pannuri, and A. Carlson. 1990. Use of the *Escherichia coli* ssb gene to prevent bioreactor takeover by plasmidless cells. *Bio/Technology* 8:47.

Pouwels, P. H., R. J. Leer, M. Shaw, M. J. Heijne den Bak-Glashouwer, F. D. Tielen, E., Smit, B. Martinez, J. Jore, and P. L. Conway. 1998. Lactic acid bacteria as antigen delivery vehicles for oral immunization purposes. *Int J Food Microbiol* 41: 155–167.

Pratt, L. A., W. Hsing, K. E. Gibson, and T. J. Silhavy. 1996. From acids to osmZ: mutiple factors influence synthesis of the OmpF and ompC porins in *Escherichia coli*. *Molecular Microbiology* 20:91 1.

Puente, J. L., V. Alvarez-Scherer, G. Gosset, and E. Calva. 1989. Comparative analysis of the *Salmonella typhi* and *Escherichia coli* ompC genes. *Gene* 83:197.

Richardson, S. E., T A. Rotman, V. Jay, C. R. Smith, L. E. Becker, M. Petric, N. F. Olivieri, and M. A. Karmali. 1992. Experimental verocytotoxemia in rabbits. *Infection and Immunity* 60:4154.

Ringquist, S., S. Shinedling, D. Barrick, L Green, J. Binkley, G. D. Stormo, and L. Gold. 1992. Translation initiation in *Escherichia coli*: sequences within the ribosome-binding site. *Molecular Microbiology* 6: 1219.

Roberts, M., S. Chatfield, and G. Dougan. 1994. *Salmonella* as carriers of heterologous antigens. In *Novel delivery systems for oral vaccines*. D. T. O'Hagan, ed. CRC Press, Ann Arbor, p. 27–58.

Ruiz-Echevarria, M. J., G. Gimenez-Gallego, R. Sabariegos-Jareno, and R. Diaz-Orejas. 1995. Kid, a small protein of the parD stability system of plasmid R1, is an inhibitor of DNA replication acting at the initiation of DNA synthesis. *J Mol Biol* 247: 568–577.

Rupp, W. D. 1996. DNA repair mechanisms. In *Escherichia coli and Salmonella: Cellular and molecular biology*. 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 2277.

Ryan, E. T., J. R. Butterton, R. N. Smith, P. A. Carroll, T. I. Crean, and S. B. Calderwood. 1997a. Protective immunity against Clostridium difficile toxin A induced by oral immunization with a live, attenuated Vibrio cholerae vector strain. Infect Immun 65: 2941–2949.

Ryan, E. T., J. R. Butterton, T. Zhang, M. A. Baker, S. L. J. Stanley, and S. B. Calderwood. 1997b. Oral immunization with attenuated vaccine strains of Vibrio cholerae expressing a dodecapeptide repeat of the serine-rich Entamoeba histolytica protein fused to the cholera toxin B subunit induces systemic and mucosal antiamebic and anti-V. cholerae antibody responses in mice. Infect Immun 65: 3118–3125.

Sambrook, J., E. F. Fritsch, and T. Maniatis. 1989. *Molecular cloning: A Laboratory Manual,* 2nd edition. Cold Spring Harbor, New York: Cold Spring Harbor Laboratory Press.

Selzer, G., T. Som, T. Itoh, and J. Tomizawa. 1983. The origin of replication of plasmid p15A and comparative studies on the nucleotide sequences around the origin of related plasmids. Cell 32:119.

Shaw, K. J., P. N. Rather, R. S. Hare, and G. H. Miller. 1993. Molecular genetics of amino-glycoside resistance genes and familial relationships of the aminoglycoside-modifying enzymes. Microbiol Rev 57: 138–163.

Siegler, R. L. 1995. The hemolytic uremic syndrome. Pediatric Nephrology 42:1505.

Siegler, R. L., A. T. Pavia, R. D. Christofferson, and M. K. Milligan. 1994. A 20-year population-based study of postdiarrheal hemolytic uremic syndrome in Utah. Pediatrics 94:35.

Sixma, T. K., P. E. Stein, W. G. Hol, and R. J. Read. 1993. Comparison of the B-pentamers of heat-labile enterotoxin and verotoxin-1: two structures with remarkable similarity and dissimilarity. Biochemistry 32:191.

Srinivasan, J., S. A. Tinge, R. Wright, J. C. Herr, and R. Curtiss III. 1995. Oral immunization with attenuated Salmonella expressing human sperm antigen induces antibodies in serum and the reproductive tract. Biology of Reproduction 53:462.

Stein, P. E., A. Boodhoo, G. J. Tyrrell, J. L. Brunton, and R. J. Read. 1992. Crystal structure of the cell-binding B oligomer of verotoxin-I from *E. coli*. Nature 355:748.

Stoker, N. G., N. F. Fairweather, and B. G. Spratt. 1982. Versatile low-copy-number plasmid vectors for cloning in *Escherichia coli*. Gene 18: 335–341.

Streatfield, S. J., M. Sandkvist, T. K. Sixma, M. Bagdasarian, W. G. Hot, and T. R. Hirst. 1992. Intermolecular interactions between the A and B subunits of heat-labile enterotoxin from *Escherichia coli* promote holotoxin assembly and stability in vivo. Proceedings of the National Academy of Sciences USA 89:12140.

Strockbine, N. A., L. R. M. Marques, J. W. Newland, H. W. Smith, R. K. Holmes, and A. D. O'Brien. 1986. Two toxin-converting phages from *Escherichia coli* 01 57:H7 strain 933 encode antigenically distinct toxins with similar biologic activities. *Infection and Immunity* 53.135.

Strockbine, N. A., M. P. Jackson, L. M. Sung, R. K. Holmes, and A. D. O'Brien. 1988. Cloning and sequencing of the genes for Shiga toxin from Shigella dysenteriae Type 1. Journal of Bacteriology 170:1116.

Strugnell, R. A., D. Maskell, N. F. Fairweather, D. Pickard, A. Cockayne, C. Penn, and G. Dougan. 1990. Stable expression of foreign antigens from the chromosome of *Salmonella typhimurium* vaccine strains. *Gene* 88: 5763.

Summers, D. K. *The Biology of Plasmids*, 65–91, 1996.

Summers, D. K. 1998. Timing, self-control and sense of direction are the secrets of multicopy plasmid stability. *Mol Microbiol* 29: 1137–1145.

Summers, D. K. and D. J. Sherratt. 1984. Multimerization of high copy number plasmids causes instability: CoIE1 encodes a determinant essential for plasmid monomerization and stability. Cell 36:1097.

Tacket, C. O., D. M. Hone, R. Curtiss III, S. M. Kelly, G. Losonsky, L. Guers, A. M. Harris, R. Edelman, and M. M. Levine. 1992. Comparison of the safety and immunogenicity of ΔaroCΔaroD and ΔcyaΔcrp *Salmonella typhi* strains in adult volunteers. *Infection and Immunity* 60:536.

Tacket, C. O., M. Sztein, G. Losonsky, S. S. Wasserman, J. P. Nataro, R. Edelman, D. Pickard, G. Dougan, S. Chatfield, and M. M. Levine. 1997. Safety of live oral *Salmonella typhi* vaccine strains with deletions in htrA and aroC aroD and immune responses in humans. *Infection and Immunity* 65:452456.

Tacket, C. O., S. M. Kelley, F. Schodel, G. Losonsky, J. P. Nataro, R. Edelman, M. M. Levine, and R. Curtiss III. 1997. Safety and immunogenicity in humans of an attenuated *Salmonella typhi* vaccine vector strain expressing plasmid-encoded hepatitis B antigens stabilized by the Asd-balanced lethal vector system. *Infection and Immunity* 65:3381–3385.

Takeda, Y. 1995. Shiga and Siga-like (Vero) toxins. In Bacterial toxins and virulence factors in disease. J. Moss, B. Iglewski, M. Vaughan and A. Tu, eds. Marcel Dekker, Inc. New York, p. 313.

Tauxe, R. V. 1998. Public health perspective on immunoprophylactic strategies for *Escherichia coli* 0157:H7: who or what would we immunize? In *Escherichia coli* 0157. H7 and other Shiga toxin-producing *E. coli* strains. J. B. Kaper and A. D. O'Brien, eds. ASM Press, Washington, D.C. In press.

Tesh, V. L., J. A. Burris, J. W. Owens, V. M. Gordon, E. A. Wadolkowski, A. D. O'Brien, and J. E. Samuel. 1993. Comparison of the relative toxicities of Shiga-like toxins type I and type II for mice. *Infection and Immunity* 61:3392.

Thisted, T., A. K. Nielsen, and K. Gerdes. 1994. Mechanism of post-segregational killing: translation of Hok,SrnB and Pnd mRNAs of plasmids R1, F and R483 is activated by 3' end processing. EMBO Journal 13:1950.

Thisted, T., N. S. Sorensen, and K. Gerdes. 1995. Mechanism of post-segregational killing: secondary structure analysis of the entire Hok mRNA from plasmid R1 suggests a fold-back structure that prevents translation and antisense RNA binding. *Journal of Molecular Biology* 247:859.

Thisted, T., N. S. Sorensen, E. G. Wagner, and K. Gerdes. 1994. Mechanism of post-segregational killing: Sok antisense RNA interacts with Hok mRNA via its 5'-end single-stranded leader and competes with the 3'-end of Hok mRNA for binding to the mok translational initiation region. EMBO Journal 13:1960.

Tinge, S. A. and R. Curtiss III. 1990. Conservation of *Salmonella typhimurium* virulence plasmid maintenance regions among *Salmonella serovars* as a basis for plasmid curing. *Infection and Immunity* 58:3084.

Tinge, S. A. and R. Curtiss III. 1990. Isolation of the replication and partitioning regions of the *Salmonella typhimurium* virulence plasmid and stabilization of heterologous replicons. *Journal of Bacteriology* 35 172:5266.

Twigg, A. J., and D. Sherratt. 1980. Trans-complementable copy-number mutants of plasmid CoIE1. Nature 283: 216–218.

Umbarger, H. E. 1978. Amino acid biosynthesis and its regulation. Annual Reviews in Biochemistry 47:533.

Valdivia, R. H. and S. Falkow. 1997. Fluorescence-based isolation of bacterial genes expressed within host cells. *Science* 277:2007.

Valdivia, R. H., A. E. Hromockyj, D. Monack, L. Ramakrishnan, and S. Falkow. 1996. Applications for green fluorescent protein (GFP) in the study of host-pathogen interactions. Gene 173:47.

Van Melderen, L., P. Bernard, and M. Couturier. 1994. Lon-dependent proteolysis of CcdA is the key control for activation of CcdB in plasmid-free segregant bacteria. *Mol Microbiol* 11: 1151–1157.

Vicari, G., A. J. Olitzki, and Z. Olitzki. 1960. The action of the thermolabile toxin of *Shigella dysenteriae* on cells cultivated in vitro. *British Journal of Experimental Pathology* 41:179.

Wada, K., Y. Wada, F. Ishibashi, T. Gojobori, and T. Ikemura. 1992. Codon usage tabulated from the GenBank genetic sequence data. *Nucleic Acids Research* 20:2111.

Wadolkowski, E. A., L. M. Sung, J. A. Burris, J. E. Samuel, and AD. O'Brien. 1990. Acute renal tubular necrosis and death of mice orally infected with *Escherichia coli* strains that produce Shiga-like toxin type II. *Infection and Immunity* 58:3959.

Wahle, E., and A. Kornberg. 1988. The partition locus of plasmid pSC101 is a specific binding site for DNA gyrase. *EMBO J* 7: 1889–1895.

Wang, S. and T. Hazelrigg. 1994. Implications for bcd mRNA localization from spatial distribution of exu protein in *Drosophila* oogenesis. Nature 369:400.

Wang, Y., Z. Zhang, S. Yang, and R. Wu. 1992. Cloning of par region and the effect of par region on the stability of pUC9. *Chinese Journal of Biotechnology* 8:107.

Williams, K. R., J. B. Murphy, and J. W. Chase. 1984. Characterization of the structural and functional defect in the *Escherichia coli* single-stranded DNA binding protein encoded by the ssb1 mutant gene. *Journal of Biological Chemistry* 259:11804.

Wu, K., and T. K. Wood. 1994. Evaluation of the hok/sok killer locus for enhanced plasmid stability. *Biotechnol Bioeng* 44. 912–921.

Yamasaki, S., M. Furutani, K. Ito, K. Igarashi, M. Nishibuchi, and Y. Takeda. 1991. Importance of arginine at postion 170 of the A subunit of Vero toxin 1 produced by enterohemorrhagic *Escherichia coli* for toxin activity. *Microbial Pathogenesis* 11:1.

Yanofsky, C., T. Platt, I. P. Crawford, B. P. Nichols, G. E. Christie, H. Horowitz, M. Van Cleemput, and A. M. Wu. 1981. The complete nucleotide sequence of the tryptophan operon of *Escherichia coli. Nucleic Acids Res* 9: 6647–6668.

Yu, J. and J. B. Kaper. 1992. Cloning and characterization of the eae gene of enterohaemorrhagic *Escherichia coli. Molecular Microbiology* 6:411.

Zalkin, H. and P. Nygaard. 1996. Biosynthesis of purine nucleotides. In *Escherichia coli and Salmonella: Cellular and molecular biology.* 2nd ed. F. C. Neidhardt, J. L. Ingraham, E. C. C. Lin, K. B. Low, B. Magasanik, W. S. Reznikoff, M. Riley, M. Schaechter and H. E. Umbarger, eds. ASM Press, Washington, D.C. p.561.

Zhang, X., Y. Lou, M. Koopman, T. Doggett, K. S. K. Tung, and R. Curtiss III .1997. Antibody responses and infertility in mice following oral immunization with attenuated *Salmonella typhimurium* expressing recombinant murine ZP3. *Biology of Reproduction* 56:33.

Zoja, C., D. Corna, C. Farina, G. Sacchi, C. A. Lingwood, M. P. Doyle, V. V. Padhye, M. Abbate, and G. Remuzzi. 1992. Verotoxin glycolipid receptors determine the localization of microangiopathic process in rabbits given verotoxin-1. *Journal of Laboratory and Clinical Medicine* 120.229.

Zurita, M., F. Bolivar, and X. Soberon. 1984. Construction and characterization of new cloning vehicles. VII. Construction of plasmid pBR327par, a completely sequenced, stable derivative of pBR327 containing the par locus of pSC101. *Gene* 28:119.

What is claimed is:

1. A method for eliciting an immune response in a subject comprising administering a live attenuated bacterial vector vaccine to said subject, wherein the live attenuated bacterial vector vaccine comprises an isolated cell comprising an expression vector, wherein said expression vector comprises a nucleotide sequence encoding:
 a restricted-copy-number origin of replication cassette comprising (i) a nucleotide sequence encoding an origin of replication that limits the expression vector to an average plasmid copy number of about 2 to 75 copies per cell, (ii) a first unique restriction enzyme cleavage site located 5' of the nucleotide sequence encoding the origin of replication, and (iii) a second unique restriction enzyme cleavage site located 3' of the nucleotide sequence encoding the origin of replication;
 at least one post-segregational killing cassette comprising (i) a nucleotide sequence encoding at least one post-segregational killing locus, (ii) a first unique restriction enzyme cleavage site located 5' of the nucleotide sequence encoding the at least one post-segregational killing locus, and (iii) a second unique restriction enzyme cleavage site located 3' of the nucleotide sequence encoding the at least one post-segregational killing locus; and
 at least one partitioning cassette comprising (i) a nucleotide sequence encoding at least one partitioning function, (ii) a first unique restriction enzyme cleavage site 5' of the nucleotide sequence encoding the at least one partitioning function, and (iii) a second unique restriction enzyme cleavage site located 3' of the nucleotide sequence encoding the at least one partitioning function.

2. The method of claim 1, wherein the restricted-copy-number origin of replication is selected from the group consisting of: oriE1 (nucleotides 1250 to 1936 of SEQ ID NO: 1), ori101 (nucleotides 50 to 2004 of SEQ ID NO: 3), and ori15A (nucleotides 50 to 684 of SEQ D NO: 2).

3. The method of claim 1, wherein the average plasmid copy-number falls within the range of about 5 to about 60 copies per cell.

4. The method of claim 1, wherein the nucleotide sequence encoding the at least one post-segregational killing locus is selected from the group consisting of asd, ssb, phd-doc, kis-kid, and hok-sok.

5. The method of claim 1, wherein the partitioning function is an active partitioning function.

6. The method of claim 1, wherein the nucleotide sequence encoding the at least one partitioning function comprises parA.

7. The method of claim 1, wherein the partitioning function is a passive partitioning function.

8. The method of claim 1, wherein the nucleotide sequence encoding the at least one partitioning function is the par locus of pSC101.

9. The method of claim 1, further comprising an expression cassette comprising (i) a nucleotide sequence encoding a promoter, (ii) a first unique restriction enzyme cleavage site located 5' of the nucleotide sequence encoding the promoter, and (iii) a second unique restriction enzyme cleavage site located 3' of the nucleotide sequence encoding the promoter.

10. The method of claim 1, further comprising a selection cassette comprising (i) a nucleotide sequence encoding at least one selectable marker, (ii) a first unique restriction enzyme cleavage site located 5' of the nucleotide sequence encoding the at least one selectable marker, and (iii) a second unique restriction enzyme cleavage site located 3' of the nucleotide sequence encoding the at least one selectable marker.

11. The method of claim 1, wherein the isolated cell is an isolated bacterial cell.

12. The method of claim 1, wherein the subject is a mammal.

13. The method of claim 9, wherein the promoter is an inducible promoter.

14. The method of claim 9, wherein the expression cassette further comprises a nucleotide sequence encoding an antigen of interest located at the 3' end of nucleotide sequence encoding the promoter.

15. The method of claim 13, wherein the promoter is an ompC promoter.

16. The method of claim 15, wherein the ompC promoter is a polynucleotide fragment from *E. coli* spanning nucleotides +70 through −389, relative to the transcriptional start site +1, of ompC.

17. The method of claim 15, wherein the ompC promoter comprises the following sequence: AGATCX$^1$X$^2$TAAX$^3$C-ATCCACAGGAGGATATCTGATG (SEQ ID NO:36), wherein X$^1$ is selected from the group consisting of G, C and A; X$^2$ is an insert having from 1 to 5 nucleotides; and X$^3$ is selected from the group consisting of A, T, G and C.

18. The method of claim 17, wherein X$^1$ is G.

19. The method of claim 17, wherein X$^2$ has from 1 to 4 nucleotides.

20. The method of claim 17, wherein X$^2$ has 4 nucleotides.

21. The method of claim 17, wherein X$^2$ has 4 nucleotides, independently selected from the group consisting of A, T and C.

22. The method of claim 17, wherein X$^2$ comprises a nucleotide or nucleotide sequence selected from the group consisting of ATCT; ATC; AT; TCT; CT; TC; A; T; C; and T.

23. The method of claim 17, wherein X$^2$ is selected from the group consisting of ATCT; ATC; AT; TCT; CT; TC; A; T; C; and T.

24. The method of claim 17, wherein X$^2$ is ATCT.

25. The method of claim 17, wherein X$^3$ is A.

26. The method of claim 14, wherein the antigen of interest is selected from the group consisting of a viral antigen, a bacterial antigen, a cancer antigen, and an autoimmune antigen.

27. The method of claim 14, wherein the antigen of interest comprises a detoxified Shiga toxin.

28. The method of claim 27, wherein the antigen of interest comprises a detoxified Shiga toxin 2 antigen selected from the group consisting of a Shiga toxin 2 B subunit pentamer and a genetically detoxified Shiga toxin 2.

29. The method of claim 28, wherein the gene encoding the detoxified Shiga toxin 2 has modified segments selected from the group consisting of:

```
                                      (SEQ ID NO:37)
(797)-  ACA GCA GAG GCG TTA - (811);

(SEQ ID NO:38)
(902)-  CTG AAC CTA GGG CGA    (916);

(SEQ ID NO:39)
(1345)- GAA TTC GCG ACC AGT - (1359); and (SEQ ID NO:40)
(1435)- GAA TCA GAT TCT GGA - (1449).
```

30. The method of claim 10, wherein the selectable marker is a protein which provides resistance to an antibiotic selected from the group consisting of aminoglycosides, ansamycins, antimycotics, penicillins, cephalosporins, chloramphenicols, linosamides, macrolides, peptolides, and tetracyclines.

31. The method of claim 10, wherein the nucleotide sequence encoding the selectable marker is selected from the group consisting of tetA, bla, aphA-2, and kan.

32. The method of claim 11, wherein the isolated bacterial cell is *Salmonella typhi*.

33. The method of claim 11, wherein the isolated bacterial cell is a *Salmonella typhi* strain.

34. The method of claim 12, wherein the subject is a human.

35. The method of claim 12, wherein the subject is a bovine.

* * * * *

UNITED STATES PATENT AND TRADEMARK OFFICE
CERTIFICATE OF CORRECTION

| | |
|---|---|
| PATENT NO. | : 6,969,513 B2 |
| APPLICATION NO. | : 10/750965 |
| DATED | : November 29, 2005 |
| INVENTOR(S) | : James E. Galen |

It is certified that error appears in the above-identified patent and that said Letters Patent is hereby corrected as shown below:

The sentence bridging lines 17-18 of column 1 should read as follows:

"The U.S. Government has certain rights in this invention."

Signed and Sealed this

Fifth Day of August, 2008

JON W. DUDAS
*Director of the United States Patent and Trademark Office*